(12) United States Patent
Davalos et al.

(10) Patent No.: US 8,968,542 B2
(45) Date of Patent: Mar. 3, 2015

(54) DEVICES AND METHODS FOR CONTACTLESS DIELECTROPHORESIS FOR CELL OR PARTICLE MANIPULATION

(75) Inventors: Rafael V. Davalos, Blacksburg, VA (US); Hadi Shafiee, Blacksburg, VA (US); Michael B. Sano, Blacksburg, VA (US); John L. Caldwell, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 906 days.

(21) Appl. No.: 12/720,406

(22) Filed: Mar. 9, 2010

(65) Prior Publication Data

US 2010/0224493 A1 Sep. 9, 2010

Related U.S. Application Data

(60) Provisional application No. 61/158,553, filed on Mar. 9, 2009, provisional application No. 61/252,942, filed on Oct. 19, 2009.

(51) Int. Cl.
*B01D 57/02* (2006.01)
*B03C 5/02* (2006.01)
*B03C 5/00* (2006.01)

(52) U.S. Cl.
CPC .............. *B03C 5/022* (2013.01); *B03C 5/005* (2013.01); *B01D 57/02* (2013.01)
USPC .......................................... 204/547; 204/643

(58) Field of Classification Search
CPC .......... B03C 5/005; B03C 5/02; B03C 5/026; B01D 57/02
USPC ................................................. 204/547, 643
See application file for complete search history.

(56) References Cited

U.S. PATENT DOCUMENTS

| 4,326,934 A * | 4/1982 | Pohl ............................. 204/547 |
| 5,180,480 A * | 1/1993 | Manz ........................... 204/644 |
| 2004/0050697 A1* | 3/2004 | Eckerskorn et al. .......... 204/450 |
| 2008/0105565 A1* | 5/2008 | Davalos et al. ............... 205/775 |

OTHER PUBLICATIONS

Demierre et al. Lab Chip, 2007, 7, 355-365.*
Kang et al. Electrophoresis 2006, 27, 694-702.*
Sabounchi et al. Biomed Microdevices (2008) 10:661-670.*
Sun et al. (Microfluid. Nanofluid. 2009 6:589-598, published online Aug. 7, 2008).*
Kohlheyer et al. (Anal. Chem. 2007, 79, 8190-8198).*
Morgan, et al.; "AC Electrokinetics: Colloids and Nanoparticles"; Research Studies Press Ltd. and Institute of Physics Publishing, 2003, ISBN 0-86380-255-259.
Armstrong, et al.; "Rapid CE Microbial Assays for Consumer Products that Contain Active Bacteria"; FEMS Microbiology Letters, 2001, pp. 33-37, vol. 194.

(Continued)

*Primary Examiner* — Luan Van
*Assistant Examiner* — Steven Rosenwald
(74) *Attorney, Agent, or Firm* — Blank Rome LLP

(57) ABSTRACT

Devices and methods for performing dielectrophoresis are described. The devices contain sample channel which is separated by physical barriers from electrode channels which receive electrodes. The devices and methods may be used for the separation and analysis of particles in solution, including the separation and isolation of cells of a specific type. As the electrodes do not make contact with the sample, electrode fouling is avoided and sample integrity is better maintained.

3 Claims, 39 Drawing Sheets

(56) References Cited

OTHER PUBLICATIONS

Armstrong, et al.; "Separating Microbes in the Manner of Molecules. 1. Capillary Electrokinetic Approaches"; Annals of Chemistry., 1999, pp. 5465-5469, vol. 71.
Girod, et al.; "Monitoring the Migration Behavior of Living Microorganisms in Capillary Electrophoresis Using Laser-Induced Fluorescence Detection with a Charge-Coupled Device Imaging System"; Electrophoresis, 2002, pp. 5465-5469, vol. 23.
Cabrera, et al.; "Continuous Concentration of Bacteria in a Microfluidic Flow Cell Using Electrokinetic Techniques"; Electrophoresis, 2001, pp. 355-362, vol. 22.
Beckert, et al.; "The Removal of Human Leukaemia Cells from Blood Using Interdigitated Microelectyrodes"; 1994, pp. 2659-2662, Journal of Physics D: Applied Physics, vol. 27.
Gascoyne, et al.; "Dielectrophoretic Separation of Cancer Cells from Blood"; IEEE Transactions on Industry Applications. May/Jun. 1997, vol. 33, No. 3.
Huang, et al.; "Dielectrophoretic Cell Separation and Gene Expression Profiling on Microelectronic Chip Arrays"; Analytical Chemistry, 2002, pp. 3362-3371, vol. 74, No. 14.
Cheng, et al.; "Isolation of Cultured Cervical Carcinoma Cells Mixed with Peripheral Blood Cells on a Bioelectronic Chip"; Analytical Chemistry, 1998, pp. 2321-2326, vol. 70, No. 11.
Altomare, et al.; "Levitation and Movement of Human Tumor Cells Using a Printed Circuit Board Device Based on Software-Controlled Dielectrophoresis"; 2003, pp. 474-479, Wiley Periodicals, DOI: 10.1002/bit. 10590.
Markx, et al.; "Separation of Viable and Non-Viable Yeast Using Dielectrophoresis"; Journal of Biotechnology, 1994, pp. 29-37, vol. 32.
Das, et al.; "Dielectrophoretic Segregation of Different Human Cell Types on Microscope Slides"; Analytical Chemistry, 2005, pp. 2708-2719, vol. 77, No. 9.
Gascoyne, et al.; "Isolation of rare cells from cell mixtures by Dielectrophoresis", Electrophoresis, 2009, pp. 1388-1398, vol. 30.
Apostolaki, et al.; "Circulating HER2 mRNA-Positive Cells in the Peripheral Blood of Patients with Stage I and II Breast Cancer After the Administration of Adjuvant Chemotherapy: Evaluation of Their Clinical Relevance"; Annals of Oncology, 2007, pp. 851-858, vol. 18.
Cristofanilli; "The "Microscopic" Revolution in Breast Carcinoma are We Ready to Change Clinical Practice?"; Cancer, 2005, pp. 877-880, vol. 103, No. 5.
Fizazi, et al.; "High Detection Rate of Circulating Tumor Cells in Blood of Patients with Prostate Cancer Using Telomerase Activity"; Annals of Oncology, 2007, pp. 518-521, vol. 18.
Hayes, et al.; "Circulating Tumor Cells at Each Follow-up Time Point During Therapy of Metastatic Breast Cancer Patients Predict Progression-Free and Overall Survival"; Clinical Cancer Research, 2006, pp. 4218-4224, vol. 12, No. 14.
Naoe, et al.; "Detection of Circulating Urothelial Cancer Cells in the Blood Using the Cell Search System"; Cancer, 2007, pp. 1439-1445, vol. 109, No. 7.
Osman, et al.; "Detection of Circulating Cancer Cells Expressing Uroplakins and Epidermal Growth Factor Receptor in Bladder Cancer Patients"; International. Journal on Cancer, 2004, pp. 934-939, vol. 111.
Galán, et al; "Detection of Occult Breast Cancer Cells by Amplification of CK19 mRNA by Reverse Transcriptase-Polymerase Chain Reaction: Role of Surgical Manipulation"; Anticancer Research, 2002, pp. 2877-2884. vol. 22.
Dingemans, et al; "Detection of Cytokeratin-19 Transcripts by Reverse Transcriptase-Polymerase Chain Reaction in Lung Cancer Cell Lines and Blood of Lung Cancer Patients"; Laboratory Investigation, 1997, pp. 213-220, vol. 77, No. 3.
Berteau, et al.; "Molecular Detection of Circulating Prostate Cells in Cancer II: Comparison of Prostate Epithelial Cells Isolation Procedures"; Clinical Chemistry, 1998, pp. 1750-1753, vol. 44, No. 8.
Berteau, et al.; "Influence of Blood Storage and Sample Processing on Molecular Detection of Circulating Prostate Cells in Cancer"; Clinical Chemistry, 1998, pp. 677-679, vol. 44, No. 3.
Koike, et al.; "Endoscopic Ultrasonography in Patients with Thyroid Cancer: Its Usefulness and Limitations for Evaluating Esophagopharyngeal Invasion"; Endoscopy, 2002, pp. 457-460, vol. 34, Issue 6.
Schröder, et al.; "Detection of Micrometastatic Breast Cancer by Means of Real Time Quantitative RT-PCR and Immunostaining in Perioperative Blood Samples and Sentinel Nodes"; Int. J. Cancer, vol. 106, 611-618 (2003).
Traweek, et al.; "Keratin Gene Expression in Non-Epithelial Tissues—Detection with Polymerase Chain Reaction"; American Journal of Pathology, 1993, pp. 1111-1118, vol. 142, No. 4.
Pohl; "The Motion and Precipitation of Suspensoids in Divergent Electric Fields"; Journal of Applied Physics, 1915, pp. 869-871, vol. 22, No. 7.
Pohl; "Some Effects of Nonuniform Fields on Dielectrics"; Journal of Applied Physics, 1958, pp. 1182-1188, vol. 29, No. 8.
POHL; "Dielectrophoresis—The Behavior of Neutral Matter in Nonuniform Electric Fields"; Cambridge University Press, 1978, pp. 350-356 + 441-442.
Tapper, et al.; "In Vivo Measurement of the Dynamic 3-D Kinematics of the Ovine Stifle Joint"; Journal of Biomechanical Engineering, 2004, pp. 301-318, vol. 126.
Jen, et al.; "Selective Trapping of Live and Dead Mammalian Cells Using Insulator-Based Dielectrophoresis Within Open-Top Microstructures"; Biomed Microdevices, 2009, pp. 597-607, vol. 11.
Steffen, et al; "Dielectrophoretic Microfluidic—Microfluidic Technologies for Miniaturized Analysis Systems"; 2007, pp. 337.
Hughes; "Strategies for Dielectrophoretic Separation in Laboratory-On-A-Chip Systems"; Electrophoresis, 2002, pp. 2569-2582, vol. 23.
Simmons, et al.; "The Development of Polymeric Devices as Dielectrophoretic Separators and Concentrators"; MRS Bulletin, 2006, pp. 120-124, vol. 31.
Sabounchi, et al.; "Sample Concentration and Impedance Detection on a Microfluidic Polymer Chip"; Biomed Microdevices, 2008, pp. 661-670, vol. 10.
Kang, et al.; "DC-Dielectrophoretic Separation of Biological Cells by Size"; Biomed Microdevices, 2008, pp. 243-249, vol. 10.
Cummings, et al.; "Dielectrophoresis in Microchips Containing Arrays of Insulating Posts: Theoretical and Experimental Results"; Analytical Chemistry, 2003, pp. 4724-4731, vol. 75, No. 18.
Sabounchi, et al.; "Joule Heating Effects on Insulatorbased Dielectrophoresis"; Presented at Twelfth International Conference on Miniaturized Systems for Chemistry and Life Sciences Oct. 12-16, 2008, pp. 50-52, San Diego, California, USA.
Shafiee, et al.; "Contactless Dielectrophoresis: a New Technique for Cell Manipulation"; Biomed Microdevices, 2009, pp. 997-1006, vol. 11.
Borgatti, et al.; "Antibody-Antigen Interactions in Dielectrophoresis Buffers for Cell Manipulation on Dielectrophoresis-Based Lab-on-A-Chip devices"; Minerva Biotec, 2007, pp. 71-74, vol. 19.
Del Bene, et al.; "A Model-Based Approach to the In Vitro Evaluation of Anticancer Activity"; Cancer Chemother Pharmacol, 2009, 827-836, vol. 63.
Ntouroupi, et al.; "Detection of Circulating tumour Cells in Peripheral Blood with an Automated Scanning Fluorescence Microscope"; British Journal of Cancer, 2008, pp. 789-795, vol. 99.
Tatosian, et al.; "A Novel System for Evaluation of Drug Mixtures for Potential Efficacy in Treating Multidrug Resistant Cancers"; Biotechnology and Bioengineering, 2009, pp. 187-198, vol. 103, No. 1.
Leary, et al.; "High-Throughput Cell Analysis and Sorting Technologies for Clinical Diagnostics and Therapeutics"; Clinical Diagnostic Systems, Gerald E. Cohn, Editor, Proceedings of SPIE, 2001, pp. 16-27, vol. 4255.
Shafiee, et al.; "Selective Isolation of Live/Dead Cells Using Contactless Dielectrophoresis (cDEP)†"; Lab Chip, pp. 438-445, 2010, vol. 10.

(56) References Cited

OTHER PUBLICATIONS

Arnold, et al.; "Rotating-Field-Induced Rotation and Measurement of Membrane Capacitance of Single Mesophyll Cells of Avena Sativa"; Verlag Der Zeitschrift Für Naturforschung Tübingen, 1982, pp. 908-915, vol. 37c, No. 10.

Ashkin, et al; "Optical Trapping and Manipulation of Single Cells Using Infrared Laser Beams"; Nature, 1987, pp. 24-31, vol. 330.

Davalos, et al.; "Performance Impact of Dynamic Surface Coatings on Polymeric Insulator-Based Dielectrophoretic Particle Separators"; Annals of Bioanalytical Chemistry, 2008, pp. 847-855, vol. 390.

Davalos, et al.; "Tissue Ablation with Irreversible Electroporation"; Annals of Biomedical Engineering, 2005, pp. 223-231, vol. 33, No. 2.

Dussaud, et al.; "Particle Segregation in Suspensions Subject to High-Gradient AC Electric Fields"; Journal of Applied Physics, 2000, pp. 5463-5473, vol. 88, No. 9.

Flanagan, et al.; "Unique Dielectric Properties Distinguish Stem Cells and Their Differentiated Progeny"; Stem Cells, 2008, pp. 656-665, vol. 26.

Fu, et al.; "A Microfabricated Fluorescence-Activated Cell Sorter"; Nature Biotechnology, 1999, pp. 1109-1111, vol. 17.

Gascoyne, et al.; "Dielectrophoresis-Based Sample Handling in General-Purpose Programmable Diagnostic Instruments"; Proceedings of the IEEE, 2004, pp. 22-42, vol. 92, No. 1.

Giddings; "Field-Flow Fractionation: Analysis of Macromolecular, Colloidal, and Particulate Materials"; Science, New Series, 1993, pp. 1456-1465, vol. 260, No. 5113.

Lapizco-Encinas, et al.; "An Insulator-Based (Electrodeless) Dielectrophoretic Concentrator for Microbes in Water"; Journal of Microbiological Methods, 2005, pp. 317-326, vol. 62.

Lapizco-Encinas, et al.; "Protein Manipulation with Insulator-Based Dielectrophoresis and Direct Current Electric Fields"; Journal of Chromatography A, 2008, pp. 45-51, vol. 206.

Masuda, et al.; "Detection of Extremely Small Particles in the Nanometer and Ionic Size Range"; IEEE Transactions on Industry Applications, 1988, pp. 740-744, vol. 24, No. 4.

Miltenyi, et al.; "High Gradient Magnetic Cell Separation With MACS1"; Cytometry, 1990, pp. 231-238, vol. 11.

Wong, et al.; "Electrokinetics in Micro Devices for Biotechnology Applications"; IEEE/ASME Transactions on Mechatronics, 2004, pp. 366-376, vol. 9, No. 2.

Yang, et al.; "Cell Separation on Microfabricated Electrodes Using Dielectrophoretic/Gravitational Field-Flow Fractionation"; Analytical Chemistry, 1999, pp. 911-918, vol. 71, No. 5.

Chou, et al.; "Electrodeless Dielectrophoresis of Single- and Double-Stranded DNA"; Biophysical Journal, 2002, pp. 2170-2179, vol. 83.

Edd, et al.; "Mathematical Modeling of Irreversible Electroporation for Treatment Planning"; Technology in Cancer Research & Treatment, 2007, pp. 275-286, vol. 6, No. 4.

Suehiro, et al.; "Selective Detection of Viable Bacteria using Dielectrophoretic Impedance Measurement Method"; Journal of Electrostatics, 2003, pp. 157-168, vol. 57.

Li, et al.; "Dielectrophoretic Separation and Manipulation of Live and Heat-Treated Cells of Listeria on Microfabricated Devices with Interdigitated Electrodes"; Sensors and Actuators B, 2002, pp. 215-221, vol. 86.

Huang, et al.; "Differences in the AC Electrodynamics of Viable and Non-Viable Yeast Cells Determined Through Combined Dielectrophoresis and Electrorotation Studies"; Physics in Medicine and Biology, 1992, pp. 1499-1517, vol. 37, No. 7.

Docoslis, et al.; "A Novel Dielectrophoresis-Based Device for the Selective Retention of Viable Cells in Cell Culture Media"; Biotechnology and Bioengineering, 1997, pp. 239-250, vol. 54, No. 3.

Jones; "Electromechanics of Particles"; Cambridge University Press, ISBN 0-521-43196-4, 1995.

Morgan, et al.; "Single Cell Dielectric Spectroscopy"; Journal of Physics. D: Applied Physics, 2007, pp. 61-70, vol. 40, Published Dec. 15, 2006.

Bruus; "Theoretical Microfluidics"; Oxford University Press, 2008, ISBN 978-0-19-923508.

Manginell, et al.; "BioMEMS and Bioanotechnology"; Materials Research Society, Symposium Proceedings, 2002, vol. 729, ISBN 1-55899-665-6.

Asbury, et al.; "Trapping of DNA by Dielectrophoresis"; Electrophoresis, 2002, pp. 2658-2666, vol. 23.

Green, et al.; "Numerical Determination of the Effective Moment of Non-Spherical Particles"; Journal of Physics. D: Applied Physics, 2007, pp. 78-85, vol. 40.

Urdaneta, et al.; "Multiple Frequency Dielectrophoresis"; Electrophoresis, 2007, pp. 3145-3155, vol. 28.

Irimajiri, et al.; "A Dielectric Theory of "Multi-Stratified Shell" Model with its Application to a Lymphoma Cell"; Journal of Theoretical Biology, 1979, pp. 251-269, vol. 78.

Weaver; "Electroporation Theory Concepts and Mechanisms"; Methods in Molecular Biology, 1995, pp. 3-28, vol. 55, (Plant Cell Electroporation and Electrofusion Protocols), Humana Press.

Davalos, et al.; "Electroporation: Bio-Electrochemical Mass Transfer at the Nano Scale"; Microscale Thermophysical Engineering, 2000, pp. 147-159, vol. 4.

Lee, et al.; "Microfluidic Electroporation of Robust 10-Mu Vesicles for Manipulation of Picoliter Volumes"; Biochemistry, 2006, pp. 117-125, vol. 69.

Shafiee, et al.; "A Preliminary Study to Delineate Irreversible Electroporation from Thermal Damage Using the Arrhenius Equation"; Journal of Biomechanical Engineering, 2009, pp. 074509-1-074509-5, vol. 131.

Lapizco-Encinas et al., "Dielectrophoretic Concentration and Separation of Live and Dead Baceria in an Array of Insulators," Annals of Chemistry, 2004, pp. 1571-1579, vol. 76, No. 6.

\* cited by examiner

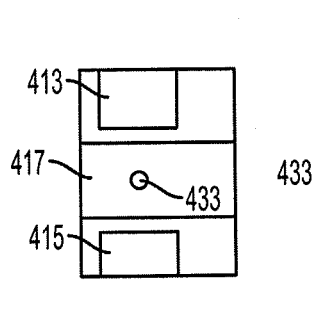 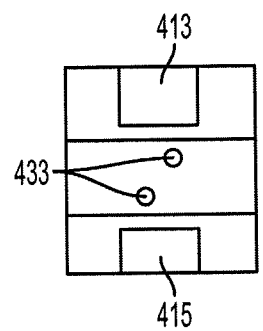 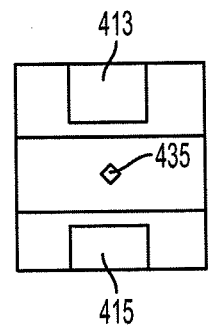
FIG. 4A    FIG. 4B    FIG. 4C
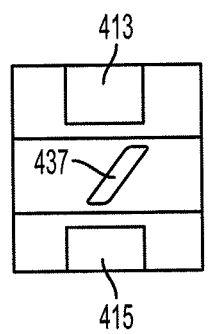 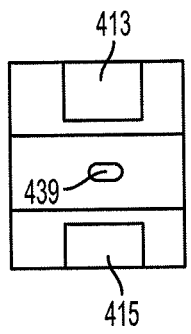 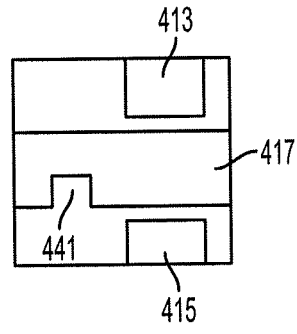
FIG. 4D    FIG. 4E    FIG. 4F

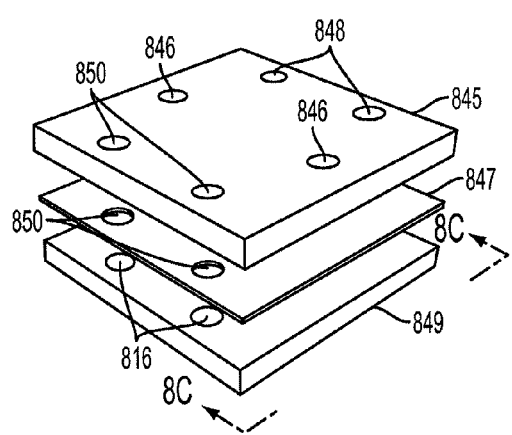
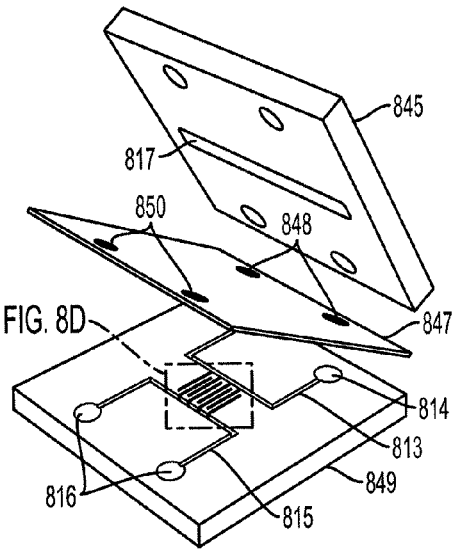
FIG. 8A
FIG. 8B
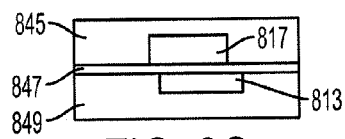
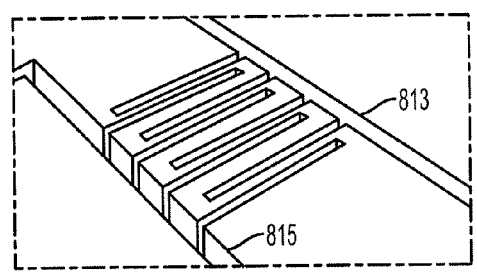
FIG. 8C
FIG. 8D

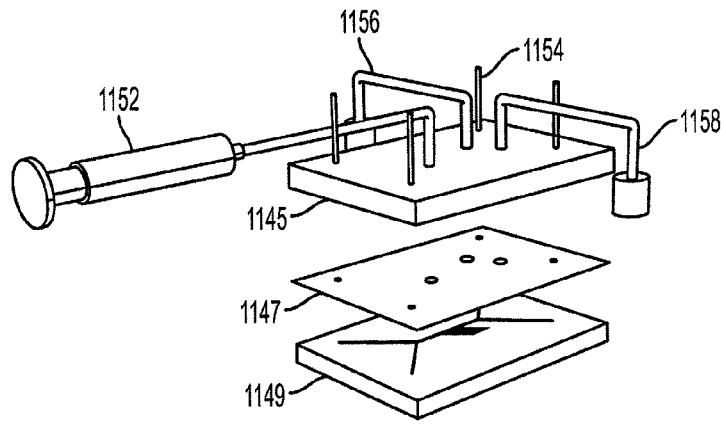
FIG. 11A
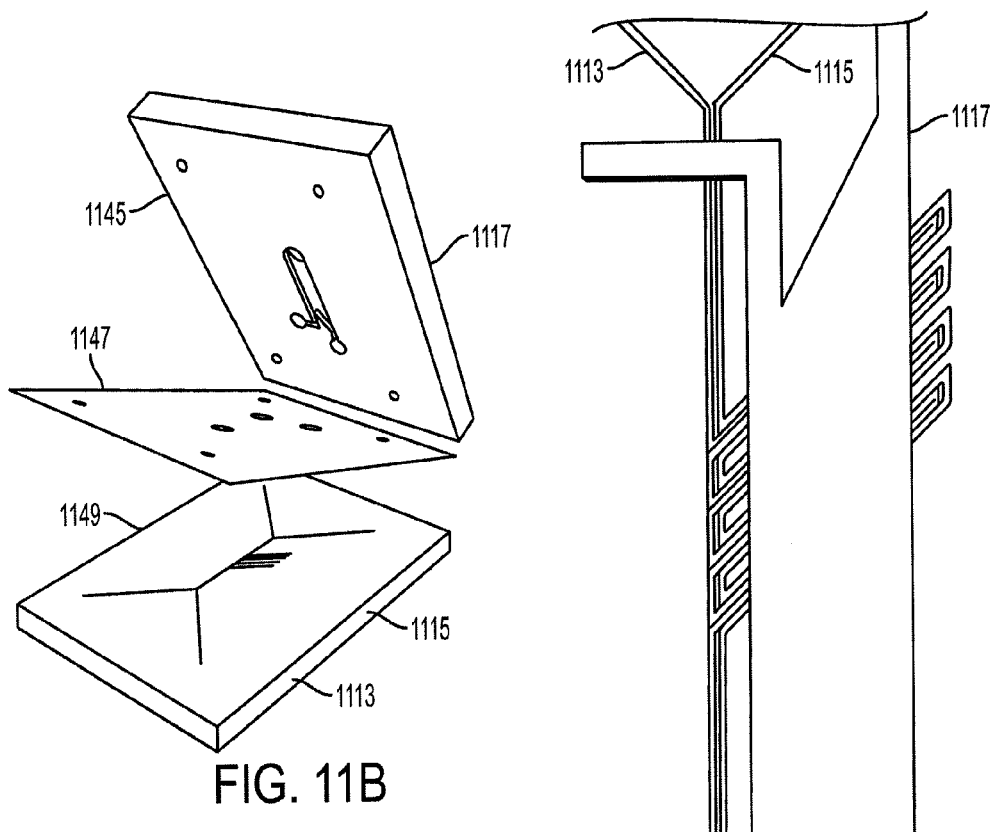
FIG. 11B
FIG. 11C

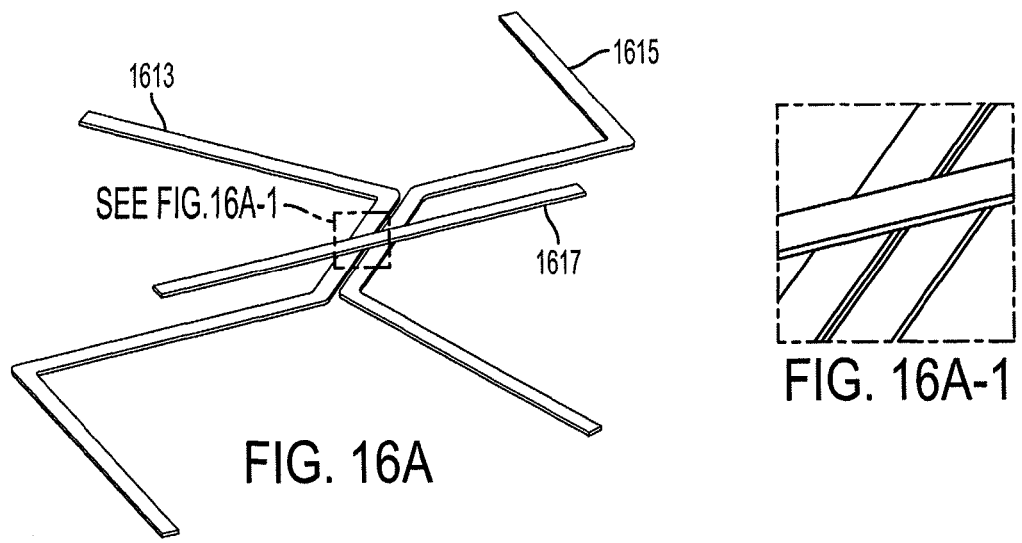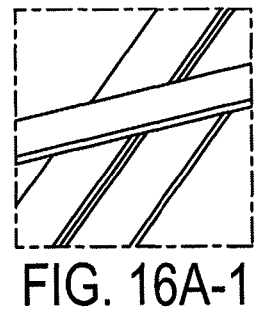
FIG. 16A
FIG. 16A-1
FIG. 16B
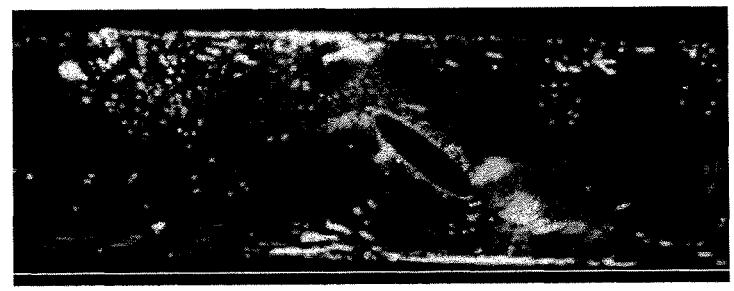
FIG. 16C
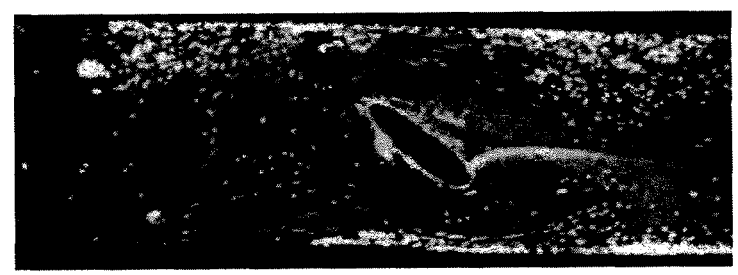
FIG. 16D

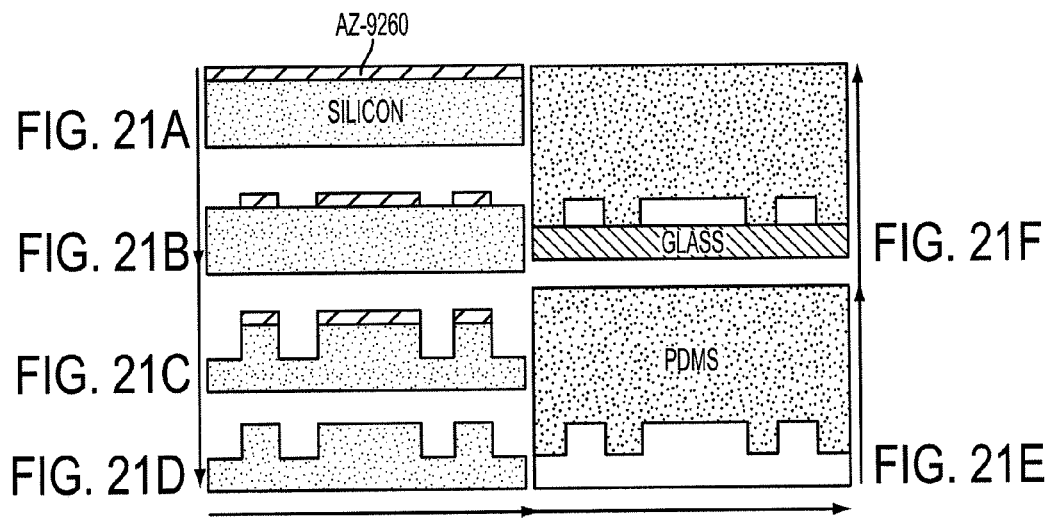
FIG. 21A
FIG. 21B
FIG. 21C
FIG. 21D
FIG. 21E
FIG. 21F
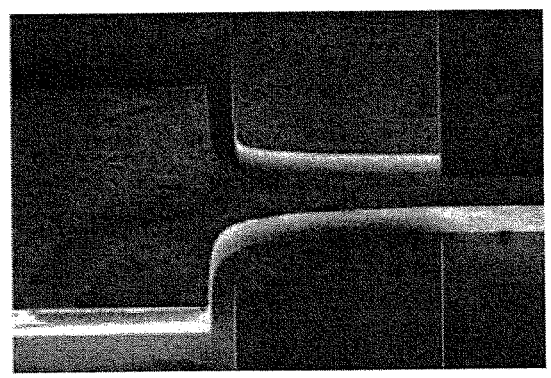
FIG. 21G
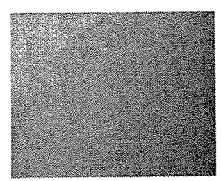 
FIG. 21H  FIG. 21I

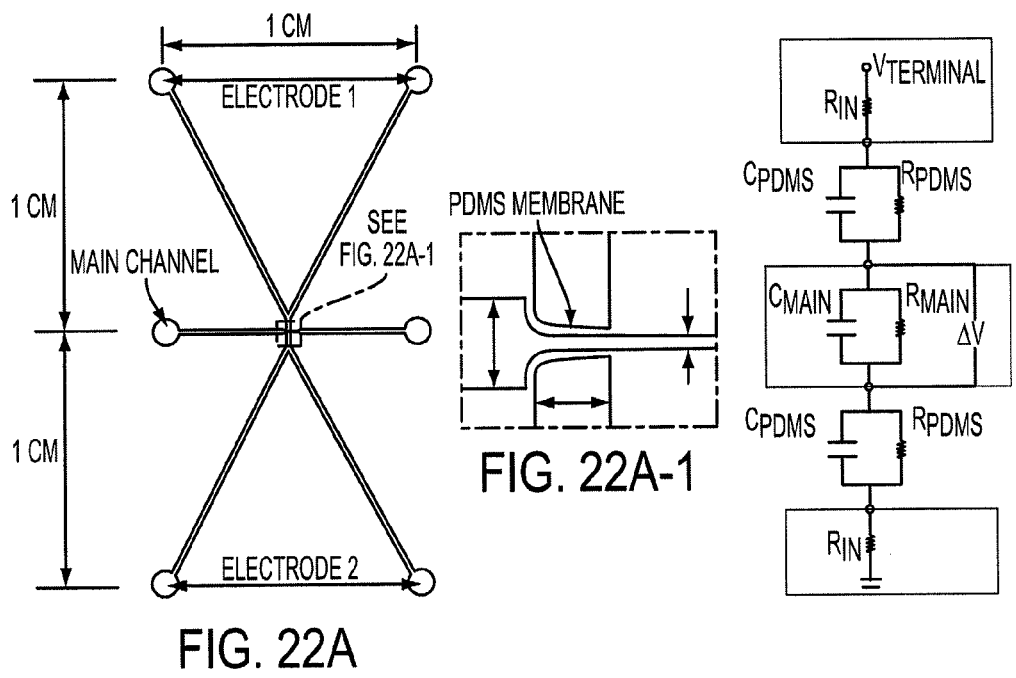
FIG. 22A
FIG. 22A-1
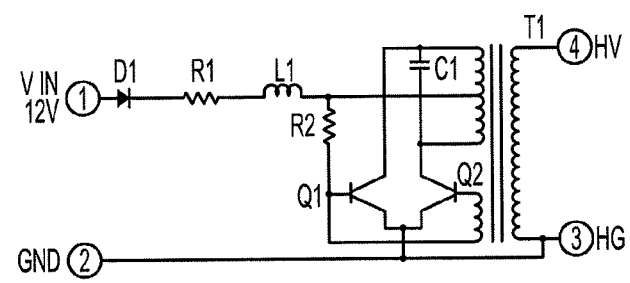
FIG. 22B

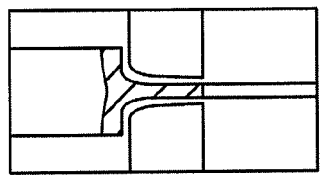 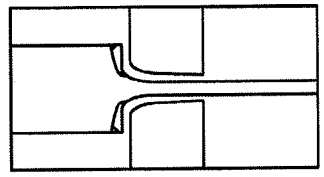 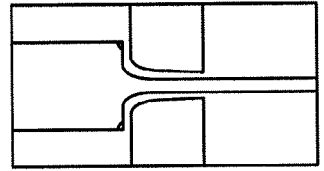
FIG. 24A     FIG. 24B     FIG. 24C
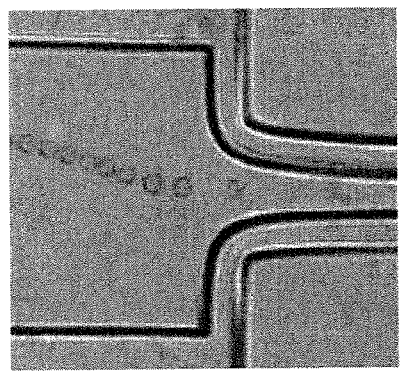 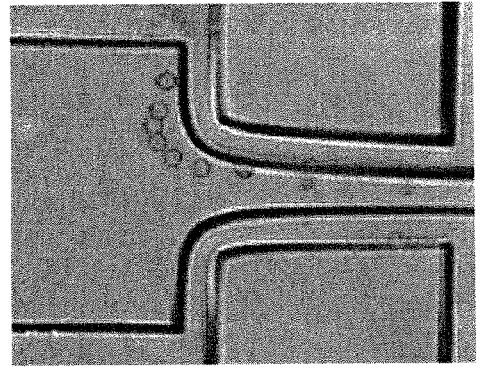
FIG. 25A     FIG. 25B

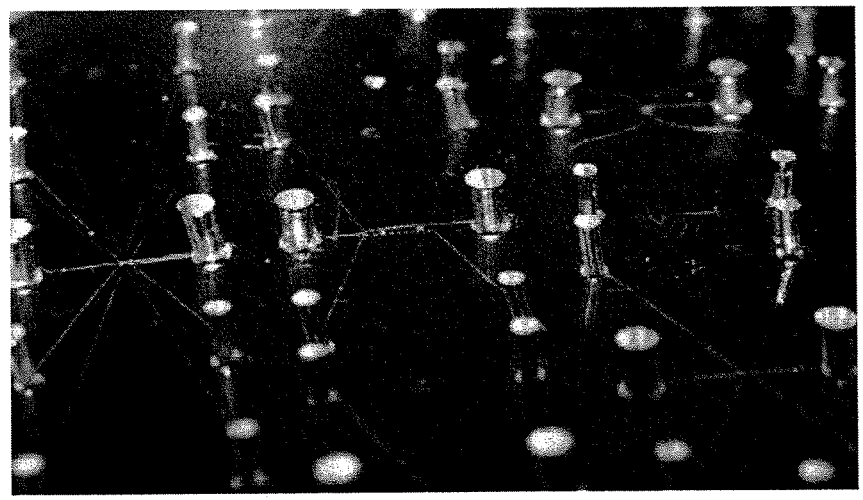
FIG. 35A
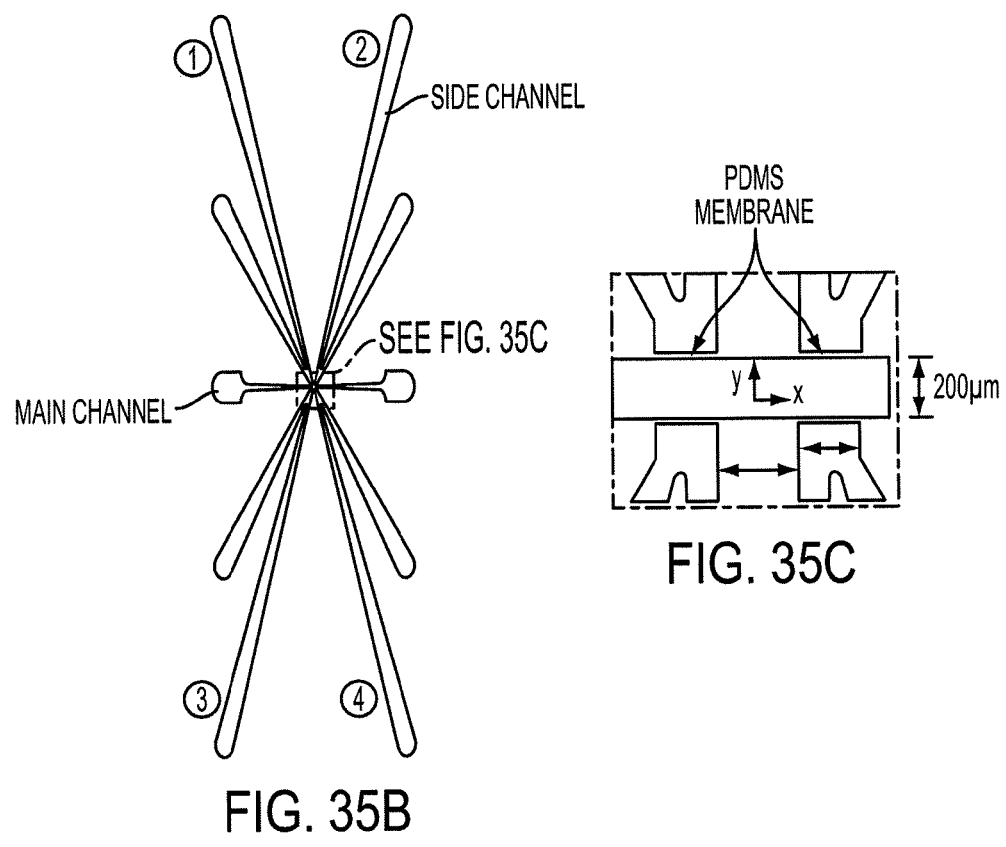
FIG. 35B
FIG. 35C

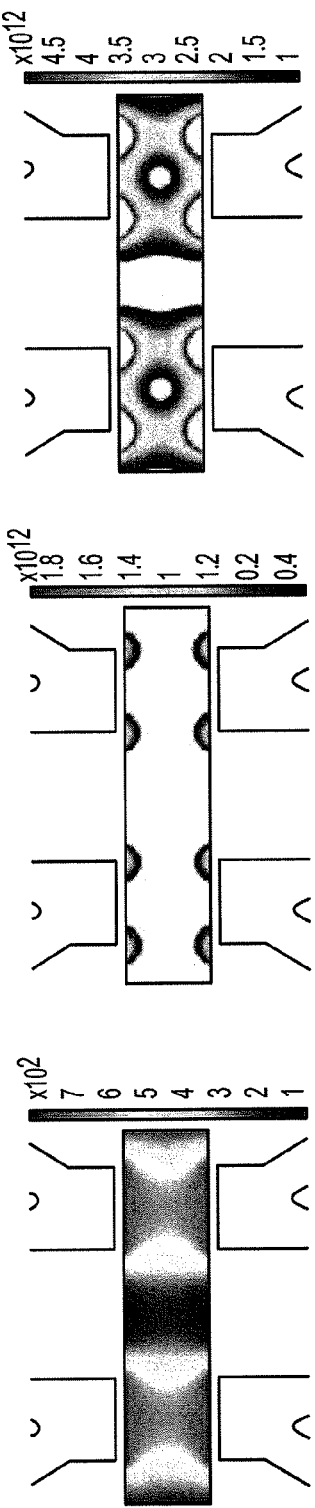
FIG. 36A
FIG. 36B
FIG. 36C
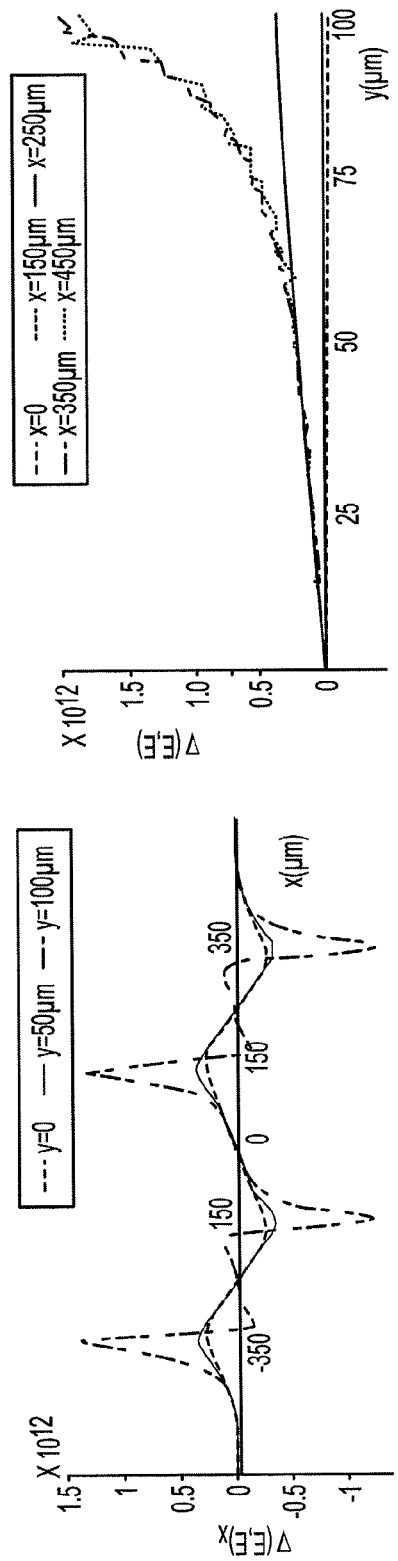
FIG. 37A
FIG. 37B

DEVICES AND METHODS FOR CONTACTLESS DIELECTROPHORESIS FOR CELL OR PARTICLE MANIPULATION

REFERENCE TO RELATED APPLICATIONS

This application claims priority to U.S. Provisional Patent Application 61/158,553, filed Mar. 9, 2009, and U.S. Provisional Patent Application 61/252,942, filed Oct. 19, 2009, the disclosures of both of which are hereby incorporated by reference herein.

FIELD OF THE INVENTION

The present invention relates to devices and methods for contactless dielectrophoresis (DEP) for manipulation of cells or particles. The devices and methods of the present invention provide for the application of DEP in which electrodes are not in direct contact with the subject sample.

BACKGROUND OF THE INVENTION

Isolation and enrichment of cells/micro-particles from a biological sample is one of the first crucial processes in many biomedical and homeland security applications [1]. Water quality analysis to detect viable pathogenic bacterium [2-6] and the isolation of rare circulating tumor cells (CTCs) for early cancer detection [7-19] are important examples of the applications of this process. Conventional methods of cell concentration and separation include centrifugation, filtration, fluorescence activated cell sorting, or optical tweezers. Each of these techniques relies on different cell properties for separation and has intrinsic advantages and disadvantages. For instance, many of the known techniques require the labeling or tagging of cells in order to obtain separation. These more sensitive techniques may require prior knowledge of cell-specific markers and antibodies to prepare target cells for analysis.

Dielectrophoresis (DEP) is the motion of a particle in a suspending medium due to the presence of a non-uniform electric field [28, 29]. DEP utilizes the electrical properties of the cell/particle for separation and identification [29, 30]. The physical and electrical properties of the cell, the conductivity and permittivity of the media, as well as the gradient of the electric field and its applied frequency are substantial parameters determining a cell's DEP response.

The application of dielectrophoresis to separate target cells from a solution has been studied extensively in the last two decades. Examples of the successful use of dielectrophoresis include the separation of human leukemia cells from red blood cells in an isotonic solution [7], entrapment of human breast cancer cells from blood [8], and separation of U937 human monocytic from peripheral blood mononuclear cells (PBMC) [9]. DEP has also been used to separate neuroblastoma cells from HTB glioma cells [9], isolate cervical carcinoma cells [10], isolate K562 human CML cells [11], separate live yeast cells from dead [12], and segregate different human tumor cells [13]. Unfortunately, the microelectrode-based devices used in these experiments are susceptible to electrode fouling and require complicated fabrication procedures [33, 34].

Insulator-based dielectrophoresis (iDEP) has also been employed to concentrate and separate live and dead bacteria for water analysis[2]. In this method, electrodes inserted into a microfluidic channel create an electric field which is distorted by the presence of insulating structures. The devices can be manufactured using simple fabrication techniques and can be mass-produced inexpensively through injection molding or hot embossing[35, 36]. iDEP provides an excellent solution to the complex fabrication required by traditional DEP devices however, it is difficult to utilize for biological fluids which are highly conductive. The challenges that arise include joule heating and bubble formation[37]. In order to mitigate these effects, oftentimes the electrodes are placed in large reservoirs at the channel inlet and outlet. Without an additional channel for the concentrated sample[36], this could re-dilute the sample after it has passed through a concentration region.

While many have had success designing and fabricating different DEP and iDEP microdevices to manipulate particles in biological fluids, there are some potential drawbacks of these techniques. The traditional DEP technique suffers from fouling, contamination, bubble formation near integrated electrodes, low throughput, and an expensive and complicated fabrication process [33, 34]. The insulating obstacles employed by iDEP are meant to address these shortcomings and are less susceptible to fouling than integrated electrodes [38]. The iDEP fabrication process is also much less complicated; the insulating obstacles can be patterned while etching the microchannel in one step. This technique has the added benefit of making the process more economical in that mass fabrication can be facilitated through the use of injection molding. Unfortunately, one of the primary drawbacks of an iDEP system is the presence of a high electric field intensity within the highly conductive biological fluid inside the microchannel [33, 39]. The relatively high electrical current flow in this situation causes joule heating and a dramatic temperature increase. The ideal technique would combine the simple fabrication process of iDEP and resistance to fouling with the reduced susceptibility to joule heating of DEP while preserving the cell manipulation abilities of both methods.

SUMMARY OF THE INVENTION

It is an object of the present invention to provide a dielectrophoresis device having a sample channel which is separated by physical barriers from electrode channels which receive electrodes. The electrodes provide an electric current to the electrode channels, which creates an non-uniform electric field in the sample channel, allowing for the separation and isolation of particles in the sample. As the electrodes are not in contact with the sample, electrode fouling is avoided and sample integrity is better maintained.

It is a further object of the present invention to provide a dielectrophoresis device having a sample channel which is separated by physical barriers from electrode channels which receive electrodes, whereby the sample channel and electrode channels are formed in a single substrate layer and whereby the physical barriers are formed by the substrate itself.

It is a further object of the present invention to provide a dielectrophoresis device having a channel for receiving a sample in a first substrate layer, a first electrode channel and a second electrode channel for receiving electrodes in a second substrate layer and an insulation barrier between the first substrate layer and the second substrate layer.

It is a further object of the present invention to provide a dielectrophoresis device having a first electrode channel for conducting an electric current in a first substrate layer, a channel for receiving a sample in a second substrate layer and a second electrode channel for conducting an electric current in a third substrate layer. The device also has a first insulation barrier between the first substrate layer and the second substrate layer and a second insulation barrier between the second substrate layer and the third substrate layer, preventing the sample from coming in contact with the electrodes.

It is a still further object of the present invention to provide methods for separating particles in solution using a device of the present invention. A sample containing particles is introduced into the sample channel in a manner that causes the sample to flow through the channel and electrical current is applied to the electrodes, creating a non-uniform electric field that affects the movement of the particles to be separated differently than it affects the movement of other particles in the sample. As the particles to be separated move differently, they are separated from other particles in the sample at which point they may be isolated.

There are other objects of the present invention that are provided which are described in further detail below.

DESCRIPTION OF THE DRAWINGS

FIGS. 4A-F show schematics of example variations in insulating structures within the sample channel which may be used in embodiments of the present invention. A single circular structure (FIG. 4A), multiple insulating structures (FIG. 4B), a diamond shaped insulating structure (FIG. 4C), a ridge insulating structure (FIG. 4D), an oval insulating structure (FIG. 4E) and a bump structure (FIG. 4F) are the example embodiments shown.

FIGS. 8A-D show schematics of an embodiment of the three layer device of the present invention. FIGS. 8A and B show the layers of the device. FIG. 8C shows a view of the channels taken along section a-a from FIG. 8A. FIG. 8D shows an exploded view of the box of FIG. 8B.

FIGS. 11A-C show schematics of an embodiment of the three layer device of the present invention for continuous sorting. FIGS. 11A and B show the layers of the device. FIG. 11C shows a top view of the channels. Tilted electrode channels on the bottom layer are separated from the sample channel with a thin dielectric barrier. The electrodes have an angle with respect to the center line of the main channel. The target cells can be continuously manipulated in a specific reservoir in the outlet.

FIG. 16A shows a schematic of an embodiment of a three layer device for trapping particles. FIGS. 16A-1 shows an enlarged view of the dashed box in FIG. 16A. FIGS. 16B-D show images of red blood cells (FIG. 16B) trapped via positive DEP, 4 micron beads (FIG. 16C) trapped via positive DEP, and 1 micron beads (FIG. 16D) trapped via negative DEP.

FIGS. 21A-F show schematics of a fabrication process which may be used in conjunction with the present invention. Steps A through D are followed only once to create a master stamp. Steps E and F are repeated to produce an indefinite number of experimental devices. FIG. 21G shows a SEM image of the silicon wafer mold at the intersection between the side and the main channel of the microfluidic device. FIG. 21H shows an imaging showing the surface roughness of the wafer after growing and removing the oxide layer. FIG. 21I shows an image showing the scalloping effect after DRIE.

FIG. 22A shows a schematic of the microfluidic device of Example 1 and the equivalent circuit model. FIG 22A-1 shows an enlarged view of the dashed box in FIG. 22A. FIG. 22B shows a schematic of the two transistor inverter circuit provided by JKL Components Corp.

FIG. 23 shows numerical results of the electric field gradient within the sample channel.

FIGS. 24A-C show electric field surface plot for an applied AC field at 85 kHz and 250 Vrms. Areas with the induced electric field intensity higher than (A) 0.1 kV/cm, (B) 0.15 kV/cm and (C) 0.2 kV/cm.

FIGS. 25A and B show superimposed images showing the trajectory of one cell through the device. In FIG. 25A the cell is moving from right to left under an applied pressure and in FIG. 25B with an applied voltage of 250 Vrms at 85 KHz. The superimposed images were approximately 250 ms apart.

FIG. 33G shows a SEM image of the silicon wafer mold at the trapping zone. FIG. 33H shows an image of the fabricated device. The main and side channels were filled with dyes to improve imaging.

FIG. 35A shows an image of a PDMS mold from a silicon master stamp containing multiple microfluidic devices as described in Example 3. FIG. 35B shows a two dimensional schematic of the device with straight main channel used in Example 3. The channel depth is 50 µm. FIG. 35C shows an enlarged view of the dashed box in FIG. 35B.

FIG. 36A shows an electric field intensity (V/m) surface plot. FIGS. 36B and C show plots of the gradient of the electric field squared ($v(E \cdot E)$)($kg^2mC^{-2}S^{-4}$) surface plot. V1=V2=70 Vrms at 300 kHz and V3=V4=Ground.

FIGS. 37A and B show numerical results for Example 3: (A) a line plot of the x component of the gradient of the electric field squared ($kg^2mC^{-2}S^{-4}$) along the lines parallel to the center line of the main channel and at different distances from the channel wall for V1=V2=70 Vrms at 300 kHz and V3=V4=Ground boundary condition (y=0, 50, and 100 µm); and (B) a line plot of the y component of the gradient of the electric field squared (kg2mC-2S-4) along the lines perpendicular to the center line of the main channel and at different distances from the origin for V1=V2=70 Vrms at 300 kHz and V3=V4=Ground boundary condition (x=0, 150, 250, 350, and 450 µm).

FIG. 38A shows a plot of the results, while

Figure 42A:
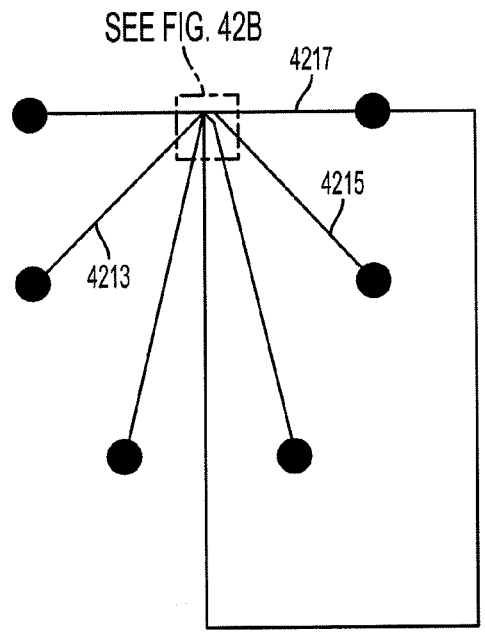
FIGS. 42A and B show schematics of a device designed for continuous separation of particles as is described in Example 4, with FIG. 42B showing an exploded view of the box in FIG.
Figure 42B:
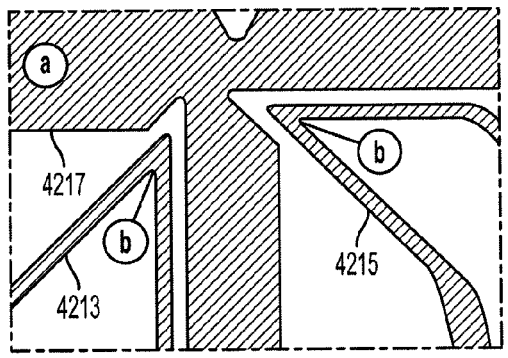
Figure 42C:
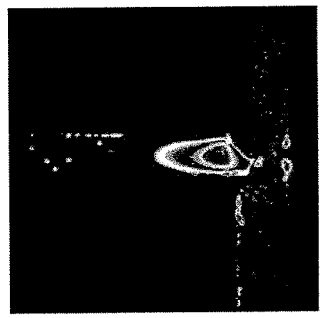
Figure 42D:
Figure 42E:
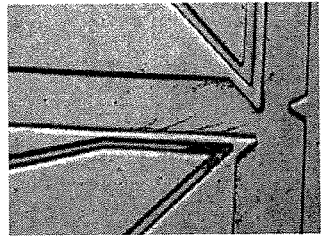

42A. Particles are driven through the sample channel while an electric signal is applied across the fluid electrode channels. Four micron beads are continuously separated from 2 micron beads and released, as is shown in the images of FIGS. 42C and D. Red blood cells are isolated from buffer solution, as is shown in the image of FIG. 42E.

DETAILED DESCRIPTION OF THE INVENTION

The present invention provides methods, devices, and systems to manipulate micro-particles suspended in biological fluids using their electrical signatures without direct contact between the electrodes and the sample. Contactless dielectrophoresis (cDEP) employs the simplified fabrication processes of iDEP yet lacks the problems associated with the electrode-sample contact [40].

cDEP relies upon reservoirs filled with highly conductive fluid to act as electrodes and provide the necessary electric field. These reservoirs are placed adjacent to the main microfluidic channel and are separated from the sample by a thin barrier of a dielectric material. The application of a high-frequency electric field to the electrode reservoirs causes their capacitive coupling to the main channel and an electric field is induced across the sample fluid.

Similar to traditional DEP, cDEP may exploit the varying geometry of the electrodes to create spatial non-uniformities in the electric field. However, by utilizing reservoirs filled with a highly conductive solution, rather than a separate thin film array, the electrode structures employed by cDEP can be fabricated in the same step as the rest of the device; hence the process is conducive to mass production [40]. The various embodiments of the present invention provide devices and methods for performing cDEP, as well as methods for fabricating cDEP devices.

In general, the present invention provides devices and methods that allow cell sorting to identify, isolate or otherwise enrich cells of interest based on electrical and physical properties. An electric field is induced in a main sorting microchannel using electrodes inserted in a highly conductive solution which is isolated from the microchannel by thin insulating barriers. The insulating barriers exhibit a capacitive behavior and an electric field is produced in the isolated microchannel by applying an AC electric field. Electrodes do not come into contact with the sample fluid inside the microchannel, so that electrolysis, bubble formation, fouling and contamination is reduced or eliminated. In addition, the electric field is focused in a confined region and has a much lower intensity than that found in traditional insulator-based dielectrophoresis, so heating within the sample channel is negligible and the likelihood of cell lysis is greatly reduced. The system can also be used for characterizing and sorting micro- or nanoparticles.

Methods

In one embodiment, the present invention provides a method to induce DEP to manipulate cells or micro/nano particles without direct physical contact between the electrodes and the sample solution with a simplified and inexpensive micro-fabrication process. Further examples of manipulation of cells and micro/nano particles are given below.

In another embodiment, the present invention provides a method to induce an electric ac field without direct physical contact between the electrodes and the sample solution with a simplified and inexpensive micro-fabrication process.

In another embodiment, the present invention provides a method whereby cDEP can be used to measure the current through a system and measure the electrical resistance/impedance of a system for detection purposes. cDEP electrodes can be placed on an object to deliver a known amount of electrical current though the object. By measuring the electric potential at different places on the object, the electrical impedance of the object can be calculated. In this embodiment, the electrical impedance may be measured so that it is possible to determine when a certain number of particles are trapped or isolated. Once the requisite number of particles are trapped, e.g. the number required for downstream analysis, the impedance will reach a pre-set level and the current can be turned off, allowing the particles to be released.

In another embodiment of the present invention, cDEP can be used as a non-invasive method to monitor living animal cells in vitro. The cells are grown on an insulating thin barrier. The electrode channels are under this thin barrier. The impedance of the cultured cells on the insulating barrier is measured at one specific frequency as a function of time. Because of the insulating properties of the cell membrane, the impedance of the system increases with increasing the number of cells on the surface. The 3D geometrical changes of layered cells on the surface can be monitored because the current through the layers of cells and around the cells changes due to the shape change of the cells.

In another embodiment of the present invention, methods are provided whereby cDEP can be used to measure the dielectric properties of a medium as a function of frequency. The impedance of a electrochemical system is measured for different frequencies to characterize the response of the system as a function of frequency In another embodiment of the present invention, cDEP devices can be designed to provide methods for measuring small changes in electrical resistance of the chest, calf or other regions of the body without direct electrode-body contact to monitor blood volume changes. These methods can indirectly indicate the presence or absence of venous thrombosis and provide an alternative to venography, which is invasive and requires a great deal of skill to execute adequately and interpret accurately.

In yet another embodiment of the present invention, cDEP devices may be used for solution exchange and purification of particles. As a non-limiting example, once the particles of interest are captured in a device, the inlet solution may be change to a solution different from that of the sample, for example a buffer. The particles may be released into the buffer. As a non-limiting example, cancer cells may be concentrated from a blood sample in the device. The inlet solution may then be changed to a suitable buffer, allowing the cancer cells to be purified and concentrated from blood and suspended in the buffer.

In still another embodiment of the present invention, cDEP devices may be designed to have two (or more) solutions traveling side by side using laminar flow as is known in the art. Changes in the electrical field of the device may then be used to move particles back and forth between the two flows as is necessary. The two flows may then later be separated so that particles are isolated as desired.

The methods of the present invention may involve any DEP device engineered so that there is no direct physical contact between the electrodes and the sample solution. Exemplary, but non-limiting, examples of such devices are given in this specification.

Device Designs

Non-limiting examples of cDEP device designs are presented herein. Some examples are illustrated in the figures, where like numbering may be used to refer to like elements in different figures (e.g. element 117 in FIG. 1 may have a similar function to element 217 in FIG. 2). The objects and elements shown in a single figure may or may not all be present in one device. The present invention contemplates any DEP device engineered so that there is no direct physical contact between the electrodes and the sample solution, and there will be modifications of the examples set forth herein that will be apparent to one of skill in the art.

One Layer (2D) Designs

In certain embodiments of the invention, a device is provided where the main and side (electrode) channels are fabricated in one layer of the device. The second layer is an insulating layer such as glass or polydimethylsiloxane (PDMS) to bond the microfluidic channels.

Figure 1A:
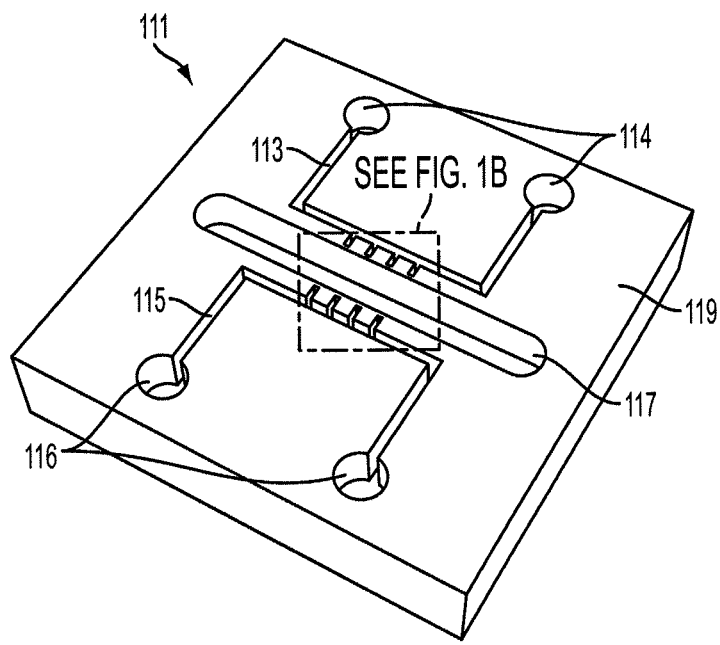
FIGS. 1A and B show a three dimensional schematic of a two layer design embodiment of the present invention. The side channels and the main channel are fabricated in one layer.
Figure 1B:
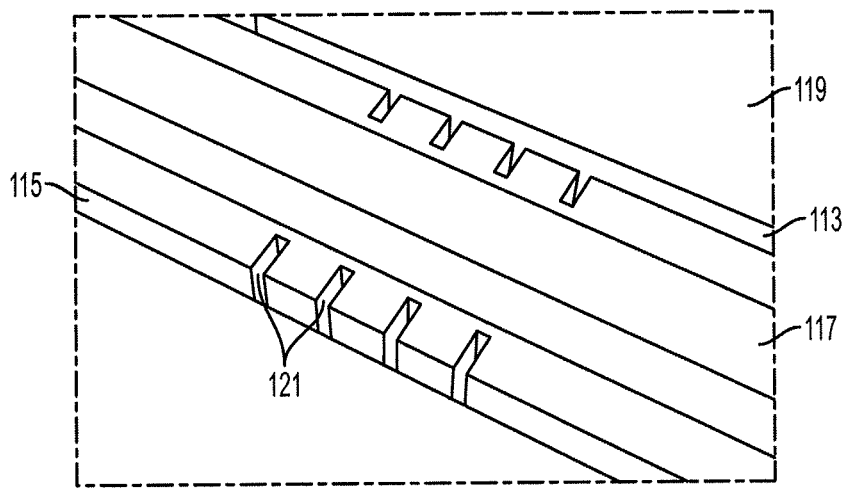
FIG. 1B shows and exploded view of the box in FIG. 1A.

FIG. 1A shows a 3D schematic example of a 2D cDEP device 111 with the main and side channels fabricated in one layer. Side channel electrodes 113, 115 and the main sample channel 117 are fabricated in a single substrate layer 119. FIG. 1B shows an exploded view of the box in FIG. 1A, where notches 121 in the electrode channels 113, 115 can be seen. The electrode channels have portions of receiving electrodes 114, 116, which are shown as circular but may be different shapes depending on the electrode to be received. It is further contemplated that the electrode channels need not have specially shaped portions for receiving an electrode, as the electrode can simply be contacted with the conductive solution in the channel.

There are many factors affecting the performance of single- and multi-layer devices. These factors include the electrode channel geometry, insulating barrier thickness, insulating barrier geometry, insulating structures within the sample channel, sample channel width, sample channel depth, distance between electrodes, and number of electrodes. These factors may be modified to customize the electric fields inducing DEP.

Figure 2A:
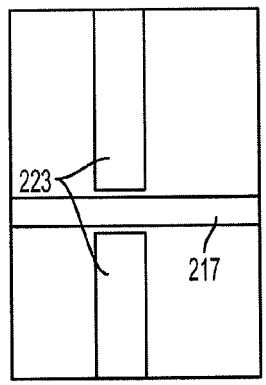
FIGS. 2A-C show schematics of example electrode channel geometries which may be used in embodiments of the present invention. Square (FIG. 2A), rounded (FIG. 2B), and saw-tooth (FIG. 2C) are some examples of electrode geometries which may be used in embodiments of the present invention.
Figure 2B:
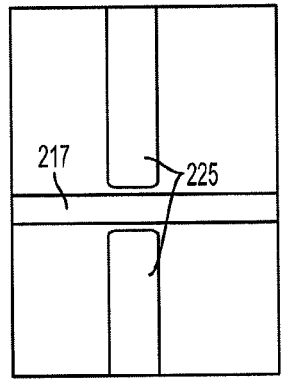
Figure 2C:
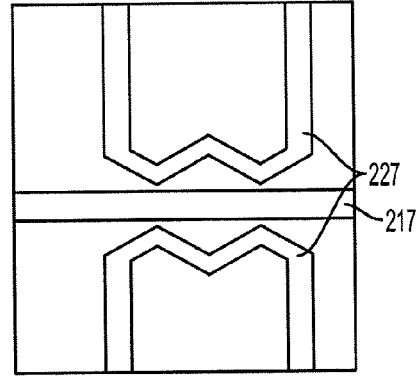

The electrode channels may have a variety of shapes and sizes which enhance the performance of single- and multi-layer devices. Example shapes include: square or rectangular electrodes, rounded squares or rectangles (radius of curve additionally effects performance), saw-tooth shapes, combinations of these shapes or any geometric change to the electrode channel. For the purposes of the invention, symmetry is not required and asymmetry can alter the performance of the device. Examples of rectangular electrodes 223 (FIG. 2A), rounded rectangular electrodes 225 (FIG. 2B) and saw tooth shaped electrodes 227 (FIG. 2C) on either side of sample channels 217 are shown in FIG. 2. It should be apparent that other rectangular, rounded rectangular and saw-tooth shaped electrodes are contemplated by the present invention and that the embodiments in FIG. 2 are exemplary only.

Insulating barrier thickness is the thickness of the insulating material which separates the electrode channels and the sample channel. The thickness of the insulating barrier can change the performance of the device. In certain embodiments, these thicknesses can vary between about 0.01 micron and about 10 mm, and are preferably between about 1 micron and about 1000 micron. It is contemplated that each electrode channel may have a different insulating barrier thickness.

Figure 3A:
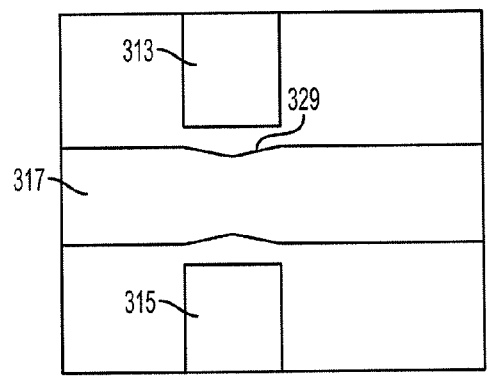
FIGS. 3A and B show schematics of example embodiments with variations in insulating barrier geometries in which the barrier thickness (FIG. 3A) increases and decreases (FIG. 3B).
Figure 3B:
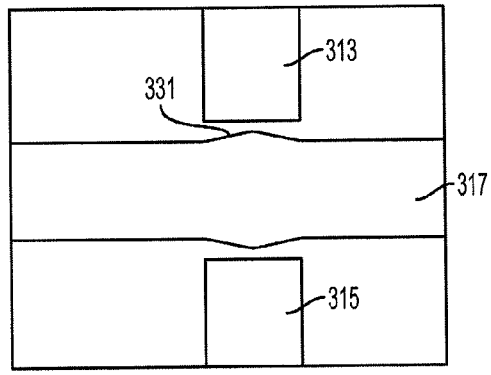

The geometry of the insulating barriers may change the performance of the device. Some contemplated variations include: straight barriers, increases or decreases in barrier thickness along the length (FIG. 3), rounded barriers, barriers which become thicker or thinner along the depth of the channel and combinations of these variations. As is shown in FIG. 3, certain embodiments of devices of the present invention may have areas where the thickness of the insulation barrier increases 329 (FIG. 3A) or where the thickness of the insulation barrier decreases 331 (FIG. 3B).

It is further contemplated that insulating structures may be present in the sample channel or the electrode channels to affect the electrical field. The insulating structures may consist of many different shapes and sizes, including: round or cylindrical pillars, ridges or shelves which split the channel, bumps or slope changes along the channel walls or floors and other geometric changes within the channel (see FIGS. 4 and 7).

FIG. 4 shows non-limiting examples of insulating structures which may be used in the devices of the present invention: a single round post 433 (FIG. 4A), double round posts 433 (FIG. 4B), square posts 435 (FIG. 4C), angled shapes 437 (FIG. 4D), rounded rectangles 439 (FIG. 4E) and extensions of the insulating barrier into the sample channel 441 (FIG. 4F). It will be apparent to one of skill in the art that there are extensive variations on the embodiments shown in FIG. 4 that fall within the scope of the present invention.

The sample channel width may change the performance of the device. In certain embodiments, this width may vary between about 1 micron and about 10 cm, and is preferably between about 10 micron and about 1000 micron.

The sample channel depth may also change the performance of the device. In certain embodiments, this depth may vary between about 1 micron and about 10 cm, and is preferably between about 10 micron and about 1000 micron.

Figures 5A, 5B, 5C, 5D:
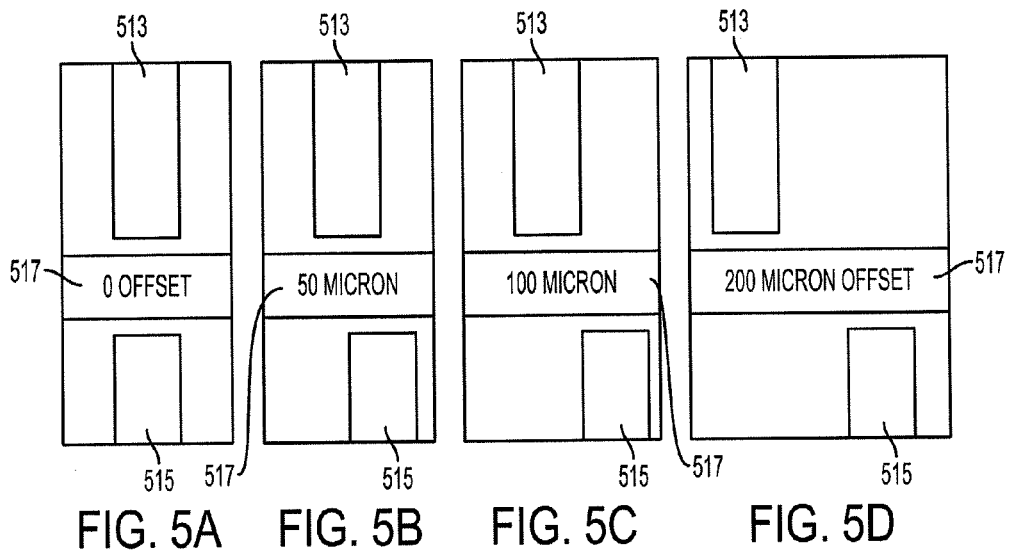
FIGS. 5A-D show schematics of example variations of electrode offset when a single layer device has two electrodes on opposite sides of the sample channel.
Figure 5E:
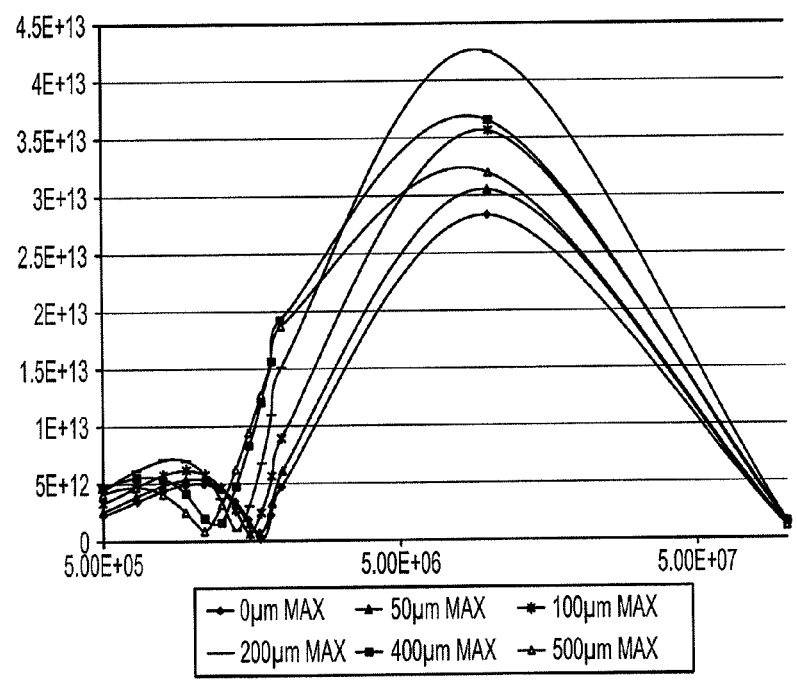
FIG. 5E is a plot of calculated gradient of electric field along the center of the sample channel for the various electrode offsets.
Figure 6A:
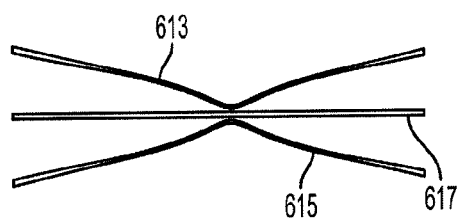
FIGS. 6A-K show schematics of other embodiments of two layer device designs which may be implemented in embodiments of the present invention.
Figure 6B:
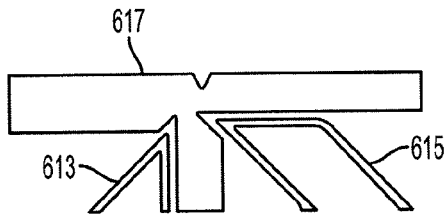
Figure 6C:
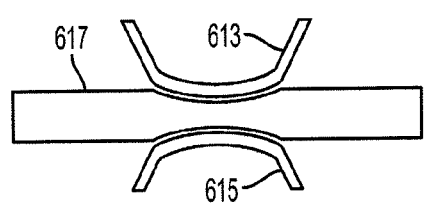
Figure 6D:
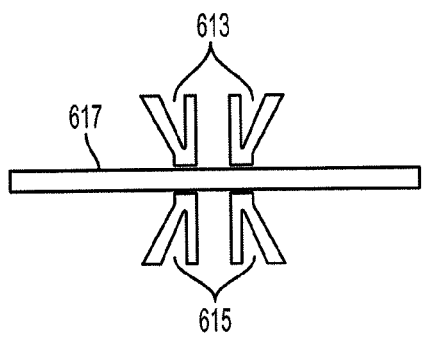
Figure 6E:
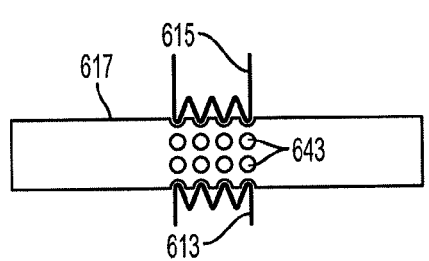
Figure 6F:
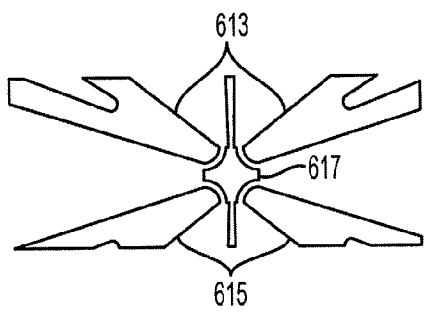
Figure 6G:
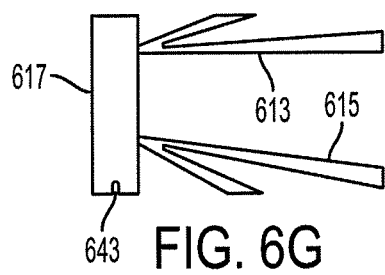
Figure 6H:
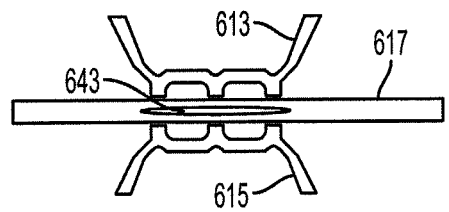
Figure 6I:
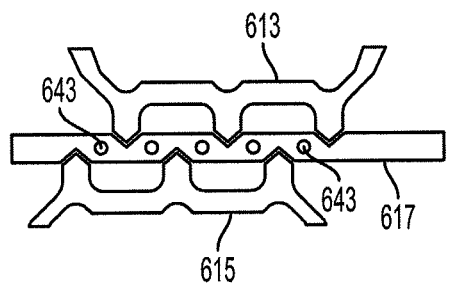
Figure 6J:
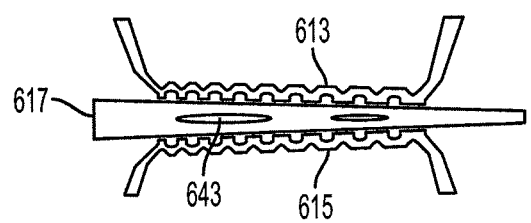
Figure 6K:
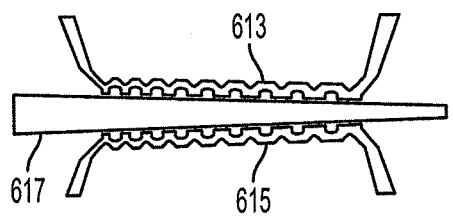
Figure 7A:
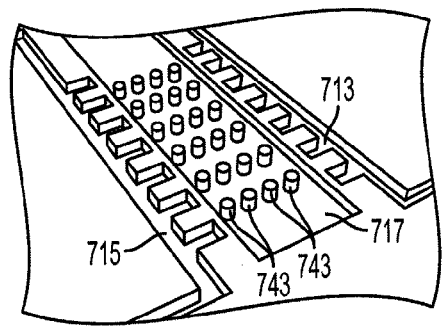
FIGS. 7A-H show schematics of other embodiments of two layer device designs with insulating structures or ridges inside and outside of the main channel.
Figure 7B:
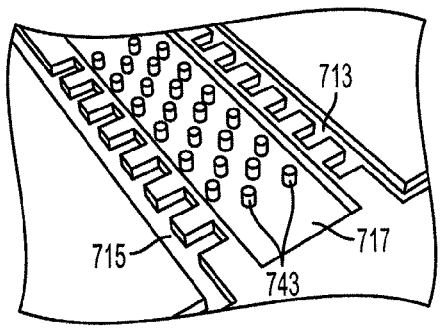
Figure 7C:
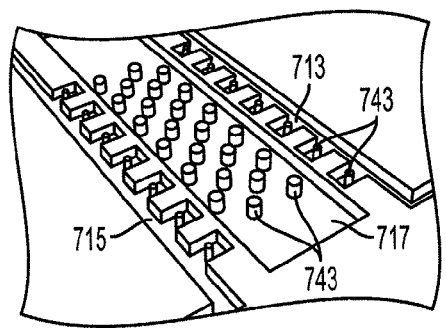
Figure 7D:
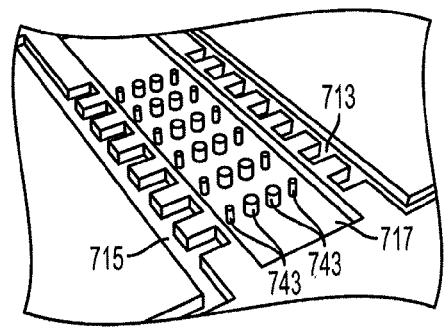
Figure 7E:
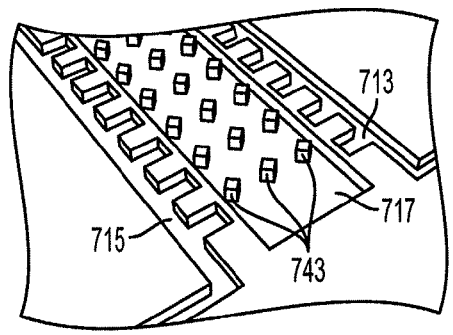
Figure 7F:
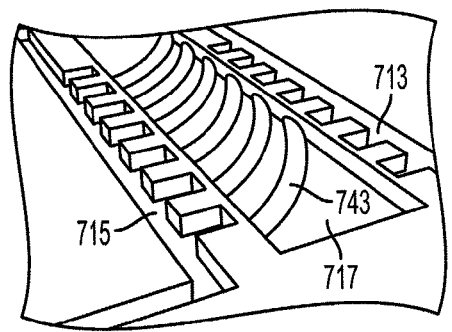
Figure 7G:
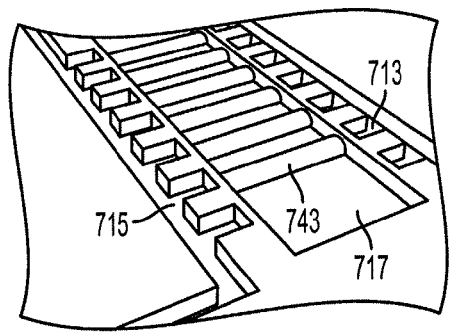
Figure 7H:
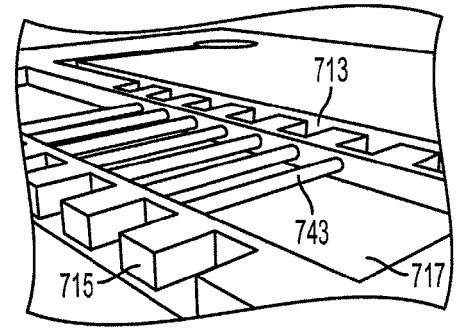
Figure 9A:
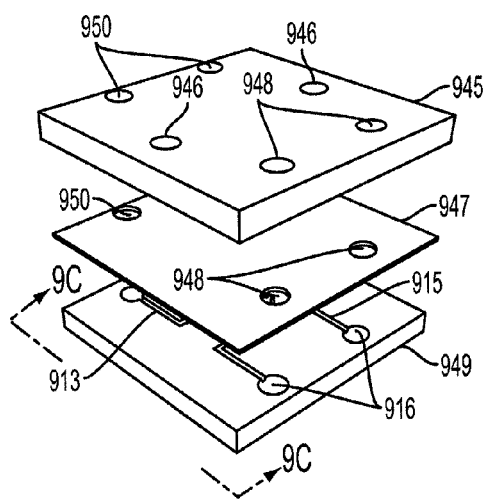
FIGS. 9A-D show schematics of an embodiment of the three layer device of the present invention. Panels A-D have the same views as are described for FIG. 8.
Figure 9B:
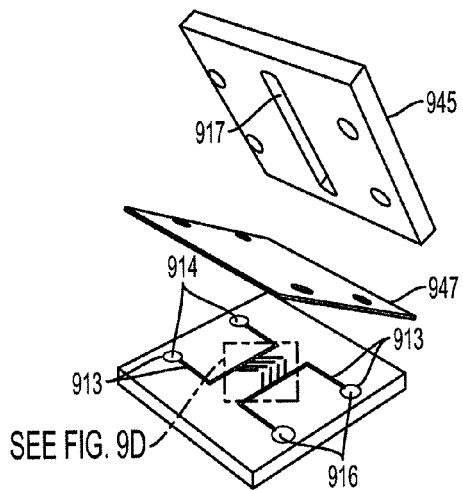
Figure 9C:
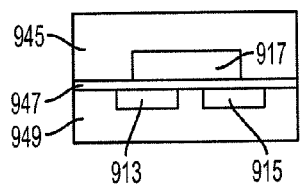
Figure 9D:
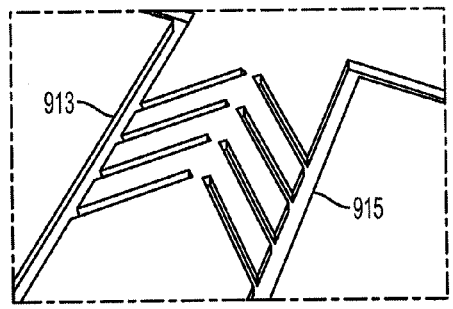
Figure 10A:
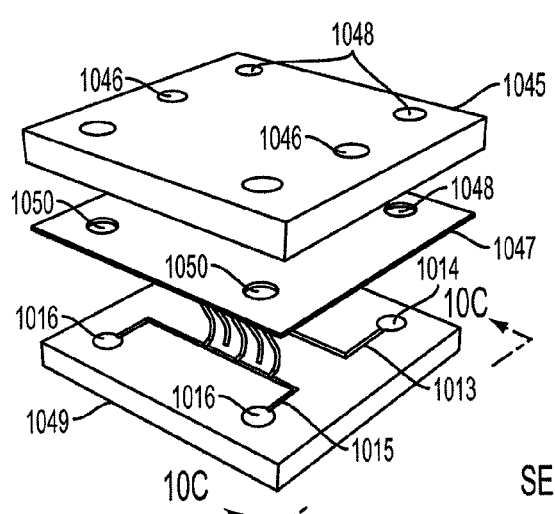
FIGS. 10A-D show schematics of an embodiment of the three layer device of the present invention. Panels A-D have the same views as are described for FIG. 8.
Figure 10B:
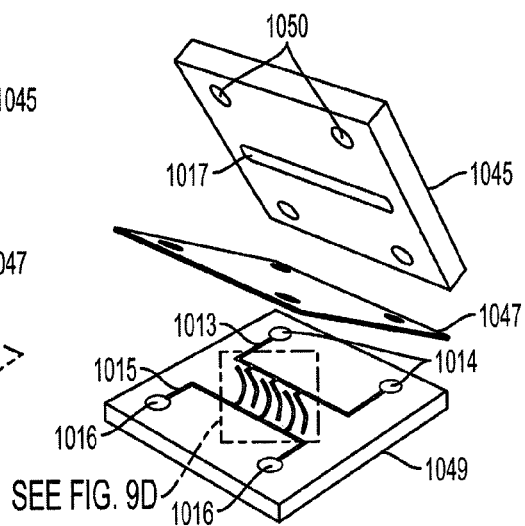
Figure 10C:
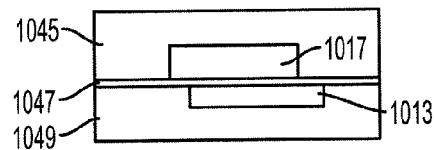
Figure 10D:
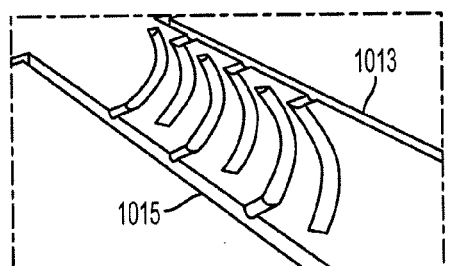

Electrode offset, or the distance between electrodes is another design factor which may change the performance of the device. In certain embodiments, this offset may vary between no offset and about 10 cm offset, but is ideally between 0 micron and about 1 mm. The effects of this offset can be seen in FIG. 5 which shows electrode offsets of 0 micron (FIG. 5A), 50 micron (FIG. 5B), 100 micron (FIG. 5C) and 200 micron (FIG. 5D). As is shown in the plot of FIG. 5E, the calculated gradient of electric field along the center of the sample channel increases as the offset is increased from 0 microns to 200 microns. Above this offset, the electric field gradient decreases. It should be noted that this behavior is for the design with a 100 micron sample, 20 micron barriers, and 100 micron wide electrode channels. As will be apparent to one of skill in the art, different geometries will have different responses to offsets.

It will be apparent to one of skill in the art that many other cDEP devices with different geometries and strategies to manipulate micro-particles fall within the scope of the present invention. Additional, non-limiting embodiments of 2D devices of the present invention are shown in FIG. 6A-K, with sample channels 617, electrodes 613, 615 and insulating structures 643 as illustrated.

The insulating structures and ridges inside and outside of the main channel can be used to enhance the cDEP effect. cDEP separation of micro/nano-particles strongly depends on the geometry of these structures. In certain embodiments, insulating structures within the sample channel may consist of many different shapes and sizes, including: round or cylindrical pillars, ridges or shelves which split the channel, bumps or slope changes along the channel walls or floors and other geometric changes within the sample channel. It is also contemplated that on or both of the electrode channels may have insulating structures.

Non-limiting examples of different cDEP devices showing different strategies to use these insulating structures inside and outside of the main channels are shown in FIGS. 7 A-H, with sample channels 717, electrodes 713, 715 and insulating structures 743 as illustrated. FIG. 7C shows an embodiment with insulating structures in the sample channel and the electrode channels.

Three Layer Designs

In other embodiments of the invention, the main channel and the electrode channels are fabricated in two separate insulating layers. The third layer is a thin insulating barrier separating the other two layers. In certain embodiments, the insulating barrier is made from poly(methyl methacrylate) (PMMA). In other embodiments of the invention, the insulating barrier is made from plastic, silicon, glass, polycarbonate, or polyimide, such as the polyimide film KAPTON produced by Dow Chemical (Midland Mich.). Specific, non-limiting examples include silicon oxide, silicon nitride and polyethylene. The geometry, shape, and position of the bottom or top electrode channels are important parameters in cell/microparticle manipulation. Four non-limiting examples of such designs are shown in FIGS. 8-11.

FIGS. 8-10 show embodiments of three layer devices of the present invention, with panels A and B of each figure showing view of the layers of the device, panel C showing a view of the overlap of the channels along section a-a of panel A and panel D showing an exploded view of the boxed area of panel B. As is shown in FIG. 8, the sample channel is fabricated in the sample channel layer 845, while the electrode channels 813, 815 are fabricated in the electrode channel layer 849. The insulating barrier 847 separates the sample channel layer 845 and electrode channel layer 849. As is shown in the embodiment of FIG. 8, the sample channel layer 845 has holes for accessing the sample channel 846 as well as holes for receiving electrodes 848, 850. Holes for receiving electrodes 848, 850 are also present in the insulating barrier 847 so that the electrodes may make contact with the electrode receiving portions 814, 816 of the electrode channels 813, 815. FIGS. 9 and 10 show other embodiments with like numbering representing like elements.

FIGS. 11A-C show a schematic of a three layer device with electrode channels 1113, 1115 on the bottom substrate layer 1149 and the sample channel 1117 on the top substrate layer 1145. A syringe pump 1152 is used in the embodiment of FIG. 11 for injecting the sample into the sample channel. The electrode channels 1113, 1115 and the sample channel 1117 are separated with a thin insulating barrier 1147. The angle between the electrode channels 1113, 1115 and the sample channel 1117 can be adjusted between 0 to 90 degree. These tilted electrode channels 1113, 1115 manipulate the cells or micro-particles towards the sides of the sample channel 1117 such that the target particles along the side of the sample channel 1117 can be collected in a separate reservoir. As is shown in FIG. 11A, target particles may be separated and isolated in a target reservoir 1156, while the remaining particles in the sample flow into the normal reservoir 1158. FIG. 11C shows the top view of just the sample channel 1117 and the electrode channels 1113, 1115 for the device shown in FIG. 11A.

Five Layer Designs

Figure 12C:
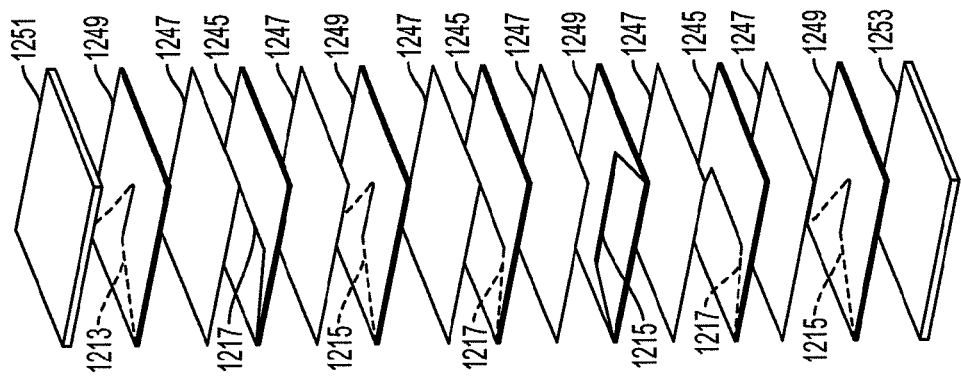
FIG. 12C shows a schematic of an embodiment of a multiple layer device of the present invention.
Figure 12B:
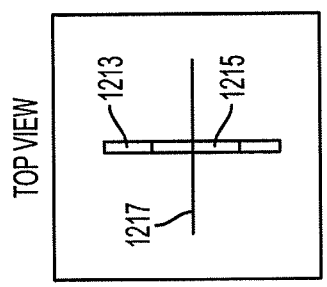
FIG. 12B shows a schematic of a top view of the embodiment of FIG. 12A.
Figure 12A:
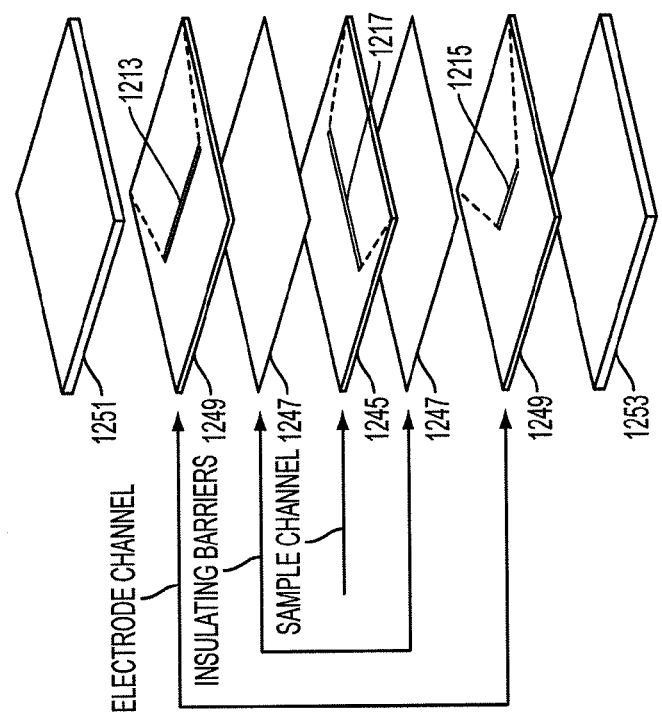
FIG. 12A shows a schematic of an embodiment of a five layer device of the present invention.

In other embodiments of the invention, a five layer device may be used. These designs have a sample channel with electrodes above and below it. A thin membrane above and below the sample channel isolate it from the electrode channels. An non-limiting example of this embodiment can be seen in FIG. 12A. The embodiment shown in FIG. 12A has a top cover 1251, an electrode channel layer 1249 with an electrode channel 1213, an insulating layer 1247, a sample channel layer 1245 with a sample channel 1217, an insulating layer 1247, an electrode channel layer 1249 with an electrode channel 1215 and a bottom cover 1253. FIG. 12B shows a schematic representing a top view of the device shown in FIG. 12A, with the overlapping electrode channels 1213, 1215 and the sample channel 1217 shown.

Multiple Layers

In other embodiments of the present invention there are provided multiple layer cDEP devices. These designs consist of multiple sample channels within one device. They may be organized in layers as: electrode-barrier-sample-barrier-electrode barrier-sample-barrier, with the pattern repeating. Those skilled in the art of fabrication will be able to create devices with upward of 10 sample channels in a single device. An example of this configuration with three sample channels can be seen in FIG. 12C. FIG. 12C shows alternating electrode layers 1249 containing an electrode 1213 or 1215, insulating layers 1247, and sample channel layers 1245 containing a sample channel 1217. The layers are sandwiched between a top cover 1251 and a bottom cover 1253.

Other Embodiments

Figure 13:
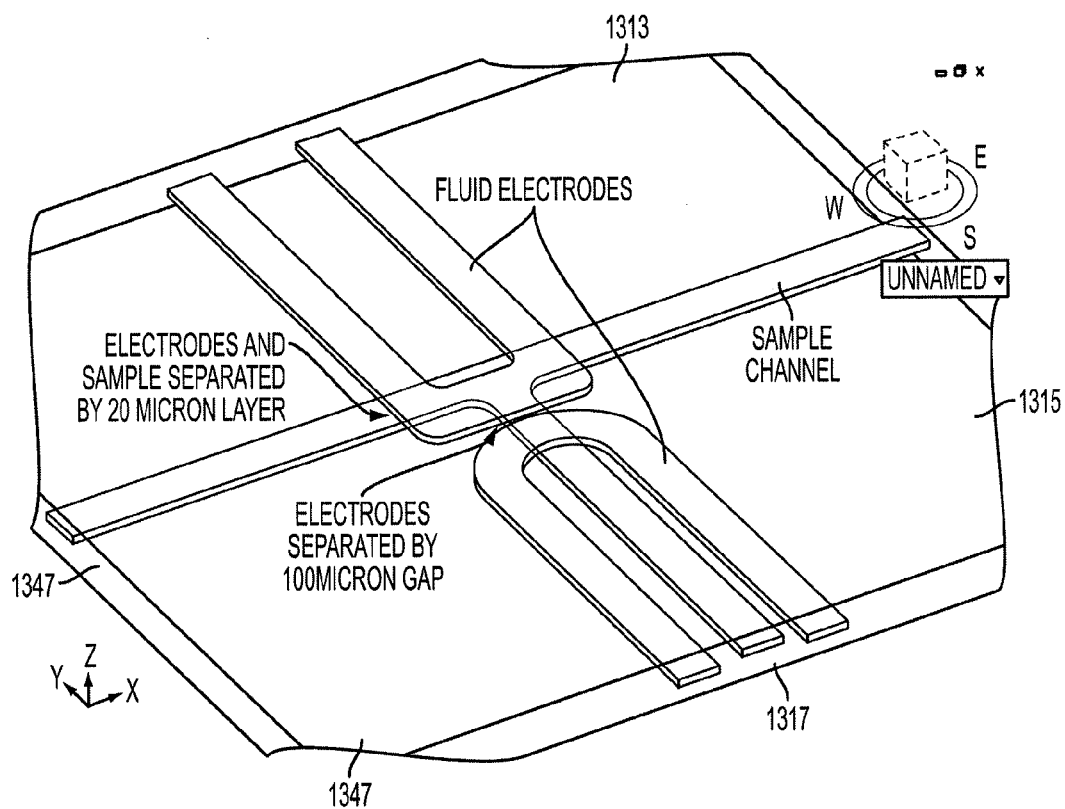
FIG. 13 shows a schematic of an embodiment of a device for continuous sorting having two differently shaped electrodes.

The embodiment depicted in FIG. 13 is a three layer device. Both electrodes 1313, 1315 are located in the same layer. They are separated from the sample channel 1317 by an insulating layer 1347. The entire device is encased within a non-conducting case, which is not shown. In this device, particles traveling in the straight part of the sample channel (the part of the sample channel parallel to the gap between electrodes) will be diverted by dielectrophoretic forces. Particles with specific electrical properties will be diverted into the T-section of the sample channel (the part of the sample channel perpendicular to the gap between electrodes) while others continue straight. Devices of this nature will continuously sort particles as they flow through the device.

Figure 14:
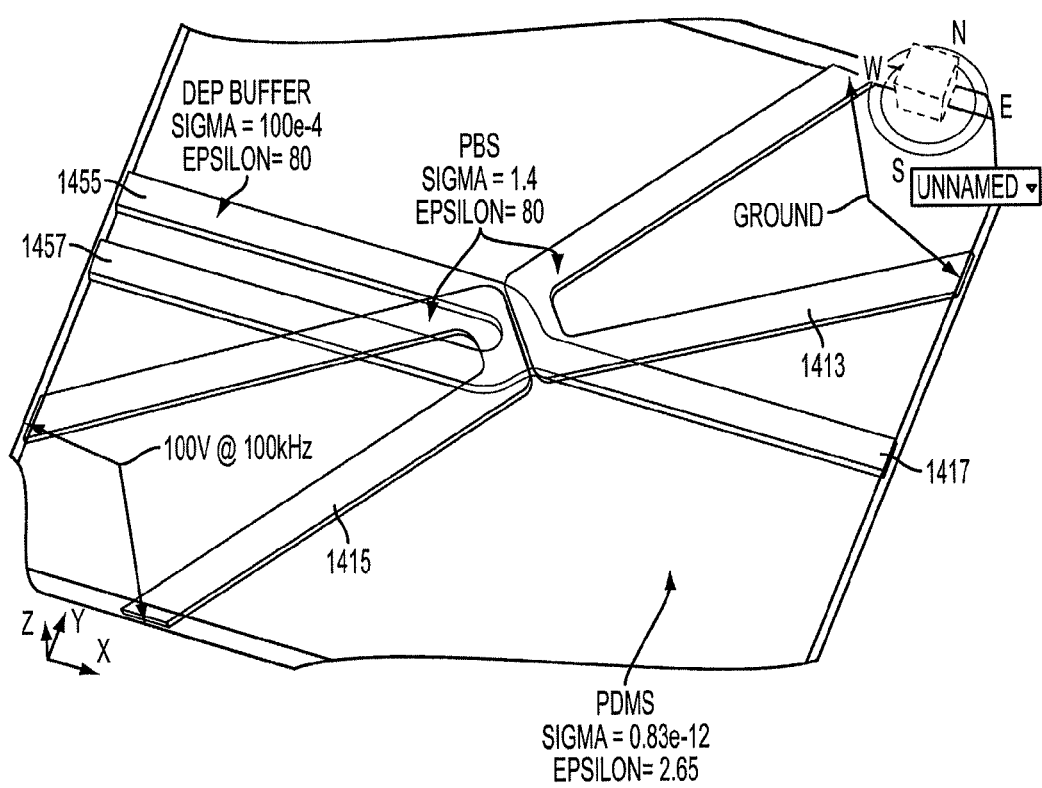
FIG. 14 shows a schematic of an embodiment of continuous sorting device with identical electrodes.

The embodiment depicted in FIG. 14 is a three layer device with both electrodes 1413, 1415 located on the same layer. In the embodiment of FIG. 14, the sample channel 1417 splits into two channels, and upper sample channel 1455 and a lower sample channel 1457. In this embodiment, as they travel from right to left, particles experiencing positive DEP will be deviated into the upper sample channel 1455 while particles experiencing negative DEP will be forced into the lower channel 1457, allowing for their separation.

The boundary and material properties depicted are typical of those tested experimentally.

Figure 15:
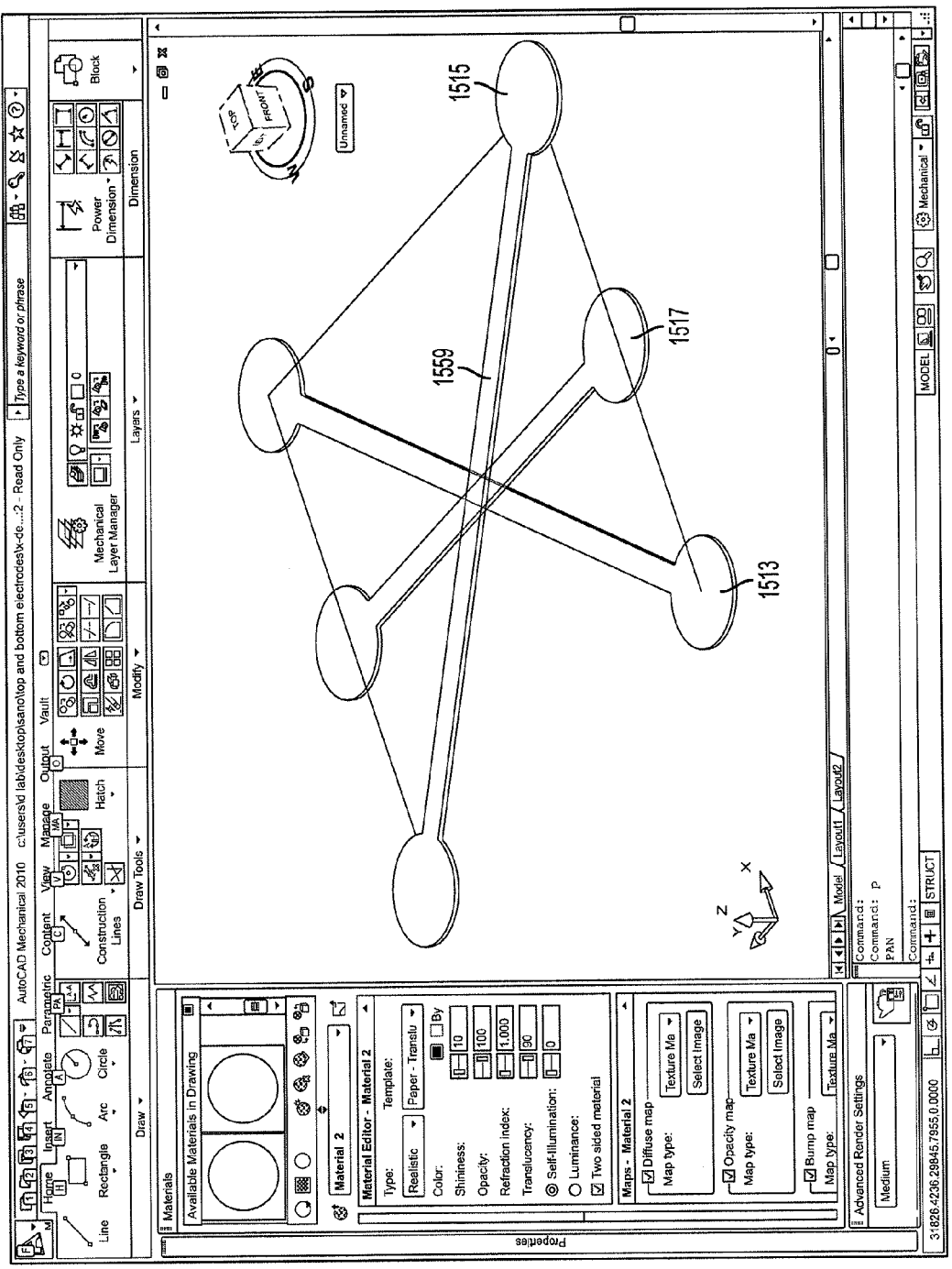
FIG. 15 shows a schematic of an embodiment of a batch sorting 5 layer device with each electrode and sample channel on a separate layer.
Figure 17B:
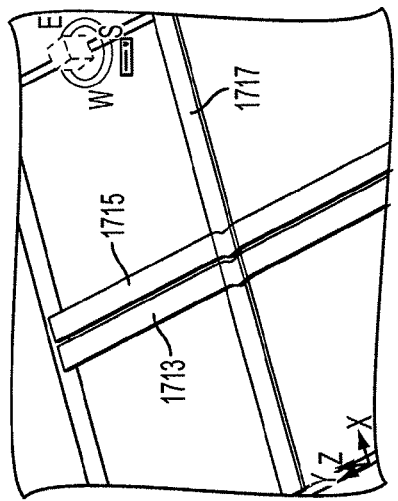
FIGS. 17A-D show schematics of embodiments of three layer devices of the present invention. The geometry of the main and side channels may be changed for different microparticle DEP manipulation strategies.
Figure 17D:
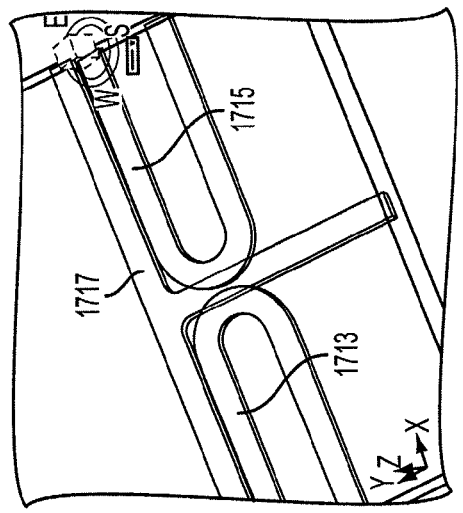
Figure 17A:
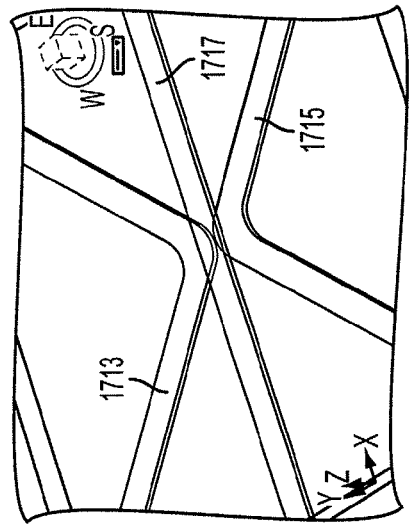
Figure 17C:
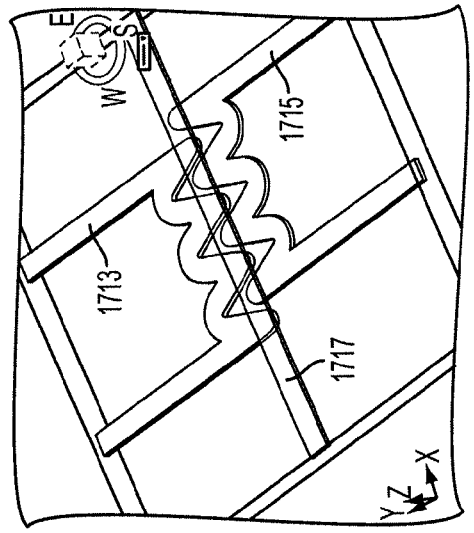

The embodiment depicted in FIG. 15 is a five layer device. A thin membrane separates the bottom electrode 1513 from the sample channel 1517 and another separates the sample channel 1517 from the top electrode 1515. This device may be used to batch sort particles. An AC electric field is applied to the electrodes. Particles would be allowed to trap in the region where the electrodes overlap 1559. After a desired time, the electric field would be reduced releasing the particles for downstream analysis.

The embodiment depicted in FIG. 16 is a three layer device. A 50 micron PMMA barrier separates the electrode channels 1613, 1615 from the sample channel 1617. In this embodiment, the two electrode channels are separated by 100 microns and each channel is 500 microns wide. This design can be used to batch sort cells and continuously sort cells. Below a certain threshold, particles may be pushed toward one side of the sample channel, separating them from the bulk solution (continuous sorting). Above a certain threshold, particles will be trapped in the region of the sample channel which lies between the two electrode channels. FIG. 16B shows an image of pearl chaining red blood cells being trapped in the sample channel at 200 kHz and 50 V. FIGS. 16C and D show images of 4 micron heads being trapped along the sample channel walls while 1 micron beads are forced to the center of the channel by negative DEP at 400 kHz and 50 V.

Further, non-limiting examples of embodiments of devices of the present invention are shown in FIGS. 17A-D, with like numbers indicating like elements.

In certain embodiments of the present invention, the sample channel may be designed with multiple inlets and outlets. Multiple inlets and outlets for the sample channel may allow the cDEP device more flexibility for sample handling and micro-particle manipulation for different purposes.

The methods and devices of the present invention allow for the sort of various types of particles, including cells. For the purposes of this disclosure sorting is intended to mean the separation of particles based on one or more specific characteristics. There are many different characteristics by which particles may be sorted, including, but not limited to: particle size, particle shape, particle charge, internal conductivity, shell or outer layer conductivity, proteins present in or on the particle, genetic expression, ion concentrations within the particle, state—for example metastatic vs non-metastatic cancer cells of the same phenotype and cellular genotype. Particles that may be separated, isolated and/or analyzed using the methods and devices of the present invention include cells isolated from organisms, single celled organisms, beads, nanotubes, DNA, molecules, few cell organisms (placozoans), Zygotes or embryos, drug molecules, amino acids, polymers, monomers, dimers, vesicles, organelles and cellular debris.

The methods by which certain embodiments sort particles can vary but include: batch sorting (where particles of a certain type are trapped in a particular region for a time before being released for later analysis), continuous sorting (where particles of a certain type are continuously diverted into a separate region of the channel or device), repulsion (negative DEP), attraction (positive DEP), and field flow fractionation.

cDEP and Downstream Analysis cDEP can be used in combination with other microfluidic technologies to form complete lab on a chip solutions. Examples of some downstream analysis techniques include: flow cytometry, PCR and impedance measurement, which may be used alone or in combination. Those of skill in the art will recognize that there are other methods of downstream analysis that may be applied after particles are sorted using the devices and methods of the present invention.

The devices and methods of the present invention can be used to enhance other trapping and sorting technologies such as dielectrophoresis, insulator based dielectrophoresis (iDEP), protein marker detection, field flow fractionation and diffusion (e.g. H-channel devices). For example, a device may have insulating pillars coated with a particular binding protein to detect circulating cancer cells. However, it is necessary that cells come in contact with the pillars in order for them to become permanently attached. cDEP can be employed to ensure that particles come in contact with the pillars, thus trapping any circulating cancer cells even after the electric field is removed.

Conductive Solutions

Any conductive solution or polymer may be used in the electrode channels of devices of the present invention. Examples of conductive solutions include phosphate buffer saline (PBS), conducting solutions, conductive gels, nanowires, conductive paint, polyelectrolytes, conductive ink, conductive epoxies, conductive glues and the like.

Fluid Flow

In certain embodiments, pressure driven flow or electrokonetic flow can be used to move the sample in the sample channel. The pressure driven flow used may be provided by an external source, such as a pump or syringe, or may be provided by the force of gravity. One of skill in the art will recognize that various methods are applicable for moving the sample in the sample channel.

Electrorotation Rate Measurement (ROT Spectra)

Figure 18B:
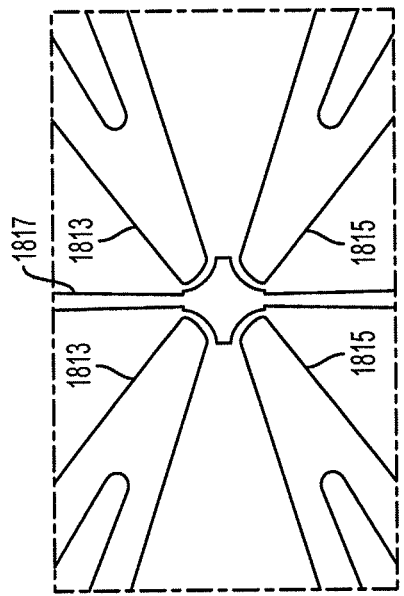
FIG. 18B shows an exploded view of the box in FIG. 18A.
Figure 18A:
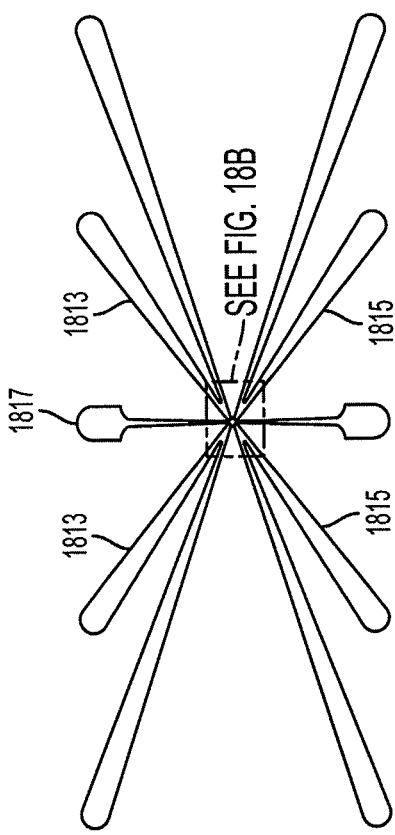
FIGS. 18A and B show schematics of an embodiment of a device design to measure the electrorotation of the cells/ micro-particles suspended in medium.

It is contemplated that cDEP devices may be designed to measure the electrorotation rate of different cell lines/micro-particles at different frequencies. These measurements can be used to back out the electrical properties of the cells/micro-particles. Methods for measuring such rates will be known to one of skill in the art. FIGS. 18A and B show an embodiment of the present invention which may be used for measurement of electrorotation rate, with panel B showing an exploded view of the region in the box in panel A. The sample channel 1817 is surrounded by pairs of each electrode 1813, 1815.

Electrorotation relies on a rotating electric field to rotate the cells or micro-particles. The electrical properties of the cells or micro-particles can be calculated by measuring the rotation speed of the particles at different applied frequencies. The rotating field is produced by electrodes arranged in quadrupole as shown in FIG. 18B. The electrodes are energized with AC signals phased 0°, 90°, 180°, and 270°.

cDEP and Electroporation

Reversible electroporation is a method to temporarily increase the cell membrane permeability via short and intense electrical pulses. The devices of the present invention may be designed to immobilize target cells in a medium dielectrophoretically with minimum mechanical stresses on the cell and reversibly electroporate the trapped cell. The conductivity of the cell is changed after electroporation. The device can be designed such that the electroporated cell leaves the trapping zone.

Irreversible electroporation (IRE) is a method to permanently open up electropores on the cell membrane via strong enough electrical pulses. The devices of the present invention may be designed to trap target cells using dielectrophoresis at trapping zones. These devices may be designed such that there is strong enough electric field at the trapping zone to irreversibly electroporate the trapped cell. The conductivity of the dead cell changes dramatically and therefore the DEP force decreases and the target cell can be released after IRE.

Electronics Used with Contactless Dielectrophoresis

In certain embodiments of the present invention, a sinusoidal signal may be used to elicit a DEP response from particles in the device. However, any electrical signal or signals that capitalize upon the capacitive nature of the barriers between the electrodes and fluidic channel(s) may be used with the present invention. These include sinusoidal, square, ramp, and triangle waves consisting of single or multiple fundamental frequencies however those familiar with electrical signal generation will be able to develop time-varying signals that may be used. The frequency range used to induce a DEP response in may range from tens of kilohertz to the megahertz range. However, it is also contemplated that devices may be designed to utilize frequencies range of several hundred hertz to hundreds of megahertz. For some of the embodiments presented herein, signal amplitudes ranged from about 30V (peak) to about 500V (peak). The amplitude of the applied signal only needs to be of a magnitude that induces a sufficient electric field in the channel to cause a change in cell behavior. Thus the required amplitude of the signal is dependent on the device configuration and DEP response of the target (cell, micro-particle, etc.).

There are numerous methods to generate a signal that may be used for contactless dielectrophoretic manipulation of cells and micro-particles. Methods for signal generation include oscillators (both fixed and variable), resonant circuits, or specialized waveform generation technologies including function generators, direct digital synthesis ICs, or waveform generation ICs. The output of these technologies may be computer controlled, user controller, or self-reliant.

Figure 19:
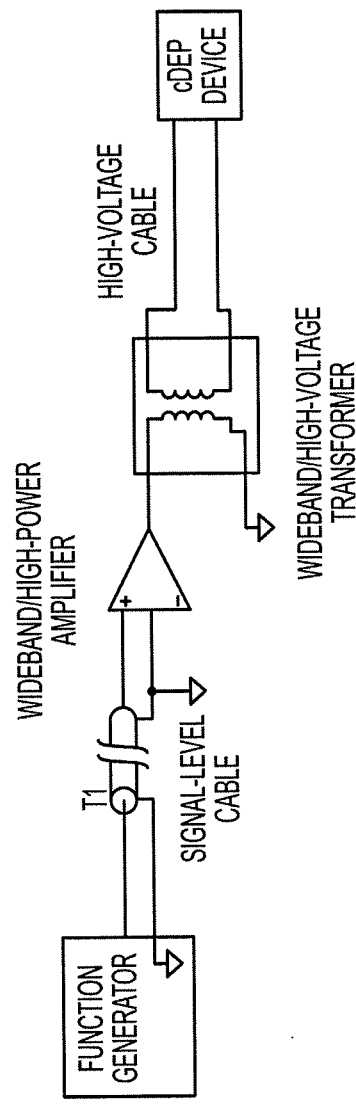
FIG. 19 shows a circuit diagram of an example electronics system which may be used with the devices of the present invention.

The output of a signal generation stage may then be coupled to the contactless dielectrophoretic device directly or coupled with an amplification technique in order to achieve the necessary parameters (voltage, current) for use in a device. Methods for amplification include solid state amplifiers, integrated circuit-based amplifiers, vacuum tube-based technologies, and transformers. Also, diode-based switches, semi-conductor devices used in the switch-mode, avalanche mode, and passive resonant components configured to compress and/or amplify a signal or pulse may be used to create a signal(s) to be used in contactless dielectrophoretic devices. An example electronics system which may be used with the devices of the present invention is shown in FIG. 19. In this implementation, a common laboratory function generator is used to generate the time varying signal necessary for experimentation. This signal is input to a solid-state amplifier which performs preliminary voltage and current amplification. Further voltage amplication is provided by inputting the output of the amplifier into a high voltage transformer which is then coupled to the electrode channels of the device.

Figure 20:
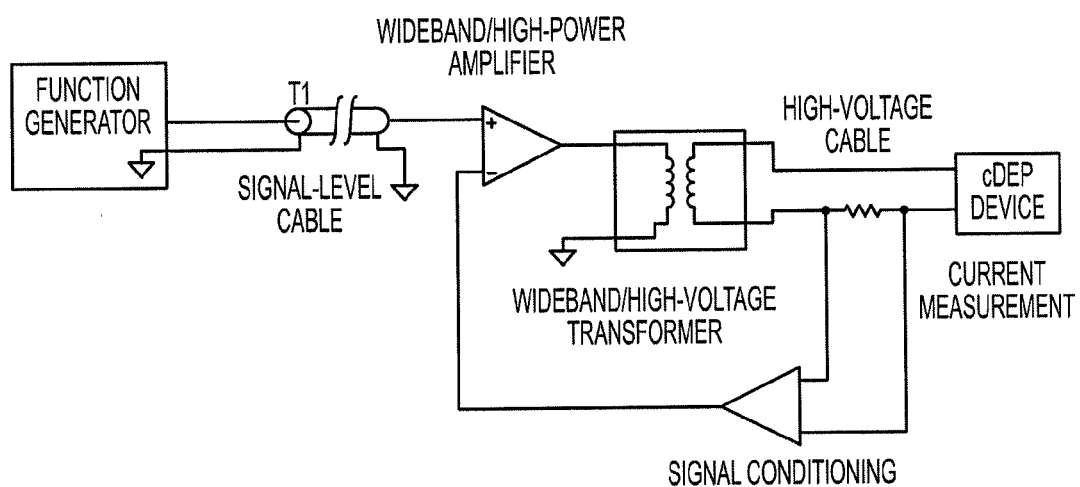
FIG. 20 shows a circuit diagram of an example electronics system having a feedback loop which may be used with the devices of the present invention.

Signal generation technology implemented with a feedback control system which allows the direct control of the electric field parameters within the device (electric field intensity, phase, frequency). One possible topology of a feedback implementation which may be used with the present invention is shown in FIG. 20. In FIG. 20 the current passing through the cDEP device is being measured in order to determine the magnitude of the electric field present within the device. There are several methods to perform this measurement including, but not limited to, current shunt resistors, current transformers, and transimpedance amplifiers. The measured current through the cDEP device is then used to maintain a the electric field in the device by adjusting the level of the signal generation or the gain of the amplification stages. However, those proficient in electrical engineering will be able to develop other feedback loop implementations to control the parameters of the electric field within the device.

The devices of the present invention may be coupled with other technologies to expand the functionality of the system. This may include additional electronics such as rotational spectroscopy or impedance detection in order to produce systems with a wider range of functionality.

Fabrication of Devices

The devices of the present invention may be fabricated using a stamp-and-mold method. An exemplary illustrated process flow is shown in FIG. 21. A silicon wafer is patterned using photolithography (FIGS. 21A and B) and then etched using deep reactive ion etching (DRIE) (FIGS. 21C and D). This etched wafer then serves as a mold onto which polydimethylsiloxane (PDMS) is poured and then allowed to cure FIG. 21E). The cured PDMS is then removed from the silicon wafer and contains an imprint of the device. Fluid ports are then punched in the cured PDMS mold as needed. Finally, the PDMS mold of the device is bonded to a glass microscope slide using oxygen plasma (FIG. 21F) and fluidic connections are punched through the PDMS.

Those skilled in microfabrication techniques will be able to modify this fabrication process to take advantage of materials with properties advantageous to the devices of the present invention. For example, the microfluidic structures of the device may be etched into a wafer of doped or intrinsic silicon, glass (such as Pyrex), or into an oxidation or nitride layer formed on top of a wafer. These materials would allow a researcher to perform experiments over a wider range of voltages and frequencies due to their increased permittivity and dielectric strength. Furthermore, the devices of the present invention lend themselves to other production techniques more suitable for mass fabrication such as injection molding and hot embossing.

It is also contemplated that there are other embodiments such as micromachining and capillary effect with glass beads that are not explicitly shown but that someone familiar with the art may employ in practicing the present invention.

Further specific examples of embodiments of the present invention are shown below. These examples are provided for exemplary purposes only and should not be considered to limit the scope of the invention as is set forth in the claims below.

EXAMPLES

Example 1

Separation of Cells Using cDEP

Background

Efficient biological particle separation and manipulation is a crucial issue in the development of integrated microfluidic systems. Current enrichment techniques for sample preparation include density gradient based centrifugation or membrane filtration (57), fluorescent and magnetic activated cell sorting (F/MACS) (61), cell surface markers (55), and laser tweezers (49). Each of these techniques relies on different cell properties for separation and has intrinsic advantages and disadvantages. Typically more sensitive techniques may require prior knowledge of cell-specific markers and antibodies to prepare target cells for analysis.

One alternative to these methods is dielectrophoresis (DEP) which is the motion of a particle due to its polarization in the presence of a non-uniform electric field (28,29). Currently, typical dielectrophoretic devices employ an array of thin-film interdigitated electrodes placed within the flow of a channel to generate a non-uniform electric field that interacts with particles near the surface of the electrode array (63). Such platforms have shown that DEP is an effective means to concentrate and differentiate cells rapidly and reversibly based on their size, shape, and intrinsic electrical properties such as conductivity and polarizability. These intrinsic properties arise due to the membrane compositional and electrostatic characteristics, internal cellular structure, and the type of nucleus (56) associated with each type of cell.

The application of dielectrophoresis to separate target cells from a solution has been studied extensively in the last two decades. Examples of the successful use of dielectrophoresis include the separation of human leukemia cells from red blood cells in an isotonic solution (7), entrapment of human breast cancer cells from blood (8), and separation of U937 human monocytic from peripheral blood mononuclear cells (PBMC) (9). DEP has also been used to separate neuroblastoma cells from HTB glioma cells (9), isolate cervical carcinoma cells (10), isolate K562 human CML cells (11), separate live yeast cells from dead (12), and segregate different human tumor cells (13). Unfortunately, the microelectrode-based devices used in these experiments are susceptible to electrode fouling and require complicated fabrication procedures (33,34).

Insulator-based dielectrophoresis (iDEP) is a practical method to obtain the selectivity of dielectrophoresis while overcoming the robustness issues associated with traditional dielectrophoresis platforms. iDEP relies on insulating obstacles rather than the geometry of the electrodes to produce spatial non-uniformities in the electric field. The basic concept of the iDEP technique was first presented by Masuda et al. (60). Others have previously demonstrated with glass insulating structures and AC electric fields that iDEP can separate DNA molecules, bacteria, and hematapoietic cells (64). It has been shown that polymer-based iDEP devices are effective for selective trapping of a range of biological particles in an aqueous sample (51). The patterned electrodes at the bottom of the channel in DEP create the gradient of the electric field near the electrodes such that the cells close enough to the bottom of the channel can be manipulated. However, the insulator structures in iDEP that usually transverse the entire depth of the channel provide non uniform electric field over the entire depth of the channel. iDEP technology has also shown the potential for water quality monitoring (35), separating and concentrating prokaryotic cells and viruses (58), concentration and separation of live and dead bacteria (2), sample concentration followed by impedance detection (36), and manipulation of protein particles (59).

While many have had success designing and fabricating different DEP and iDEP microdevices to manipulate particles in biological fluids, there are some potential drawbacks of these techniques. The traditional DEP technique suffers from fouling, contamination, bubble formation near integrated electrodes, low throughput, and an expensive and complicated fabrication process (33,34). The insulating obstacles employed by iDEP are meant to address these shortcomings and are less susceptible to fouling than integrated electrodes (38). iDEP's fabrication process is also much less complicated; the insulating obstacles can be patterned while etching the microchannel in one step. This technique has the added benefit of making the process more economical in that mass fabrication can be facilitated through the use of injection molding.

Unfortunately, one of the primary drawbacks of an iDEP system is the presence of a high electric field intensity within the highly conductive biological fluid inside the microchannel (33, 39). The relatively high electrical current flow in this situation causes joule heating and a dramatic temperature increase. The ideal technique would combine iDEP's simple fabrication process and resistance to fouling with DEP's reduced susceptibility to joule heating all-the-while preserving the cell manipulation abilities of both methods.

The inventors have developed an alternative method to provide the spatially non-uniform electric field required for DEP in which electrodes are not in direct contact with the biological sample. The absence of contact between electrodes and the sample fluid inside the channel prevents bubble formation and mitigates fouling. It is also important to note that without direct contact between the electrodes and the sample fluid, any contaminating effects of this interaction can be avoided. In fact, the only material in contact with the sample fluid is the substrate material the device is patterned on. In the present method, an electric field is created in the microchannel using electrodes inserted in a highly conductive solution which is isolated from the main channel by thin insulating barriers. These insulating barriers exhibit a capacitive behavior and therefore an electric field can be produced in the main channel by applying an AC electric field across them. Furthermore, non-uniformity of the electric field distribution inside the main channel is provided by the geometry of insulating structures both outside and inside the channel.

In order to demonstrate this new method for cell separation and manipulation, a microfluidic device to observe the DEP response of cells to a non-uniform electric field created without direct contact from electrodes has been designed and fabricated. Modeling of the non-uniform electric field distribution in the device was accomplished through an equivalent electronic circuit and finite element analysis of the microfluidic device. The effects of different parameters such as total applied voltage, applied frequency, and the electrical conductivity of the fluid inside and outside of the main channel on the resulting DEP response were simulated and then observed through experimentation. A DEP response was observed primarily as a change in cell trajectory or velocity as it traveled through the device. Further evidence of this DEP response to the non-uniform electric field is provided by the electrorotation of cells, and their aggregation in "pearl chain" formations.

Theory

Dielectrophoresis DEP is the motion of polarized particles in a non uniform electric field toward the high (positive DEP) or low (negative DEP) electric field depending on particle polarizability compared with medium conductivity. The time-average dielectrophoretic force is described as (28,29):

$$F_{DEP} = 2\pi \in_m r^3 Re\{K(\omega)\} \nabla (E_{rms} \cdot E_{rms}) \quad (1)$$

where $\in_m$ is the permittivity of the suspending medium, r is the radius of the particle, $E_{rms}$ is the root mean square electric field. $Re\{K(\omega)\}$ is the real part of the Clausius-Mossotti factor $K(\omega)$. The Clausius-Mossotti is given by:

$$K(\omega) = \frac{\varepsilon_p^* - \varepsilon_m^*}{\varepsilon_p^* + 2\varepsilon_m^*} \quad (2)$$

where $\in_p^*$ and $\in_m^*$ are the complex permittivities of the particle and the medium, respectively. Complex permittivity is defined as $$\varepsilon^* = \varepsilon + \frac{\sigma}{j\omega} \quad (3)$$

where $\in$, and $\sigma$ are the real permittivity and conductivity of the subject and $\omega$ is the frequency.

Electrorotation is the rotation of polarized particles suspended in a liquid due to an induced torque in a rotating electric field (37). The maximum magnitude of the torque is given by $$\Gamma = -4\pi \in_m r^3 Im\{K(\omega)\} (E_{rms} \cdot E_{rms}) \quad (4)$$

where $Im\{K(\omega)\}$ is the imaginary part of the Clausius-Mossotti factor $K(\omega)$.

Assuming the cells are spherical particles in the medium, the hydrodynamic frictional force, $f_{Drag}$, due to translation and hydrodynamic frictional torque, R, due to rotation are given by:

$$f_{Drag} = 6\eta r \pi (u_p - u_f) \quad (5)$$

$$R = 8\eta r^3 \pi \Omega \quad (6)$$

where r is the particle radius, $\eta$ is the medium viscosity, $u_p$ is the velocity of the particle, $u_f$ is the medium velocity, R is induced torque, and $\Omega$ is electrorotation rate (rad·S$^{-1}$).

The magnitude of the steady state electrorotation rate $\Omega$ and translational velocity is determined by a balance between the induced torque and the hydrodynamic friction and between the induced dielectrophoretic force and Stoke's drag force on a cell respectively. In this preliminary study it should be noted that the effect of the acceleration term is considered to be negligible. The relationship is given by:

$$\Omega(\omega) = \frac{\varepsilon_m}{2\eta} Im\left(\frac{\varepsilon_p^* - \varepsilon_m^*}{\varepsilon_p^* + 2\varepsilon_m^*}\right) E_{rms} \cdot E_{rms} \quad (7)$$

$$u_p = u_f - \mu_{DEP} \nabla (E \cdot E) \quad (8)$$

where $\mu_{DEP}$ is the dielectrophoretic mobility of the particle and is defined as:

$$\mu_{DEP} = \frac{\varepsilon_m r^2}{3\eta} \text{Re}\left(\frac{\varepsilon_p^* - \varepsilon_m^*}{\varepsilon_p^* + 2\varepsilon_m^*}\right) \quad (9)$$

Methods

Micro Fabrication Process

Deep Reactive Ion Etching (DRIE)

A silicon master stamp was fabricated on a <100> silicon substrate. AZ 9260 (AZ Electronic Materials) photoresist was spun onto a clean silicon wafer and softbaked at 114 C for 45 seconds (FIG. 21a). The wafer was then exposed to UV light for 45 seconds with an intensity of 12 W/m through a chrome plated glass mask. The exposed photoresist was then removed using Potassium based buffered developer AZ400K followed by another hard baking at 115 C for 45 seconds (FIG. 21b). Deep Reactive Ion Etching (DRIE) was used to etch the silicon master stamp to depths ranging from 50-100 microns (FIG. 21c). The silicon master stamp was then cleaned with acetone to remove any remaining photoresist (FIG. 21d). The scalloping effect, a typical effect of the DRIE etching method, creates a surface roughness which is detrimental to the stamping process. In order to reduce the surface roughness, silicon oxide was grown on the silicon master using thermal oxidation and then was removed (FIG. 21g-i).

PDMS

The liquid phase PDMS was made by mixing the PDMS monomers and the curing agent in a 10:1 ratio (Sylgrad 184, Dow Corning, USA). The bubbles in the liquid PDMS were removed by exposing the mixture to vacuum for an hour. A enclosure was created around the wafer using aluminum foil in order to contain the PDMS on the wafer as well as to ensure the proper depth for the PDMS portion of the device. The clean PDMS liquid was then poured onto the silicon master and 15 minutes was allowed for degassing. The PDMS was then cured for 45 min at 100 C (FIG. 21e) and then removed from the mold. Finally, fluidic connections to the channels were punched with 15 gauge blunt needles (Howard Electronic Instruments, USA).

Bonding

Microscope glass slides (3"×2"×1.2 mm, Fisher Scientific, USA) were cleaned with soap and water and rinsed with distilled water and isopropyl alcohol then dried with a nitrogen gun. The PDMS replica was bonded with the clean glass slides after treating with oxygen plasma for 40 s at 50 W RF power (FIG. 21f). A schematic with dimensions and equivalent circuit model of the device is presented in FIG. 22a. The side channels are separated from the sample channel with 20 μm PDMS barriers.

Experimental Setup

Pipette tips, inserted in the punched holes in the PDMS portion of the device, were used as reservoirs for fluidic connections to the channels. Pressure driven flow (10 to 15 μl/hr was provided by an imbalance in the amount of the sample in these reservoirs of the main channel. An inverted light microscope (Leica DMI 6000B, Leica Microsystems, Bannockburn, Ill.) equipped with a digital camera (Hamamatsu EM-CCD C9100, Hamamatsu Photonics K.K. Hamamatsu City, Shizuoka Pref., 430-8587, Japan) was used to monitor cells in the main channel. Microfluidic devices were placed in a vacuum jar for at least half an hour before running the experiments to reduce priming issues and then the side and main microchannels were filled with PBS and DEP buffer respectively.

Cells and Buffer

The THP-1 human Leukemia monocytes, MCF-7 breast cancer cells, and MCF-10A breast cells were washed twice and resuspended in a prepared DEP buffer (8.5% sucrose [wt/vol], 0.3% glucose [wt/vol], and 0.725% [vol/vol] RPMI) (Flanagan, Lu et al. 2008). The electrical conductivity of the buffer was measured with a Mettler Toledo SevenGo pro conductivity meter (Mettler-Toledo, Inc., Columbus, Ohio) to ensure that its conductivity was 100 μS/cm. These cells were observed to be spherical while they are in suspension. The measured cell diameters of with the corresponding standard deviations (n=30) of these cell are given in Table 2 below.

Electronics

A commercially available two-transistor inverter circuit (BXA-12576, JKL Components Corp., USA) was modified to provide a high-frequency and high-voltage AC signal for the device (FIG. 2b). The circuit relies on the oscillation created by the two-transistors and passive components to create an AC voltage on the primary side of a transformer. This voltage is then stepped-up by the transformer to give a high-output voltage on the secondary side to which the microfluidic device was connected.

The resonant frequency at which the circuit operates is highly dependant on the load impedance connected to the secondary side of the transformer. Two high-voltage power supplies were fabricated with resonant frequencies of 85 kHz and 126 kHz. A DC input voltage was provided by a programmable DC power supply (PSP-405, Instek America Corp., USA) which allowed adjustment of the output voltage by varying the input voltage. This technique allowed the output voltage of the power supplies to be varied from approximately 100 Vrms to 500 Vrms. A three-resistor voltage divider network, with a total impedance of one megaohm, was added to the output of the inverter circuit in order to provide a scaled (100:1) output voltage to an oscilloscope (TDS-1002B, Tektronix, USA) which facilitated monitoring the frequency and magnitude of the signal applied to the microfluidic device. All circuitry was housed in a plastic enclosure with proper high-voltage warnings on its exterior and connections were made to the microfluidic device using high-voltage test leads.

Translational and Rotational Velocity Measurement

Figure 23A:
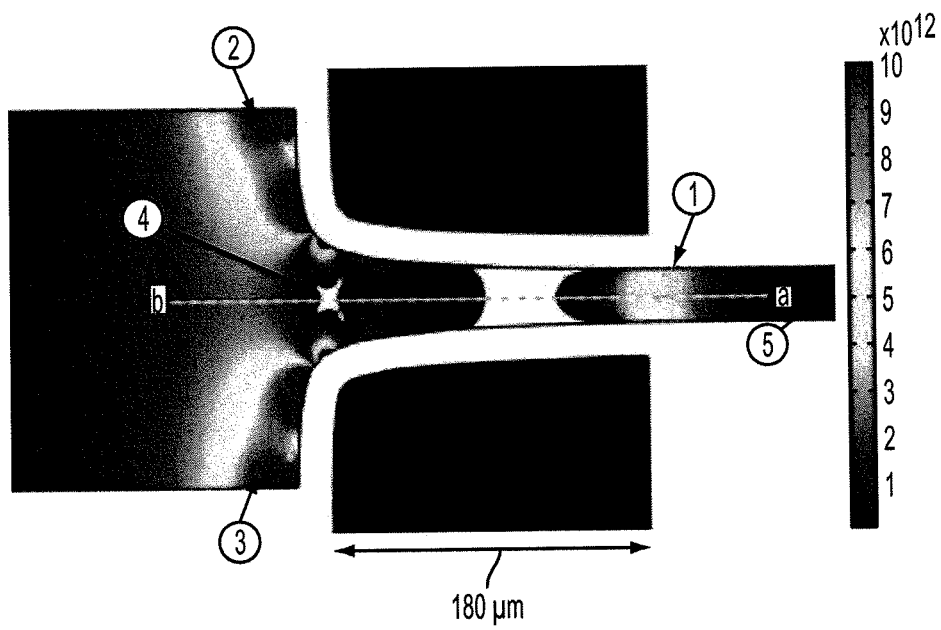
FIG. 23A shows a surface plot of the gradient of the field ($kg^2 mC^{-2} S^{-4}$) within the main microchannel.

The average velocity of the THP-1, MCF-7 and MCF-10A cells were measured in the microfluidic device along the centerline a-b in FIG. 23 from point 1 to point 4. Time-lapse videos were recorded of the cells motion before and after applying an ac electric field through the platinum electrodes inserted in the side channels. These recorded videos then were converted to JPEG files using the Leica software, (Leica DMI 6000B, LAS AF 1.6.3 Leica Microsystems, Bannockburn, Ill.), in order to measure the traveling time of the target cells, for a known specific distance in the microchannel, before and after inducing the electric field in the main microfluidic channel. Results are summarized below.

Numerical Modeling

The microfluidic device was modeled numerically in Comsol multi-physics 3.4 using AC/DC module (Comsol Inc., Burlington, Mass., USA). Since dielectrophoresis depends on the gradient of the electric field, $\nabla E = \nabla(\nabla\varnothing)$, it is necessary to determine the electric field distribution within a channel geometry. This is done by solving for the potential distribution, $\phi$ using the Laplace equation, $\nabla^2\varnothing = 0$. The boundary conditions used are prescribed uniform potentials at the inlet or outlet of the side channels, and a zero derivative normal to the channel walls, $\nabla\varnothing \cdot n = 0$, where n is the local unit vector normal to the walls.

The values for the electrical conductivity and permittivity of the PDMS, PBS, and DEP buffer that was used in this numerical modeling are given in Table 1. PBS and DEP buffer electrical properties are used for the side and main microfluidic channels, respectively.

TABLE 1

Electrical properties of the materials and fluids.

| Materials | Electrical Properties | |
|---|---|---|
| | Electrical Conductivity (S/m) | Relative Electrical Permittivity |
| PDMS | 0.83 × e−12 | 2.65 |
| PBS | 1.4 | 80 |
| DEP Buffer | 0.01 | 80 |

The effect of the external voltage and the frequency on the gradient of the induced electric field has been studied. The gradient of the electric field along the center line of the main channel is investigated numerically for different applied voltages (100, 200, 350, and 500V) at 85 kHz and for different frequencies (40, 85, 125, and 200 KHz) at 250 Vrms applying voltage. Based on the available electronic circuit (250 Vrms at 85 KHz), the electric field distribution and the gradient of the electric field was mapped in the microfluidic device.

Results and Discussion

Numerical Results

FIG. 23 shows the surface and line plot of the gradient of the electric field inside the main microfluidic channel at the intersection between the main and the side channels. There is a high gradient of the electric field at the corners (points 1 and 2) as well as point 3, which can provide a strong DEP force. These results indicate that changes in the thickness of the PDMS barrier have a more significant effect on the gradient of the induced electric field inside the main channel than changes in the channel's geometry which is in agreement with the analytical results.

Figure 23B:
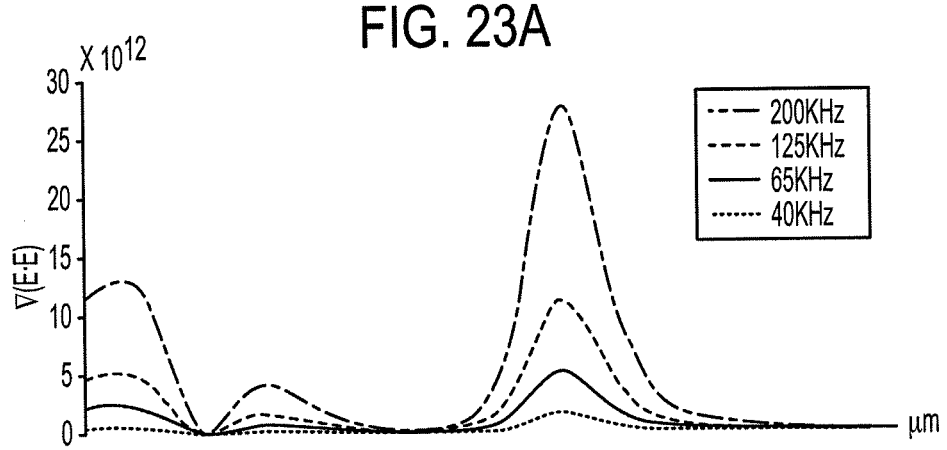
FIG. 23B shows a line plot of the gradient ($kg^2 mC^{-2} S^{-4}$) along the line a-b (mm) for four different frequencies (40, 85, 125, and 200 kHz) at 250 Vrms.
Figure 23C:
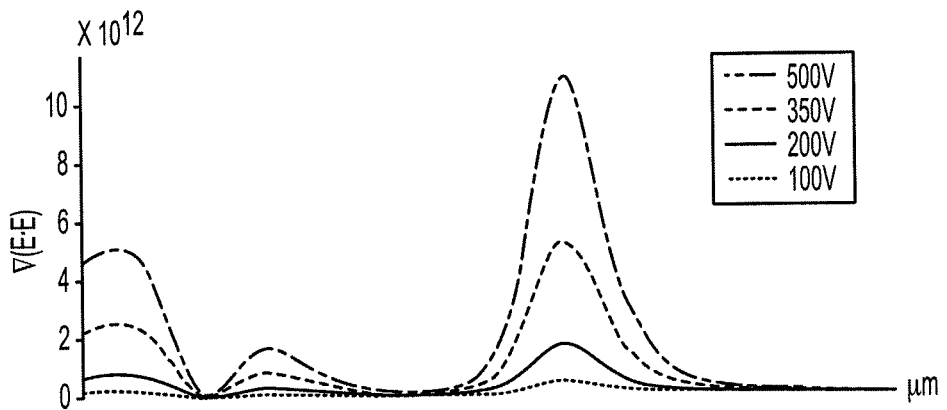
FIG. 23C shows the line plot of the gradient of the electric field along the line a-a for four different applied voltages (100, 200, 350, and 500V) at 85 kHz.

In FIG. 23b the gradient of the electric field along the line a-b is plotted for different applied frequencies (40, 85, 125, and 200 KHz) at 250 Vrms. The effect of the total external voltage across the microfluidic device on the gradient of the electric field (along the line a-b) is also investigated in FIG. 23c. DEP response of the system is plotted for four different voltages (100, 200, 350, and 500V) at 85 kHz.

An increased gradient of the electric field can be obtained by increasing the applied frequency or increasing the total applied voltage although it should be noted that adjusting the frequency will also affect the Clasius-Mossotti factor of the microparticles and needs to be considered. Also the induced gradient of the electric field in the main microfluidic channel is on the order of $10^{12}$ ($kg^2 \cdot m \cdot C^{-2} \cdot S^{-4}$) which is strong enough for particle manipulations.

Based on this numerical modeling, the voltage drop across the 20 μm PDMS barrier was 250V for an applied total voltage of 500V across the microfluidic electrode channels. This voltage drop is lower than the 400V break down voltage for a 20 μm PDMS channel wall. Thus, the DEP force can be amplified by adjusting the input voltage with some tolerance.

Electric Field Surface Plot

FIGS. 24a-c show the induced electric field intensity distribution inside the main microfluidic channel filled with the DEP buffer with a conductivity of 100 μS/cm. The highest electric field is induced at the zone of intersection between the main and the side channels and between the PDMS barriers. FIG. 24c also shows that with an applied AC electric field of 250 Vrms and 85 kHz the electric field does not significantly exceed 0.2 kV/cm in the main microfluidic channel.

Experimental Results

Cell Trapping-Contactless DEP Evidence

FIG. 25 shows the experimental results attained using MCF-7 breast cancer cells and THP-1 leukemia cells in the device. The behavior of cells traveling through the device under static conditions was observed to be significantly different than when an electric field was applied to the device. Three induced DEP responses were studied, rotation, velocity changes, and chaining.

Under a pressure driven flow, without an applied electric field, it was observed that THP-1 leukemia and MCF-7 breast cancer cells flow through the main microfluidic channel from right to left without any disruption or trapping. The cells were observed to be trapped, experiencing a positive DEP force, once an AC electric field at 85 KHz and 250 Vrms was applied. These results indicate that these cells have positive Clausius-Mossotti factor at 85 kHz frequency. Their velocity decreased at the intersection between the main and the side channels where the thin PDMS barriers are located. With the same electrical boundary conditions no trapping or cell movement disruption for MCF-10A normal breast cells was observed. However, these cells were trapped once an electric field at 125 kHz and 250 Vrms was applied.

Since the positive DEP force in the main microchannel depends on the electrical properties of the cells, different cell lines experience different forces at the same electrical boundary conditions (external voltage and frequency) in the same buffer. Cell bursting or lysis was not observed during contactless DEP trapping.

Translational Velocity

The cells were observed to move faster along the centerline of the sample channel in FIG. 23a from point 5 to point 1 when the electric field was applied as compared to their velocity due to pressure driven flow. As shown in FIG. 23, the magnitude of the DEP force is high at point 1. Because the DEP force is positive at 85 kHz, the cells are attracted to this point. Therefore, as the cells approach point 1 from the right, the positive DEP force is in the direction of the pressure driven flow, causing the cells to move faster down the channel. Conversely, the average velocity of the cells in the area between the thin PDMS barriers (from 1 to 4) decreases when the voltage is applied because the positive DEP force now acts in the opposite direction of the pressure driven flow.

Figure 26:
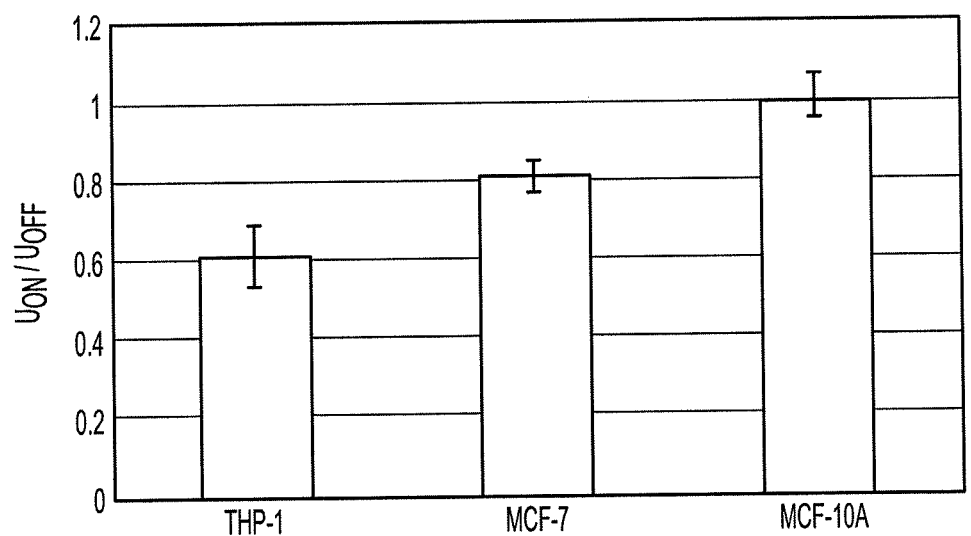
FIG. 26 shows a plot of the normalized velocity of THP-1, MCF-7, and MCF-10A cells. $U_{on}$ is the velocity of the cells while applying e-field and $U_{off}$ is the velocity of the cells while the power is off.

Table 2 compares the induced velocities of the cells with respect to their velocity under pressure driven flow. The normalized velocity (Uon/Uoff) for the three cell lines under the same electrical boundary conditions (250 Vrms at 85 kHz) are also reported in FIG. 26. The results show that there is a statistically significant difference in the cells velocity when the field is applied. Furthermore, when the experiments are normalized for comparison, the results suggest that this technique can be used to differentiate cells based on their electrical properties.

TABLE 2

The measure average velocity from point 1 to point 4 (FIG. 23) of five different cells before and after applying the electric field at the zone of trapping.

| Cell line | Diameter (μm) | Cell Velocity | | | | |
|---|---|---|---|---|---|---|
| | | Uon (μm/s) | Uoff (μm/s) | Uoff − Uon (μm/s) | Uon/Uoff | Ω (rad/s) |
| THP-1 | 15.4 ± 2 | 240 ± 13 | 392 ± 21 | 152 ± 19 | 0.61 | 8.1 ± 0.66 |
| MCF-7 | 18.5 ± 2.5 | 387 ± 7 | 476 ± 17 | 89 ± 17 | 0.81 | 19.4 ± 2.9 |
| MCF-10A | 18.2 ± 2.1 | 310 ± 17 | 313 ± 16 | 3 ± 24 | 0.99 | N.A. |

The same experiments with the same buffers and electrical boundary conditions were performed on MCF-10A breast cells without noticeable trapping or disruption, which shows that the electrical properties of the normal breast cells are different compared to the MCF-7 breast cancer cells. It also shows the sensitivity of the contactless DEP technique to isolate cells with close electrical properties.

There was a great tendency for cells to move towards the corners in the main channel. This agrees with the numerical results, which show there is a high gradient of the induced electric filed at the corners, which causes a strong positive DEP force and pulls cells towards these zones of the main microfluidic channel.

Rotational Velocity

Cell rotation in the main channel at the zone of trapping and between the thin PDMS barriers was present with an applied electric field. The rotational velocity of the cell is a function of its electrical properties, the medium permittivity, the medium dynamic viscosity as well as the properties of the electric field. The rotational velocity of the trapped THP-1, and MCF-7 cancer cells was measured in different experiments at one spot of the main microfluidic channel. No cell rotation was observed without an applied electric field. The reported rotational velocities in Table 2 are the average rotational velocities of five different cells of each of the cancer lines. These results imply that the average rotation velocities of the THP-1 and MCF-7 cancer cell lines are significantly different. Cell rotation for the MCF-10A cells with the same electrical boundary conditions in the same buffer solution was not observed.

Pearl-Chain

Figure 27:
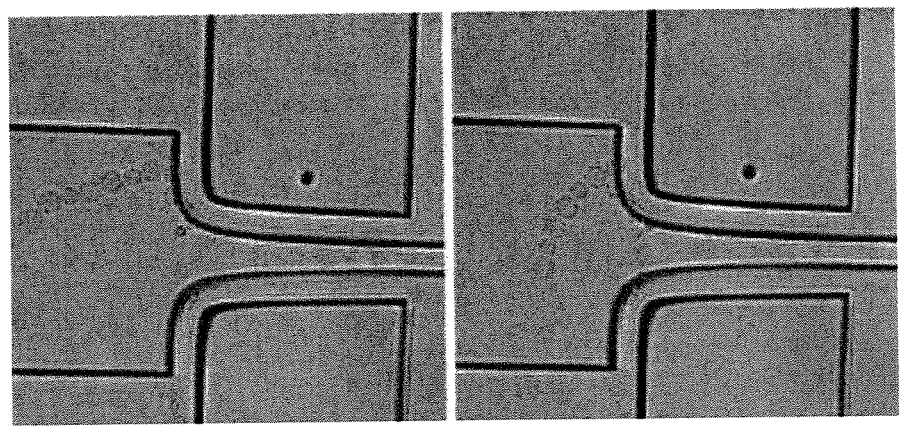
FIG. 27 shows two, single-frame images showing several cells arranged in the "pearl-chain" phenomena often associated with DEP. These images show the grouping of cells into a chain configuration in areas of the main channel with a high gradient of the electric field. Images were captured with an applied field of 250 Vrms at 85 kHz.

Cell aggregation and chain formation in DEP experiments with an AC field have been frequently observed and can be attributed to dipole-dipole interactions as well as local distortions of the electric field due to the cells' presence (28, 29, 52, 62). Particles parallel to the electric field attract each other because of this dipole-dipole force, resulting in pearl-chaining of the trapped cells in the direction of the electric field in the microfluidic channel. The cell chain formation was observed for the MCF-7 and THP-1 cancer cell lines in the experiments with an applied AC electric filed at 85 KHz and 250 Vrms (FIG. 27).

Conclusion

This Example demonstrates a new technique for inducing electric fields in microfluidic channels in order to create a dielectrophoretic force. The method relies on the application of a high-frequency AC electric signal to electrodes that are capacitively coupled to a microfluidic channel. In the subject device, the geometry of the electrodes and channels create the spatial non-uniformities in the electric field required for DEP. Three separate DEP responses were observed in the device, namely, translational velocity, rotational velocity, and chaining. In order to observe the devices effects in these three categories, three different cell lines were inserted into the devices and their individual responses recorded. Each cell line exhibited a response unique to its type due to the cell's specific electrical properties. This result highlights the ability of this technique to differentiate cells by their intrinsic electrical properties.

This technique may help overcome many of the challenges faced with traditional iDEP and DEP. Because the induced electric field is not as intense as comparable methods and is focused just at the trapping zone, it is theorized that the Joule heating within the main microfluidic channel is negligible. This could mitigate the stability and robustness issues encountered with conventional iDEP (39), due the conductivity distribution's strong dependence on temperature. Furthermore, challenges associated with cell lysing due to high temperatures (37) or irreversible electroporation due to high field strengths (50, 65) are overcome with the new design approaches disclosed herein.

Example 2

Selective Isolation of Live/Dead Cells Using Contactless Dielectrophoresis (cDEP)

Introduction

Isolation and enrichment of cells/micro-particles from a biological sample is one of the first crucial processes in many biomedical and homeland security applications (1). Water quality analysis to detect viable pathogenic bacterium (2-6) and the isolation of rare circulating tumor cells (CTCs) for early cancer detection (7-19) are important examples of the applications of this process.

Dielectrophoresis (DEP) is the motion of a particle in a suspending medium due to the presence of a non-uniform electric field (28, 29). DEP utilizes the electrical properties of the cell/particle for separation and identification (29, 66). The physical and electrical properties of the cell, the conductivity and permittivity of the media, as well as the gradient of the electric field and its applied frequency are substantial parameters determining a cell's DEP response.

One unique advantage of DEP over existing methods for cell separation is that the DEP force is strongly dependent on cell viability. The cell membrane, which is normally impermeable and highly insulating, typically becomes permeable after cell death (31). This results in the release of ions from the cytoplasm through the structural defects in the dead cell membrane and the cell conductivity will increase dramatically (32). This alteration in electrical properties after cell death make DEP live/dead cell separation and isolation possible.

The utilization of DEP to manipulate live and dead cells has previously been demonstrated through several approaches. To start, Suehiro et al. were able to utilize dielectrophoretic impedance measurements to selectively detect viable bacteria (67). Conventional interdigitated electrode DEP micro devices have also been used to separate live and heat-treated *Listeria* cells (68). Huang et al. investigated the difference in the AC electrodynamics of viable and nonviable yeast cells through DEP and electrorotation experiments (69) and a DEP-based microfluidic device for the selective retention of viable cells in culture media with high conductivity was proposed by Docoslis et al. (70).

Insulator-based dielectrophoresis (iDEP) has also been employed to concentrate and separate live and dead bacteria for water analysis (2). In this method, electrodes inserted into a microfluidic channel create an electric field which is distorted by the presence of insulating structures. The devices can be manufactured using simple fabrication techniques and can be mass-produced inexpensively through injection molding or hot embossing (35, 36). iDEP provides an excellent solution to the complex fabrication required by traditional DEP devices however, it is difficult to utilize for biological fluids which are highly conductivity. The challenges that arise include joule heating and bubble formation (37). In order to mitigate these effects, oftentimes the electrodes are placed in large reservoirs at the channel inlet and outlet. Without an additional channel for the concentrated sample (36), this could re-dilute the sample after it has passed through a concentration region.

The development a robust, simple, and inexpensive technique to perform DEP, termed "contactless dielectrophoresis" (cDEP) is described herein. This technique provides the non-uniform electric fields in microfluidic channels required for DEP cell manipulation without direct contact between the electrodes and the sample (40). In this method, an electric field is created in the sample microchannel using electrodes inserted into two conductive microchambers, which are separated from the sample channel by thin insulating barriers. These insulating barriers exhibit a capacitive behavior and therefore an electric field can be produced in the main channel by applying an AC field across the barriers (40).

The absence of contact between the electrodes and the sample fluid prevents problems associated with more conventional approaches to DEP and iDEP including contamination, electrochemical effects, bubble formation, and the detrimental effects of joule heating (33). Similar to iDEP, cDEP lends itself to a much simpler fabrication procedure. Devices are typically molded from a reusable silicon master stamp that has been fabricated from a single mask lithographic process. Once the master stamp has been fabricated, cDEP devices can be produced from the stamp outside of the cleanroom environment, allowing for rapid, mass fabrication of cDEP microfluidic devices.

As is shown below, the abilities of cDEP to selectively isolate and enrich a cell population was investigated. This was demonstrated through the separation of viable cells from a heterogeneous population also containing dead cells. Two cDEP microfluidic devices were designed and fabricated out of polydemethilsiloxane (PDMS) and glass using standard photolitography. The DEP response of the cells was investigated under various electrical experimental conditions in the range of the power supply limitations. Human leukemia THP-1 viable cells were successfully isolated from dead (heat treated) cells without lysing.

The separation of viable and nonviable cells is a critical starting point for this new technology to move towards more advanced applications. Optimization of these devices would allow for selective separation of cells from biological fluids for purposes such as: the diagnosis of early stages of diseases, drug screening, sample preparation for downstream analysis, enrichment of tumor cells to evaluate tumor lineage via PCR, as well as treatment planning (41-46). By using viable/non-viable separation as a model for these applications, a new generation of cDEP devices can be tailored around the results reported in this study.

Theory

Figure 28A:
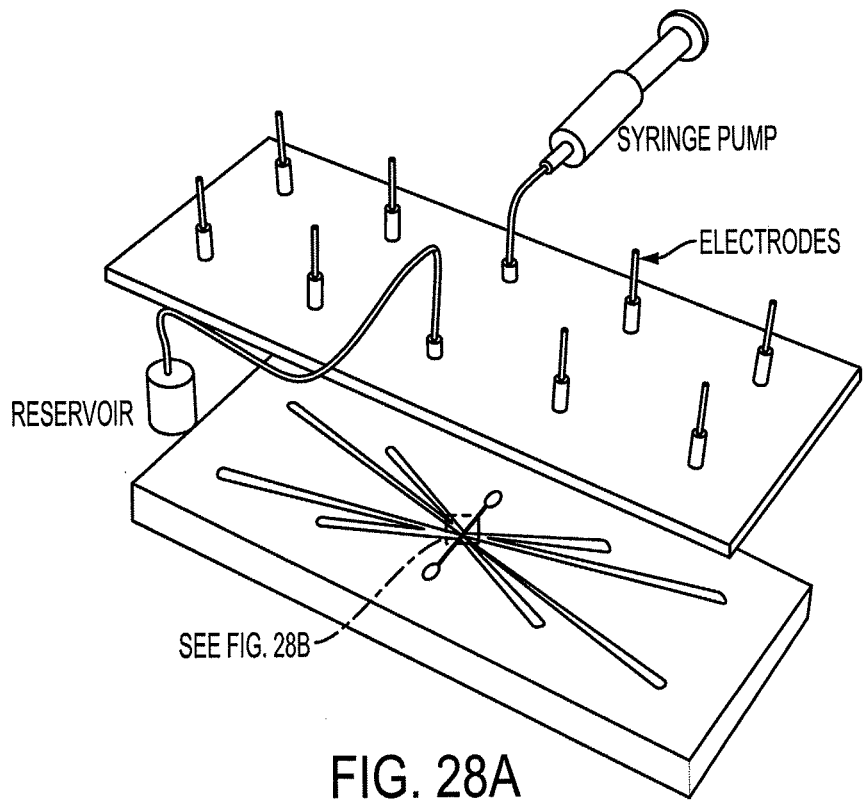
FIG. 28 shows a three dimensional schematic of the experimental set up of Example 2.
Figure 28B:
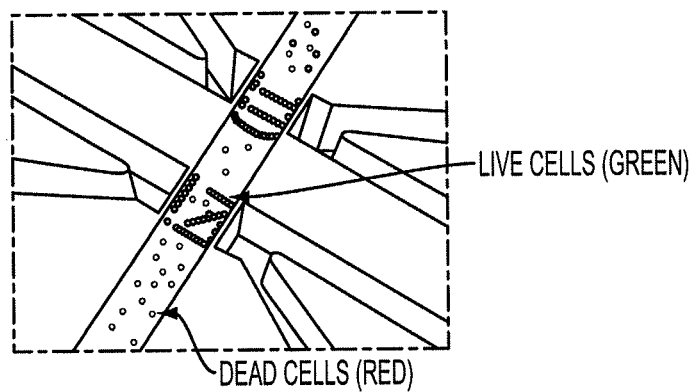

The 3D schematic of the experimental set up and device 1 is shown in FIG. 28. The dominant forces acting on the cell/particle in the microfluidic devices are shown in FIGS. 29(*a*) and 30(*a*). For particles larger than 1 µm, the Brownian motion is negligible compared to the DEP force 1. The DEP force acting on a spherical particle can be described by the following (1, 28, 71)

$$F_{DEP} = 2\pi \in_m r^3 Re\{K(\omega)\} \nabla (E_{rms} \cdot E_{rms}) \quad (1)$$

where $\in_m$ is the permittivity of the suspending medium, r is the radius of the particle, $E_{rms}$ is the root mean square electric field. $Re\{K(\omega)\}$ is the real part of the Clausius-Mossotti factor $K(\omega)$. The Clausius-Mossotti is given by $$K(\omega) = \frac{\varepsilon_p^* - \varepsilon_m^*}{\varepsilon_p^* + 2\varepsilon_m^*} \quad (2)$$

where $\in_p^*$ and $\in_m^*$ are the particle and the medium complex permittivity respectively. The complex permittivity is defined as follows:

$$\varepsilon^* = \varepsilon + \frac{\sigma}{j\omega} \quad (3)$$

where $\in$ is the permittivity, $\sigma$ is the conductivity, $j^2=-1$, and $\omega$ is the angular frequency.

Using the complex permittivity given in equation (3) of the particle and medium, the real part of Clausius-Mossotti factor is calculated as follows (72):

$$Re[f_{cm}] = \frac{(\sigma_p - \sigma_m)}{(1 + \omega^2 \tau_{MW}^2)(\sigma_p + 2\sigma_m)} + \frac{\omega^2 \tau_{MW}^2 (\epsilon_p - \epsilon_m)}{(\epsilon_p + 2\epsilon_m)} \quad (4)$$

For cells, the complex permittivity can be estimated using a single shell model, which is given by $$\varepsilon_p = \varepsilon_{mem} \frac{\gamma^3 + 2\left(\frac{\varepsilon_i - \varepsilon_{mem}}{\varepsilon_i + 2\varepsilon_{mem}}\right)}{\gamma^3 - \left(\frac{\varepsilon_i - \varepsilon_{mem}}{\varepsilon_i + 2\varepsilon_{mem}}\right)} \quad (5)$$

where $\gamma = r/(r-d)$, r is the particle radius, d is the cell membrane thickness, $\in_i$ and $\in_{mem}$ are the complex permittivities of the cytoplasm and the membrane, respectively (1, 72).

The parabolic velocity profile in the microchannel, shown in FIGS. 2(*a*) and 3(*a*), is due to the low Reynolds number pressure driven flow across the main channel. Assuming the cell as a spherical particle, the hydrodynamic drag force due to cell translation is given by $$f_{Drag} = 6\pi \eta r \pi (u_p - u_f) \quad (6)$$

where r is the particle radius, $\eta$ is the medium viscosity, $u_p$ is the velocity of the particle, and $u_f$ is the medium velocity.

Others have shown that for micro particles moving in viscous environments, the inertial forces are negligible (73). The characteristic time for a spherical particle suspended in fluid is reported to be $(2\rho r^2)/(9\eta)$, where $\rho$ is the density of the medium, r is radius of the particle, and $\eta$ is the viscosity of the medium.

For THP-1 cells with 15.4±2 µm diameter (40) this characteristic time would be 12 µs, which is orders of magnitude smaller than the time scale of the external forces and the experimental observations. The velocity of the particle is determined by a balance between the DEP force and Stoke's drag force. The relationship is given by $$u_p = u_f - \mu_{DEP} \nabla(E \cdot E) \quad (7)$$

where $\mu_{DEP}$ is the dielectrophoretic mobility of the particle and is defined as:

$$\mu_{DEP} = \frac{\varepsilon_m r^2}{3\eta} \text{Re}[f_{CM}] \quad (8)$$

Methods

Fabrication

Figure 29A:
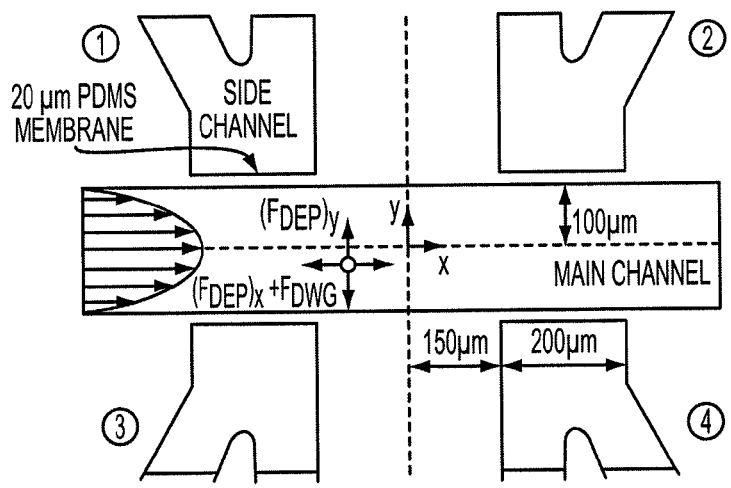
FIG. 29A shows two dimensional top view schematic of device 1 of Example 2 showing the dominated acting forces on the particle. The contours represent the electric fields modeled in Comsol multiphysics.
Figure 30A:
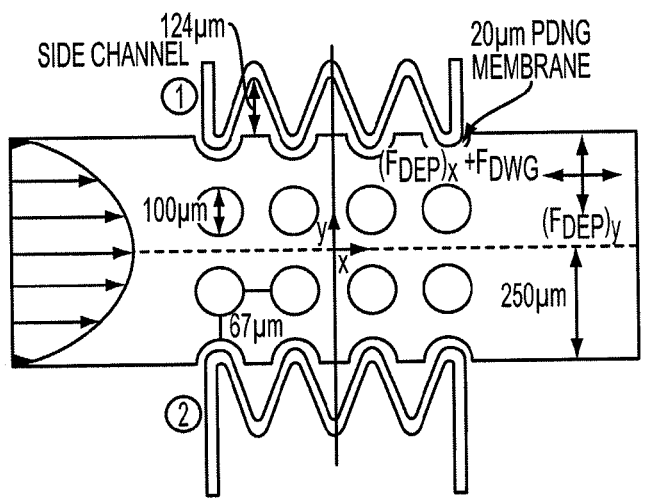
FIG. 30A shows a two dimensional top view schematic of device 2 of Example 2, showing the dominated acting forces on the particle. The contours represent the electric fields modeled in Comsol multiphysics.
Figure 30B:
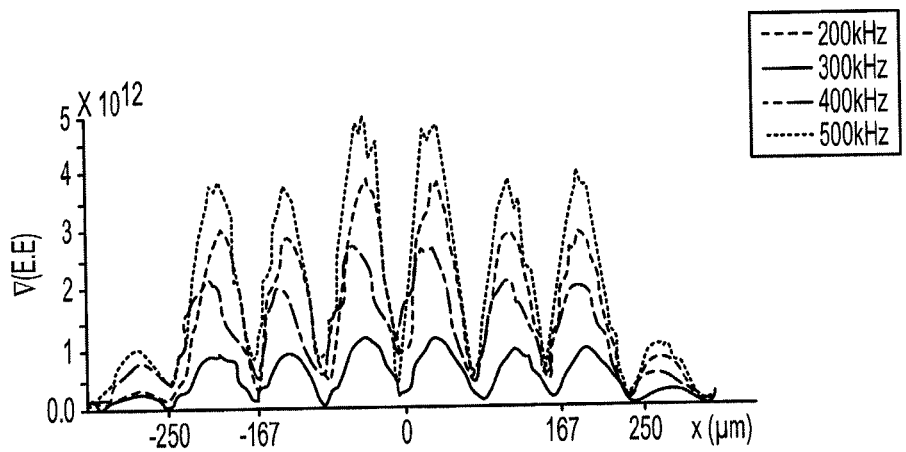
FIG. 30B shows a line plot of the gradient of the electric field squared ($kg^2mC^{-2}S^{-4}$) for four different electrical boundary conditions with efficient numerical cell trapping (V1=300 Vrms at 200 kHz, 300 kHz, 400 kHz, and 500 kHzV2=Ground) along the x axis (y=0).

A silicon master stamp was fabricated on a <100> silicon substrate following the previously described process 32. Deep Reactive Ion Etching (DRIE) was used to etch the silicon master stamp to a depth of 50 µm. Silicon oxide was grown on the silicon master using thermal oxidation for four hours at 1000° C. and removed with HF solvent to reduce surface scalloping. Liquid phase polydimethylsiloxane (PDMS) was made by mixing the PDMS monomers and the curing agent in a 10:1 ratio (Sylgrad 184, Dow Corning, USA). The degassed PDMS liquid was poured onto the silicon master, cured for 45 min at 100° C., and then removed from the mold. Fluidic connections to the channels were punched using hole punchers (Harris Uni-Core, Ted Pella Inc., Redding, Calif.); 1.5 mm for the side channels and 2.0 mm for the main channel inlet and outlet. Microscope glass slides (75 mm×75 mm×1.2 mm, Alexis Scientific) were cleaned with soap and water, rinsed with distilled water, ethanol, isopropyl alcohol, and then dried with compressed air. The PDMS mold was bonded to clean glass after treating with air plasma for 2 minutes. Schematics of the devices with dimensions are shown in FIGS. 29(a) and 30(a).

Cell Preparation

The live samples of THP-1 human leukemia monocytes were washed twice and resuspended in a buffer used for DEP experiments (8.5% sucrose [wt/vol], 0.3% glucose [wt/vol], and 0.725% [wt/vol] RPMI 43) to 106 cells/mL. The cell samples to be killed were first pipetted into a conical tube and heated in a 60° C. water bath for twelve minutes; an adequate time determined to kill a majority of the cell sample.

To enable simultaneous observation under fluorescent microscope, cells were stained using a LIVE/DEAD® Viability/Cytotoxicity Kit for mammalian cells (Molecular Probes Inc.). Calcein AM, which is enzymatically converted to green fluorescent calcein, was added to the live cell sample at 2 µL per ml of cell suspension. Ethidium homodimer-1 (EthD-1) was added to the dead cell sample at 6 µL per ml of cell suspension. This can only pass through damaged cell membranes and upon nucleic acid-binding produces a red fluorescence.

The two samples were then vortexed for 5 minutes, washed once and resuspended in DEP buffer. The live and dead suspensions were then mixed together in one conical tube with a final concentration of 106 cells/mL and final conductivity of 110-115 µS/cm measured with a SevenGo Pro conductivity meter (Mettler-Toledo, Inc., Columbus, Ohio). Live and dead cells were indistinguishable under bright field evaluation.

Experimental Set-Up

The microfluidic devices were placed in a vacuum jar for 30 minutes prior to experiments to reduce problems associated with priming. Pipette tips were used to till the side channels with Phosphate Buffered Saline (PBS) and acted as reservoirs. Aluminum electrodes were placed in the side channel reservoirs. The electrodes inserted in side channels 1 and 2 of device 1 (FIG. 29a) were used for excitation while the electrodes inserted in side channels 3 and 4 were grounded. The electrodes inserted in side channel 1 of device 2 (FIG. 30a) were used for excitation while the electrodes inserted in side channel 2 were grounded. Thin walled Teflon tubing (Cole-Parmer Instrument Co., Vernon Hills, Ill.) was inserted into the inlet and outlet of the main channel. A 1 ml syringe containing the cell suspension was fastened to a micro-syringe pump (Cole Parmer, Vernon Hills, Ill.) and connected to the inlet tubing. Once the main channel was primed with the cell suspension, the syringe pump was set to 0.02 mL/hr; equivalent to a velocity of 556 µm/sec for device 1 and 222 µm/sec for device 2. This flow rate was maintained for 5 minutes prior to experiments.

An inverted light microscope (Leica DMI 6000B, Leica Microsystems, Bannockburn, Ill.) equipped with color camera (Leica DFC420, Leica Microsystems, Bannockburn, Ill.) was used to monitor the cells flowing through the main channel. Once the flow rate of 0.02 ml/hr was maintained for 5 minutes an AC electric field was applied to the electrodes.

Device 1: Experiments were conducted at 50 Vrms, 75 Vrms, 100 Vrms, 125 Vrms and 150 Vrms. Trapping boundary conditions for this device were determined through visual inspection of the cells passing through the main channel. At each voltage, frequency was recorded for 80% trapping and the beginning of cell lyses. Significant lysing was considered to be when at least 10% of the cell population became lysed. The electric field was maintained for 30 seconds during each experiment. Eight trials were conducted at each voltage and corresponding frequencies were recorded where 80% trapping was observed.

Device 2: Trapping efficiency for this device was determined for voltages of 20 Vrms, 30 Vrms, 40 Vrms, 50 Vrms and frequencies of 200 kHz, 300 kHz, 400 kHz, 500 kHz at a constant flow rate of 0.02 mL/hr. Experimental parameters were tested at random to mitigate any variation in cell concentration, flow rate, device functionality and other experimental variables. Additionally, trapping efficiency was calculated at 0.02 mL/hr, 0.04 mL/hr, 0.06 mL/hr, and 0.08 mL/hr, with electrical parameters held constant at 500 kHz and 30 Vrms. Electrical parameters were selected randomly for each experiment for a total of five trials at each combination. The electric field was maintained for 30 seconds during each experiment. During the 30 second interval, all cells entering the trapping region of the device (the region containing pillars in the main channel) were counted, representing the total number of cells.

Electrical Equipment

AC electric fields were applied to the microfluidic devices using a combination of waveform generation and amplification equipment. Waveform generation was performed by a function generator (GFG-3015, GW Instek, Taipei, Taiwan) whose output was then fed to a wideband power amplifier (AL-50HF-A, Amp-Line Corp., Oakland Gardens, N.Y.). The wideband power amplifier performed the initial voltage amplification of the signal and provided the necessary output current to drive a custom-wound high-voltage transformer (Amp-Line Corp., Oakland Gardens, N.Y.). This transformer was placed inside a grounded cage and attached to the devices using high-voltage wiring. Frequency and voltage measurements were accomplished using an oscilloscope (TDS-1002B, Tektronics Inc. Beaverton, Oreg.) connected to a 100:1 voltage divider at the output of the transformer.

Numerical Modeling

The electric field distribution and its gradient $\nabla E = \nabla(\nabla\emptyset)$ were modeled numerically in Comsol multi-physics 3.5 using the AC/DC module (Comsol Inc., Burlington, Mass., USA). This is done by solving for the potential distribution, $\Phi$, using the governing equation, $\nabla\cdot(\sigma^*\nabla\emptyset)=0$, where $\sigma^*$ is the complex conductivity ($\sigma^*=\sigma+j\omega\in$) of the sub-domains in the microfluidic devices. The boundary conditions used are prescribed uniform potentials at the inlet or outlet of the side channels.

The values for the electrical conductivity and permittivity of the PDMS, PBS, and DEP buffer that were used in this numerical modeling are given in Table 3. PBS and DEP buffer electrical properties are used for the side and main microfluidic channels, respectively. The induced DEP effect inside the main channel was investigated for a range of frequencies and voltages. The gradient of the electric field along the center line (y=0) of the main channel as well as y=50 μm and y=100 μm was investigated numerically.

TABLE 3

Electrical properties of the materials and fluids.

| Materials | Electrical Properties | |
|---|---|---|
| | Electrical Conductivity (S/m) | Relative Electrical Permittivity |
| PDMS | $0.83 \times 10^{-12}$ | 2.65 |
| PBS | 1.4 | 80 |
| DEP Buffer | 0.01 | 80 |

Results and Discussion

Figure 29B:
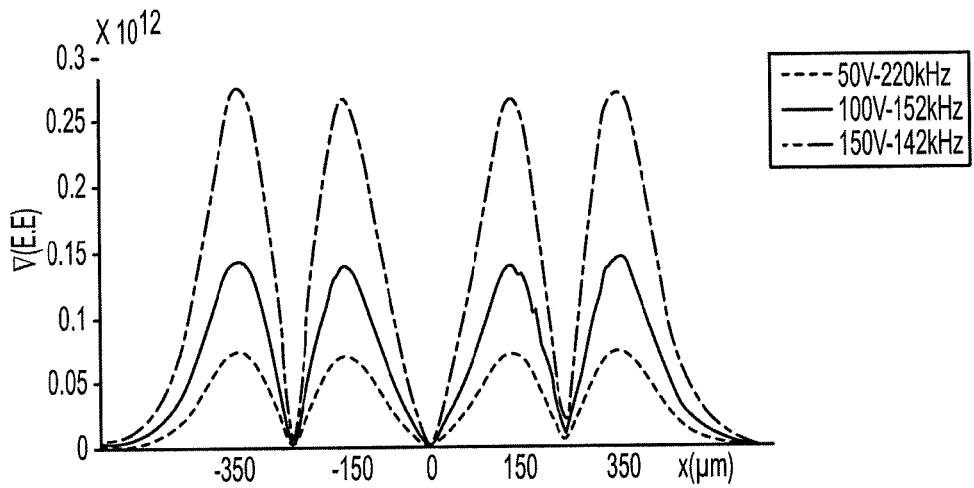
FIG. 29B shows a line plot of the gradient of the electric field squared ($kg^2mC^{-2}S^{-4}$) for three different electrical boundary conditions with efficient numerical cell trapping (V1=V2=50 Vrms at 220 kHz, 100 Vrms at 152 kHz, and 150 Vrms at 142 kHz and V3=V4=Ground).
Figure 29C:
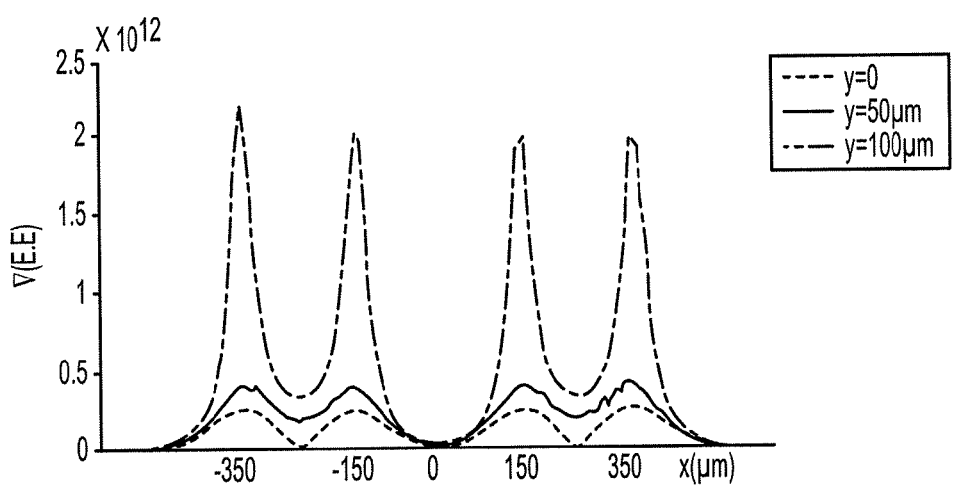
FIG. 29C shows a line plot of the gradient of the electric field squared ($kg^2mC^{-2}S^{-4}$) along the lines parallel to the center line of the main channel and at different distances from the channel wall for V1=V2=150 Vrms at 140 kHz boundary condition (y=0, 50, and 100 µm).

Device 1: The geometry of device 1 allowed for the rapid simulation of DEP effects within the sample microchannel which could then be verified through an efficient fabrication and experimentation procedure. The gradient of the electric field along the center line of the main channel of device 1 was numerically modeled and the results are plotted in FIG. 29b. FIG. 29b also shows that the maximum gradient of the electric field occurs at the terminations of the side channels. The dependance of the gradient of the electric field in the main channel on distance from the channel wall is shown in FIG. 29c. These numerical results indicate that the gradient of the electric field and thus the DEP effect is strongly related to the channel geometry.

Conclusions drawn from the numerical modeling of device 1 were verified through direct experimentation. Live cell concentration and trapping was observed for the electrical boundary conditions that were previously simulated (V1=V2=50 Vrms at 220 kHz, 100 Vrms at 152 kHz, and 150 Vrms at 142 kHz and V3=V4=Ground). A large DEP response was achieved with an applied voltage of 150 Vrms at 142 kHz. mirroring the numerical modeling shown in FIG. 29b. The majority of cell trapping within the device occurred at the edges of the electrodes as predicted by numerical results found in FIG. 29b.

Figure 31A:
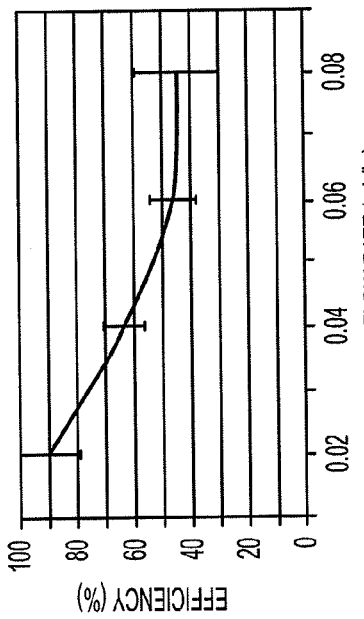
FIGS. 31A-D show plots of: (A) Voltage-frequency pairs to achieve 80% trapping efficiency for device 1 of Example 2; (B) Trapping efficiency of device 2 of Example 2 at 500 kHz and 30 Vrms for flow rates of 0.02, 0.04, 0.06, and 0.08 mL/hr; (C) Trapping efficiency at 0.02 mL/hr of device 2 of Example 2 at 200, 300, 400, and 500 kHz as voltages increase from 20 Vrms to 50 Vrms; and (D) Maximum gradient of the electric field along the x (y=0) and y (x=0) axis of device 2 of Example 2 for frequencies between 200 kHz and 1000 kHz.
Figure 32A:
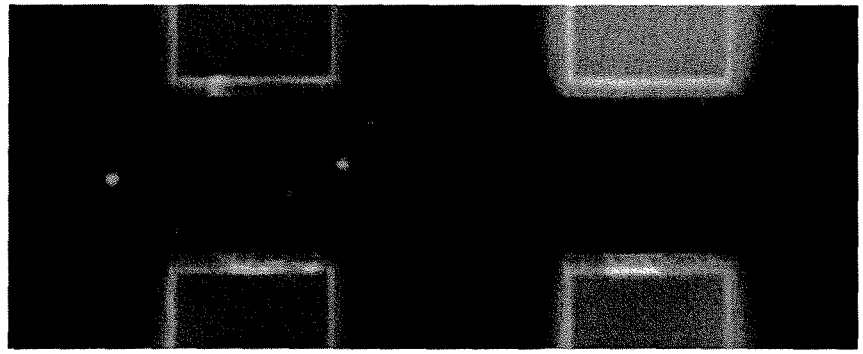
FIGS. 32A-C show images of experimental results for device 1 of Example 2: (A) Dead and live THP-1 cells are moving from right to left due to pressure driven flow without applying electric field; (B) 30 seconds after applying the electric field (V1=V2=100 Vrms at 152 kHz and V3=V4=Ground), the live cells were trapped due to positive DEP, but the dead cells pass by the trapping area; (C) Releasing the trapped live cells by turning off the power supply. Side channels are fluorescent due to Rhodamine B dye suspended in PBS.
Figure 32B:
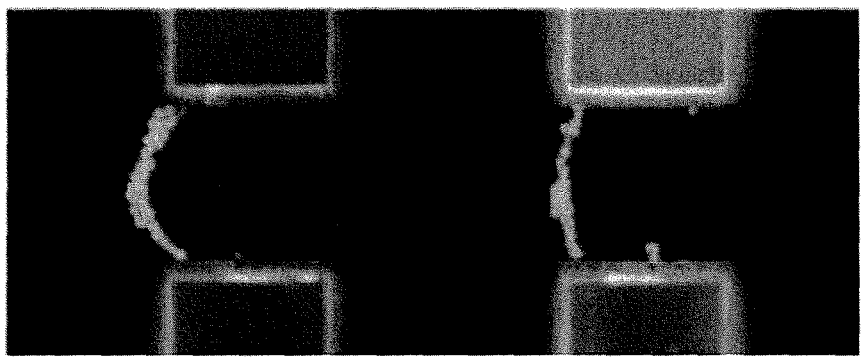
Figure 32C:

When 80% trapping was observed, cells closest to the channel wall were trapped while those closer to the center of the channel were not; a result predicted by the numerical modeling presented in FIG. 29c. These simulations further indicated that at low frequencies (≤100 kHz) the gradient of the electric field inside the main channel would not be sufficient for DEP cell manipulation and this was confirmed in the experiments. The minimum frequency necessary to achieve an 80% trapping efficiency is given in FIG. 31a as a function of applied voltage. Cell lysing was observed for 75 Vrms, 100 Vrms, 125 Vrms, and 150 Vrms at 296 kHz, 243 kHz, 197 kHz, and 173 kHz respectively. No lysing was observed at 50 Vrms within the frequency limits of the power supply. The concentration of live THP-1 cells using a 150 kHz voltage signal at 100 Vrms in device 1 is shown in FIG. 32.

Figure 30C:
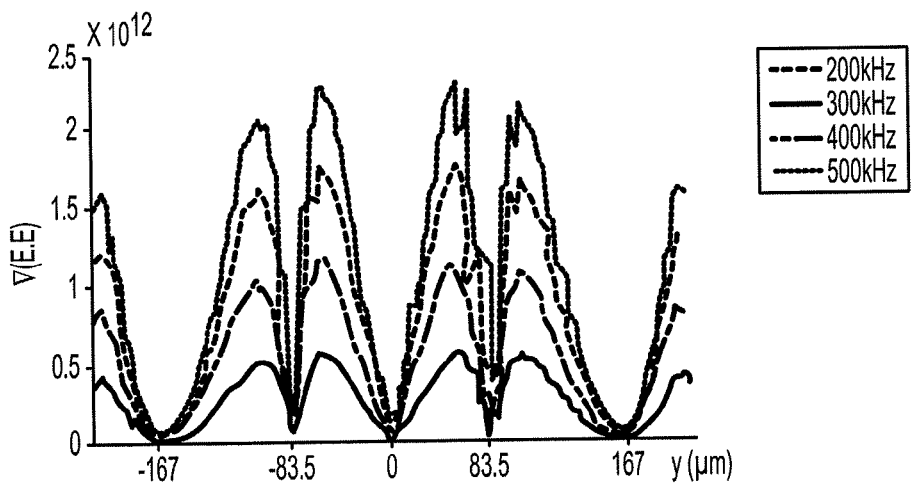
FIG. 30C shows a line plot of the gradient of the electric field squared ($kg^2mC^{-2}S^{-4}$) for four different electrical boundary conditions with efficient numerical cell trapping (V1=30 Vrms at 200 kHz, 300 kHz, 400 kHz, and 500 kHz, and V2=Ground) along the y axis (x=0).

Device 2: Numerical modeling proven valid for device 1 was used to predict the performance of device 2. The gradient of the electric field along the x-axis (y=0) of the main channel of device 2 is plotted in FIG. 3h. Again, for these electrical boundary conditions (V1=30 Vrms at 200 kHz, 300 kHz, 400 kHz, and 500 kHz and V2=Ground) cell trapping was observed. Local maximums in the gradient of the electric field occurred in line with the edges of the insulating pillars while the minimum gradient was experienced as cells passed through the region between two pillars. The highest electric field gradient was observed to occur at the two insulating pillars which had edges in the center of the device. The electric field gradients in the center of device 2 along the y-axis (x=0) are shown in FIG. 30c and the highest gradient was observed in line with the edges of the insulating pillars. It should be noted that the maximum gradient is observed at y=+/−83.5 μm and cells traveling through the exact center of the device (along the x-axis) experience a lower DEP force than those just off-center. The electric field gradient within the channel increased with applied signal frequency from 200 kHz to 500 kHz. This increase in gradient is not linear and these parameters represent the limitations of the current electrical setup.

Figure 31B:
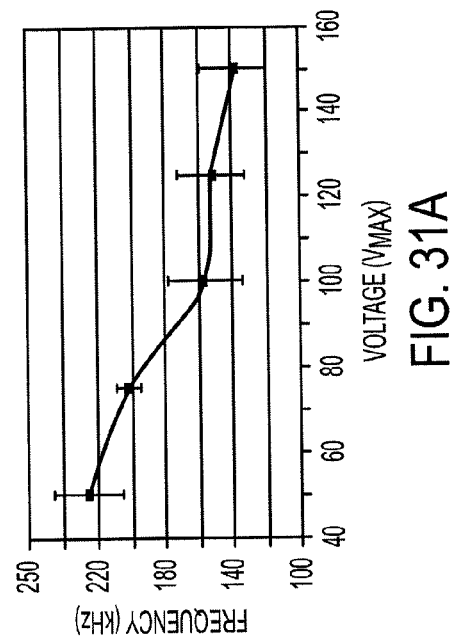
Figure 31C:
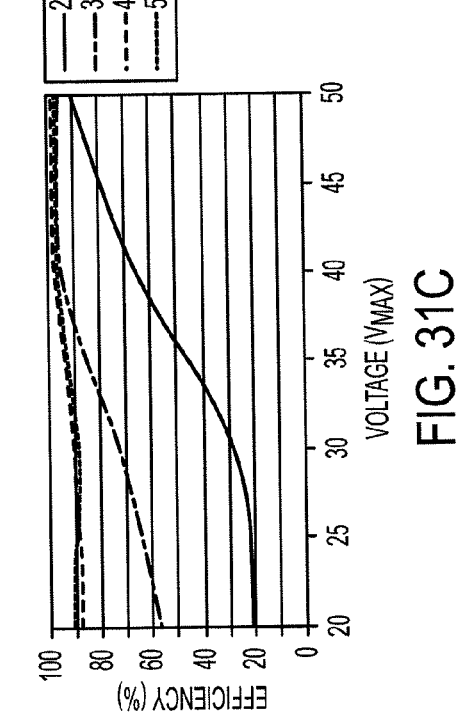
Figure 31D:
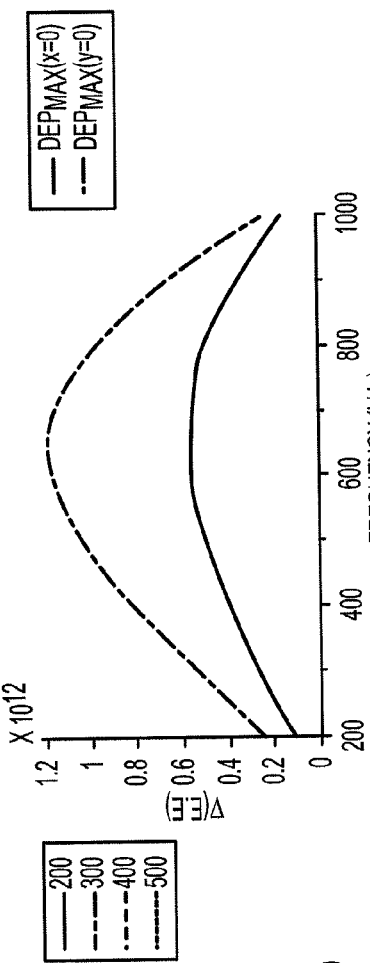

Theoretically, device 2 has a maximum gradient of electric field within the channel occurring between 600 kHz and 700 kHz as seen in FIG. 31d. Above this frequency, leakages in the system begin to dominate the response and the electric field within the channel drops off.

Live THP-1 cells were observed to experience positive DEP force at the reported frequencies and the DEP force applied on dead cells appeared to be negligible. In device 2, the majority of cell trapping was observed in the region between the first two columns of insulating barriers at 0.02 mL/hour. However, the distribution of trapped cells became more uniform at higher flow rates. At 0.02 mL/hour, trapping efficiencies greater than 90% were observed at all tested frequencies (200 kHz, 300 kHz, 400 kHz, and 500 kHz). However, lysing was seen at all frequencies when a voltage of 50 Vrms was applied. At the highest two frequencies, lysing was seen at 40 Vrms and over 10% of the cells lysed at 50 Vrms (FIG. 31c). Aside from lysing, the maximum voltage which may be applied to these devices is determined by the electrical breakdown voltage of the PDMS composing the barriers. These results suggest that the performance of the cDEP devices is comparable to and maybe able to exceed what is currently attainable and has been reported with DEP or iDEP 44-47.

In device 2, a maximum of 50 Vrms was applied to the inlets of the electrode channels. In device 2, a maximum of 50 Vrms at 500 kHz signal was applied to the inlets of the electrode channels. Because the sample channel is non-uniform, it was found through the numerical results that the actual electric field experienced by cells within the channel was between 20V/cm and 200V/cm. However, there are minute regions at the sharp corners inside the main channel with a high electric field intensity (350V/cm) that induces electroporation (IRE), which is what was observed during the experiments. This was caused by the dramatic change in the thickness of the PDMS barrier in those locations. It was in these small regions which cell lysing was most commonly seen.

Trapping efficiency experiments for higher flow rates were conducted at 500 kHz and 30 Vrms because these parameters yielded a high trapping efficiency of 89.6% at 0.02 mL/hour. Trapping efficiency was reduced by an increase in flow rate and reached a minimum of 44.8% (+/−14.2) at 0.8 mL/hour (FIG. 31b). Flow rates greater than 0.1 mL/hour were not reported due to limitations of the recording software that resulted in the inability to accurately count the number of cells entering and exiting the trapping region of the device.

Figure 33A:
FIGS. 33A-C show images of experimental results for device 2 of Example 2: (A) Dead and live THP-1 cells are moving left to right due to pressure driven flow; (B) 30 seconds after applying the electric field (V1=40$V_{rms}$ at 500 kHz and V2=Ground) live cells were trapped due to positive DEP but dead cells pass by; (C) Releasing the trapped live cells by turning off the power supply.
Figure 33B:
Figure 33C:
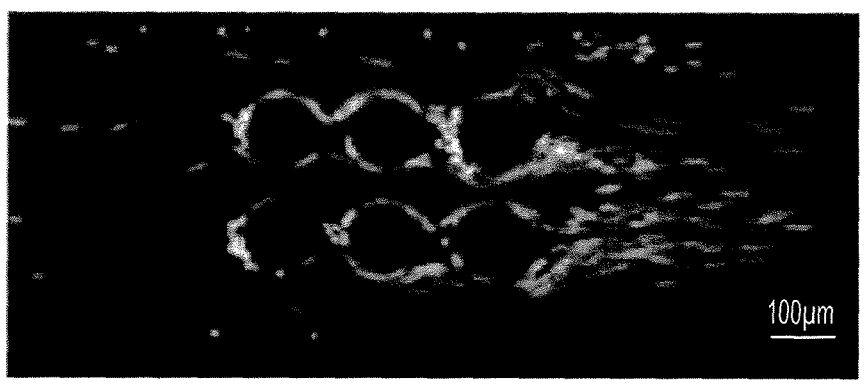

Due to the capacitance effect of the PDMS barriers in cDEP devices, the corresponding gradient of the electric field for voltage-frequency pairs are different for each design. These devices were designed to provide a sufficient gradient of the electric field for DEP cell manipulation within the limitations of the power supply and the PDMS breakdown voltage. The high trapping efficiency makes device 2 an optimal design for selective entrapment and enrichment of cell samples. This process is depicted in FIG. 33; initially live cells and dead cells passed through the trapping region due to pressure driven flow (FIG. 33). Live cells were selectively concentrated in the trapping region under the application of a 500 kHz, 40 Vrms signal (FIG. 33b). Under these parameters, the DEP force on the dead cells was not sufficient to influence their motion and they passed through the trapping region. The enriched sample of live cells can be controllably released for later analysis once the electric field is turned off (FIG. 33c).

Conclusion

This work has demonstrated the ability of cDEP to selectively concentrate specific cells from diverse populations through the separation of viable cells from a sample containing both viable and non-viable human leukemia cells. Repeatability, high efficiency, sterility, and an inexpensive fabrication process are benefits inherent to cDEP over more conventional methods of cell separation. This method is also unique in that direct evaluation is possible with little or no sample preparation. The resulting time and material savings are invaluable in homeland security and biomedical applications. Given cDEP's numerous advantages, the technique has tremendous potential for sample isolation and enrichment for drug screening, disease detection and treatment, and other lab-on-a-chip applications.

Example 3

Biological Particle Enrichment Utilizing cDEP

Introduction

The selective separation of target particles from a sample solution is an indispensable step in many laboratory processes [1]. Sensitive analysis procedures, especially those in the biomedical field, often require a concentration procedure before any analysis is performed. Several methods to perform this concentration have arisen including: density gradient based centrifugation or filtration [57], fluorescent and magnetic activated cell sorting, cell surface markers [55], and laser tweezers [79]. While, each of these techniques is unique in its inherent advantages and disadvantages, all are forced to compromise between high sample throughput and highly specific isolation. The more selective of these techniques oftentimes require extensive sample preparation before being performed. If the automation of laboratory analysis procedures is to be facilitated, a concentration technique capable of high sample throughput as well as highly specific concentration is critical.

Dielectrophoresis (DEP), or the motion of a particle due to its polarization in a non-uniform electric field, has shown great potential as a method for sample concentration [28, 29]. Typically, sample concentration through DEP involves the placement of an array of interdigitated electrodes under a microfluidic channel through which the sample fluid is passing. This electrode array creates a non-uniform electric field in the channel with which passing cells or micro-particles interact. DEP-based concentration techniques benefit from the fact that particles are isolated based upon their physical characteristics; allowing these techniques to be extremely specific without extensive sample preparation.

Microdevices employing interdigitated electrode arrays have proven the technique to be a viable method to rapidly and reversibly isolate cells and micro-particles from a solution. Examples of the successful use of DEP include the separation of human leukemia cells from red blood cells in an isotonic solution [7] and the entrapment of human breast cancer cells from blood [8]. DEP has additionally been found effective to separate neuroblastoma cells from HTB glioma cells [9], isolate cervical carcinoma cells [10], K562 human CML cells [11], and to separate live yeast cells from dead [12].

Unfortunately, by requiring the fabrication of an electrode array within the microfluidic channel, traditional DEP does not lend itself to mass fabrication techniques such as injection molding. Insulator-based Dielectrophoresis (iDEP) seeks to simplify the fabrication required to perform DEP-based concentration in order to facilitate more widespread usage. iDEP relies upon the presence of insulating structures in the microfluidic channel to create non-uniformities in the electric field necessary for DEP [38, 51]. These insulating structures are typically patterned in the same process as the microfluidic channel itself; thus, iDEP naturally lends itself to mass production systems such as injection molding and hot embossing [35]. iDEP has been demonstrated in combination with other forms of on-chip analysis, such as impedance detection [36], to form fully integrated systems.

While iDEP provided an excellent solution to the complex fabrication required by traditional DEP devices, it is difficult to utilize for biological fluids. The high electric field intensity employed by iDEP produces undesirable results such as joule heating, bubble formation, and electrochemical effects when the sample solution is of high conductivity [37]. In addition, the electrode placement at the channel inlet and outlet necessitates the presence of large reservoirs at these locations to mitigate electrolysis effects. These reservoirs have the negative consequence of re-diluting the sample after it has passed through the region of concentration, further complicating the extraction of a sample for off-chip analysis. For DEP to truly represent an attractive alternative to traditional sample concentration techniques, it must be devoid of these negative influences upon the sample and yet retain a simplified fabrication process.

A third manifestation of DEP, contactless dielectrophoresis (cDEP), employs the simplified fabrication processes of iDEP yet lacks the problems associated with the electrode-sample contact [80]. cDEP relies upon reservoirs filled with highly conductive fluid to act as electrodes and provide the necessary electric field. These reservoirs are placed adjacent to the main microfluidic channel and are separated from the sample by a thin barrier of a dielectric material as is shown in FIG. 1h. The application of a high-frequency electric field to the electrode reservoirs causes their capacitive coupling to the main channel and an electric field is induced across the sample fluid. Similar to traditional DEP, cDEP exploits the varying geometry of the electrodes to create spatial non-uniformities in the electric field. However, by utilizing reservoirs filled with a highly conductive solution, rather than a separate thin film array, the electrode structures employed by cDEP can be fabricated in the same step as the rest of the device; hence the process is conducive to mass production [80].

A cDEP device is presented that demonstrates the enrichment abilities and rapid fabrication advantages of the cDEP technique. A microfluidic device was fabricated by creating a PDMS mold of a silicon master produced by a single-mask photolithographic process. This device has shown the ability of cDEP to separate live cells from dead [47] a powerful capability of DEP systems[67-70, 81]. In order to demonstrate the concentration abilities of cDEP, this microfluidic device was used to enrich THP-1 human leukemia cells and 2-µm polystyrene beads from a background media. The device exhibited the ability to concentrate THP-1 cells through positive DEP and 2 µm beads via negative DEP. This is the first cDEP microfluidic device presenting negative DEP. Furthermore, the use of a silicon master stamp allows for the large-scale reproduction of the device. These experiments illustrate that the use of cDEP as an expedited process for sample concentration and enrichment, which may have an immense impact in biomedical and homeland security applications where rapid, accurate results are extremely valuable.

Theory

The time-average dielectrophoretic force acting on a spherical particle exposed to a non-uniform electric field is described as [1, 28, 29, 71]

$$F_{DEP} = \pi \in_m r^3 Re[f_{CM}] \nabla \|E\|^2 \quad (1)$$

where $\in_m$ is the permittivity of the suspending medium, r is the radius of the particle, $\nabla \|E\|^2$ defines the local electric field gradient, Re[ ] represents the real part, and $f_{CM}$ is the Clausius-Mossotti factor given by $$f_{CM} = \frac{\varepsilon_p^* - \varepsilon_m^*}{\varepsilon_p^* + 2\varepsilon_m^*} \quad (2)$$

where $\in_p^*$ and $\in_m^*$ are the particle and the medium complex permittivity respectively. The complex permittivity is defined as follows:

$$\varepsilon^* = \varepsilon - j\frac{\sigma}{\omega} \quad (3)$$

where $\in$ is the permittivity, $\sigma$ is the conductivity, $j^2 = -1$, and $\omega$ is the angular frequency. The hydrodynamic drag force on a spherical particle due to its translational movement in a suspension is given by:

$$f_{Drag} = 6\eta r \pi (u_p - u_f) \quad (4)$$

where r is the particle radius, $\eta$ is the medium viscosity, $u_p$ is the velocity of the particle, $u_f$ is the medium velocity. Assuming that the acceleration term can be neglected, the magnitude of the velocity of the particle is determined by a balance between the DEP force and Stoke's drag force.

$$u_p = u_f - \mu_{DEP} \nabla (E \cdot E) \quad (5)$$

The above equations are valid for spherical micro-particles, however, others have demonstrated that similar equations can be attained for other geometries, e.g., cylindrical particles [82]. In addition, researchers have employed elegant shell models to determine an effective/equivalent complex conductivity for a particle consisting of several layers, e.g., a cell [83, 84].

The DEP force on a particle may be positive or negative depending on the relationship of the applied frequency to the particles DEP crossover frequency. DEP crossover frequency is the frequency in which the real part of the Clausius-Mossotti (C.M.) factor is equal to zero and is given by [1, 72]

$$\omega_c = \frac{1}{2\pi} \sqrt{\frac{(\sigma_m - \sigma_p)(\sigma_p + 2\sigma_m)}{(\epsilon_m - \epsilon_p)(\epsilon_p + 2\epsilon_m)}} \quad (6)$$

where $\omega_c$ is the crossover frequency and $\rho_p$ and $\rho_m$ are the conductivity of the particle and medium, respectively. This shows that DEP can be used to differentiate micro-particles based on their difference in C.M. factor by adjusting the frequency.

Methods

Microfabrication

Deep Reactive Ion Etching (DRIE) was used to etch a <100> silicon wafer to a depth of 50 µm (FIG. 34a-d) to form the master stamp. Oxide was then grown on the silicon master using thermal oxidation and removed using HF solvent to reduce surface "scalloping" caused by the DRIE process. This variation in the surface can greatly inhibit the removal of the cured mold from the stamp.

Figure 34G:
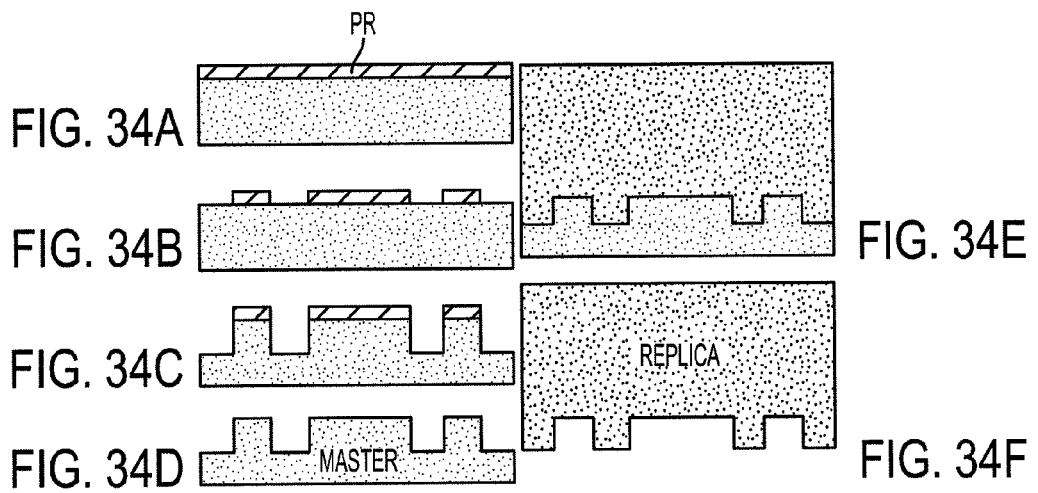
FIGS. 34A-F show a schematic of the fabrication process of Example 3. Steps A through D are followed only once in clean room to create a master stamp. Steps E and F are repeated to produce an indefinite number of experimental devices out of clean room and in lab.
Figure 34G:
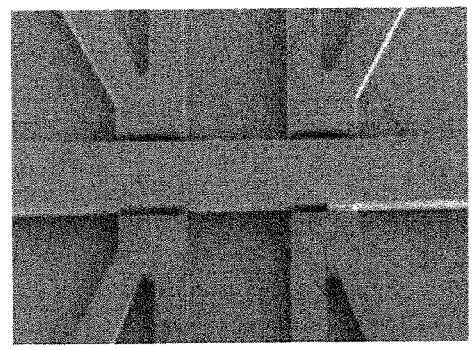
Figure 34H:
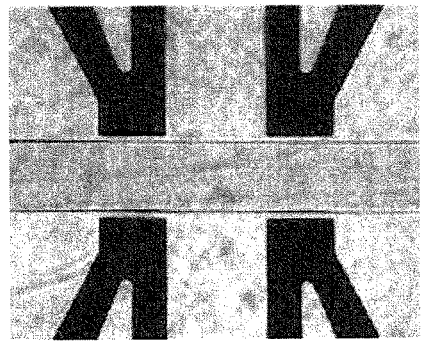

Liquid polydimethylsiloxane (PDMS) used for the molding process was composed of PDMS monomers and a curing agent in a 10:1 ratio (Sylgrad 184, Dow Corning, USA). The mixture was de-gassed in a vacuum for 15 minutes. The de-gassed PDMS liquid was then poured onto the silicon master and cured for 45 min at 100° C. (FIG. 1e). The solidified PDMS was removed from the mold and fluidic connections to the channels were punched with 15 gauge blunt needles (Howard Electronic Instruments, USA). Cleaned glass microscope slides and the PDMS replica were bonded after exposure to oxygen plasma for 40 s at 50 W RF power (FIG. 34f). A SEM image of the trapping zone of the device replica on the silicon master is shown in FIG. 34 g. FIG. 1h shows the fabricated device at the zone of trapping. The main and electrode channels were filled with yellow and blue dyes respectively to improve imaging of the fluidic structures. A schematic with dimensions is presented in FIG. 35. The thickness of the PDMS barrier between the side channels and the main channel is 20 µm.

Cells/Beads and Buffer

Live samples of THP-1 human Leukemia monocytes were washed twice and resuspended in the prepared buffer (8.5% sucrose [wt/vol], 0.3% glucose [wt/vol], and 0.725% [wt/vol] RPMI) [74] to achieve $10^6$ cells/ail cell concentration. The electrical conductivity of the buffer was measured with a Mettler Toledo SevenGo pro conductivity meter (Mettler-Toledo, Inc., Columbus, Ohio) to ensure that its conductivity was 130 µS/cm. These cells were observed to be spherical with a diameter of ~13 µm when in suspension.

Carboxylate-modified polystyrene microspheres (Molecular Probes, Eugene, Oreg.) having a density of 1.05 mg/mm³ and diameters of 2 µm and 10 µm were utilized at a dilution of 2:1000 from a 2% by wt. stock suspension. Bead suspensions were sonicated between steps of serial dilution and before use. The background solution was deionized water with a conductivity of 86 µS/cm.

Live THP-1 cells were stained using cell trace calcein red-orange dye (Invitrogen, Eugene, Oreg., USA). The stained cell sample and the 10 µm beads sample were mixed in a ratio of 1:1.

Experimental Set-Up

The microfluidic devices were placed in a vacuum jar for 30 minutes prior to experiments to reduce problems associated with priming. Pipette tips inserted in the punched holes were used as reservoirs to fill the side channels with PBS. Pressure driven flow was provided in the main channel using a microsyringe pump. Inlet holes punched along the main channel of the device were connected to syringes via Teflon tubing (Cole-Parmer Instrument Co., Vernon Hills, Ill.). Once the main channel was primed with the cell suspension, the syringe pump was set to 1 ml/hr steadily decreasing the flow rate down to 0.02 ml/hr (20 µL/hr) equivalent to a velocity of ~550 µm/sec. This flow rate was maintained for 1 minute prior to experiments. An inverted light microscope equipped with color camera (DFC420, Leica DMI 6000B, Leica Microsystems, Bannockburn, Ill.) was used to monitor the cells flowing through the main channel. High-frequency electric fields were provided by a wideband, high-power amplifier and transformer combination (Amp-Line Corp., Oakland Gardens, N.Y.) and signal generation was accomplished using a function generator (GFG-3015, GW Instek, Taipei, Taiwan).

Numerical Modeling

The electric field distribution and its gradient $\nabla E = \nabla(\nabla \phi)$ were modeled numerically in Comsol multi-physics 3.5 using the AC/DC module (Comsol Inc., Burlington, Mass., USA). This is done by solving for the potential distribution, $\phi$, using the Laplace equation, $\nabla \cdot (\sigma^* \nabla \phi) = 0$, where $\sigma^*$ is the complex conductivity of the sub-domains of the microfluidic device. The boundary conditions used were prescribed uniform potentials at the inlet or outlet of the side channels. The electrical conductivity and the relative electrical permittivity of PDMS have been reported as $0.83 \times 10^{-12}$ S/m and 2.65 respectively (Sylgrad 184, Dow Corning, USA). The electrical conductivity of PBS and the DEP buffer are 1.4 S/m and 130 µS/cm respectively and a relative permittivity of 80.

Results

Numerical modeling was used to determine relevant experimental conditions such as applied voltage and frequency. Experimental values for the voltage and frequency must be chosen to provide sufficient DEP force on the target particles without exceeding the dielectric breakdown voltage of the PDMS barriers (280V for a 20 µm barrier). Due to the capacitive properties of the thin PDMS barrier between the side channels and the main channel, the induced electric field inside the main channel is strongly dependent on the frequency and the applied voltage. Hence, a minimum frequency is required to provide strong gradient of the electric field with respect to a specific voltage for micro-particle manipulation. A 70 $V_{rms}$ sinusoid at 300 kHz was found to provide significant DEP force in the microfluidic channel without damaging the device. This excitation signal was applied to the top two electrodes (electrodes 1 and 2) and the bottom two electrodes were grounded (electrodes 3 and 4). The electric field intensity surface plot in the main channel of the device at the experimental parameters is shown in FIG. 36a. It is important to note that the electric field intensity did not reach 0.1 kV/cm, the necessary field strength to kill cells through irreversible electroporation. Electroporation is a phenomenon that increases the permeabilization of the cell membrane by exposing the cell to an electric field [85-87]. In irreversible electroporation, permanent pores open in the cell membrane which leads to cell death [86, 88].

The trapping regions and cell's trajectory through the microfluidic device can be predicted using the numerical modeling as DEP cell manipulation is strongly dependent on the gradient of the electric field. The highest gradient of the electric field is estimated to appear at the edges of the side channels as shown by numerical results found in FIG. 3b. However, there is still a sufficient gradient of the electric field at the middle of the channel to manipulate the micro-particles. To clarify this, the same numerical results for the gradient of the electric field surface plot, but with a different representing range were shown in FIG. 36c.

The DEP force is acting on the cell/micro-particle in both x and y directions. The gradient of the x-component of the electric field, which causes DEP force in the x-direction, is shown in FIG. 4a for an applied signal of 70 $V_{rms}$ and 300 kHz at three different distances from the channel wall. In order to trap target cells, the x-component of the DEP force should overcome the hydrodynamic drag force. The x-component of the DEP force along the centerline of the main channel is negligible compared to the DEP force along the channel wall. Furthermore, this force is the strongest along the edges of the side channel walls (x=−350, −150, 150, 350 µm). The y-component of the gradient of the electric field at different distances from the origin (FIG. 35, x=0, 150, 250, 350, and 450 is also shown in FIG. 37b. These results show that the y-component of the DEP force is negligible for the particles along the lines x=0 and x=250 compared to the other positions and also indicate that y-component of the DEP force is the strongest along the edges of the side channels (x=−350, −150, 150, 350 While the x-component of the DEP force along the centerline of the main channel is almost negligible (FIG. 37a), the y-component of the DEP force, will pull particles off the centerline of the main channel and towards the channel walls in the case of positive DEP.

Figure 38A:
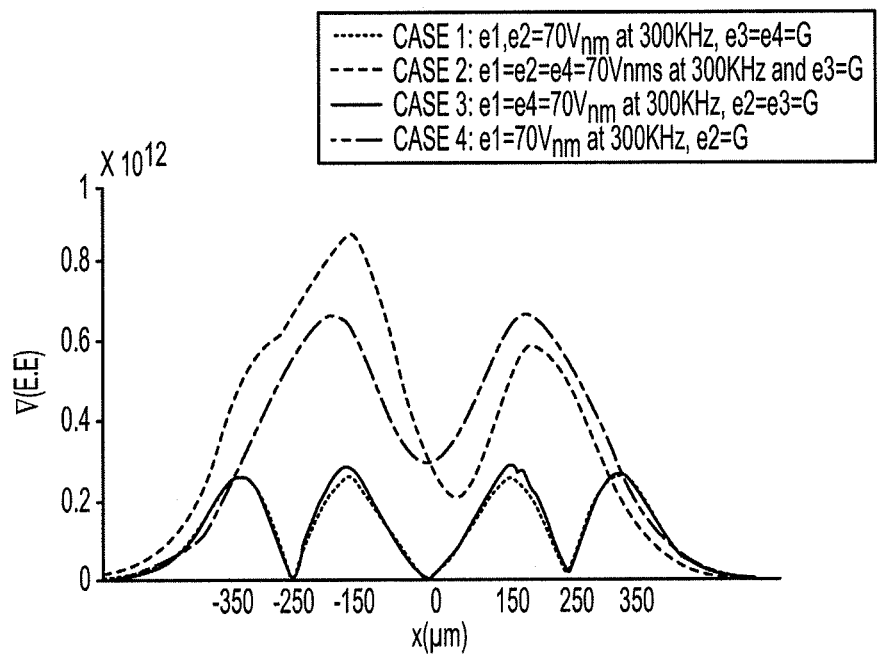
FIGS. 38A and B show the gradient of the electric field intensity along the centerline of the main channel for different electrode configurations. The electrodes are charged with 70 Vrms and 300 kHz in the side channels in all cases. Case 1: charged electrodes are in channels 1 & 2 and ground electrodes are in channels 3 & 4, Case 2: charged electrodes are in channels 1, 2 & 4 and ground electrodes are in channels 3, Case 3: charged electrodes are in channels 1 & 4 and ground electrodes are in channels 2 & 3, Case 4: charged electrodes are in channel 1 and ground electrodes are in channel 2.
Figure 38B:
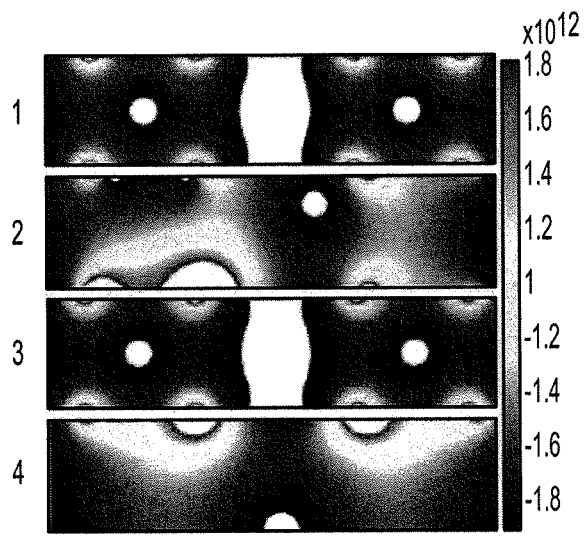
FIG. 38B shows an electric field intensity surface plot.

The effect of varying the electrode configuration on the gradient of the electric field along the centerline of the main channel was also investigated. Four different configurations with the same applied voltage and frequency were studied and the results shown in FIG. 38. The DEP effects caused by having electrodes 1 and 2 charged and electrodes 3 and 4 grounded (case 1) are similar to the configuration with electrodes 1 and 4 charged and electrodes 2 and 3 grounded (case 3). The same can be said for the cases with electrodes 1, 2, and 4 charged (case 2) and electrode 3 grounded or electrode 1 charged and electrode 2 grounded (case 4). The surface plot of the gradient of the electric field with respect to these four cases of the electrode configurations were shown in FIG. 38b.

These numerical results indicate that the electrode configuration has a substantial effect on the gradient of the electric field and the resulting DEP cell manipulation. A benefit of this analysis is that one may change the cell/particle manipulation strategy by changing the electrode configurations. For example, the configuration used in case 4 (electrodes on just one side of the main channel) can deflect the target cell/particle trajectory in the main channel such that it leads to a specific reservoir.

Figure 39:
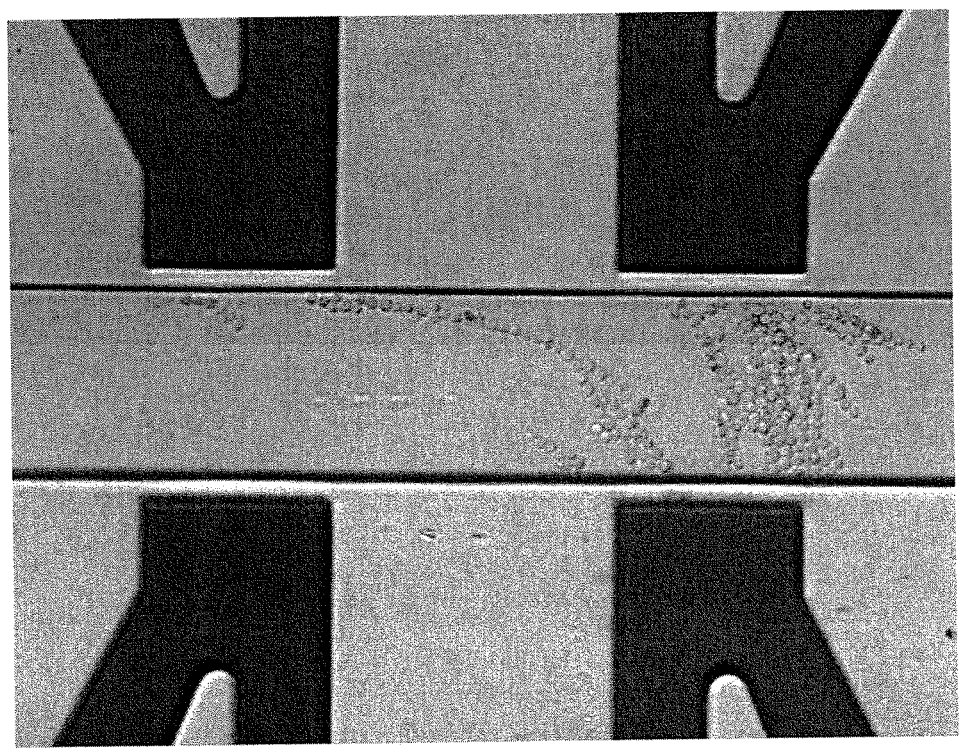
FIG. 39 shows an image of experimental results from Example 3, a bright field image of live THP-1 cells, shown here 30 seconds after applying the electric field (V1=V2=70 Vrms at 300 kHz and V3=V4=Ground). The cells were trapped due to positive DEP.

The validity of the numerical modeling was confirmed by demonstrating the system's ability to concentrate particles through both positive and negative DEP. Live THP-1 cells were observed to be trapped efficiently due to positive DEP force at $V_1 = V_2 = 70$ $V_{rms}$ at 300 kHz, $V_3 = V_4 =$ Ground (FIG. 39). Particles parallel to the electric field attract each other due to dipole-dipole interaction, resulting in pearl-chain formations of the trapped cells in the direction of the electric field [29, 53, 66]. Referring to FIG. 36b, particles concentrated through positive DEP should show a predisposition to group at locations with a high gradient of the electric field, in this case at the edges of the electrode reservoirs. As can be seen in FIG. 39, this is indeed the case. The pearl chain formations attach to the side wall at locations with a high gradient of the electric field and then spread towards the center of the channel.

Figure 40A:
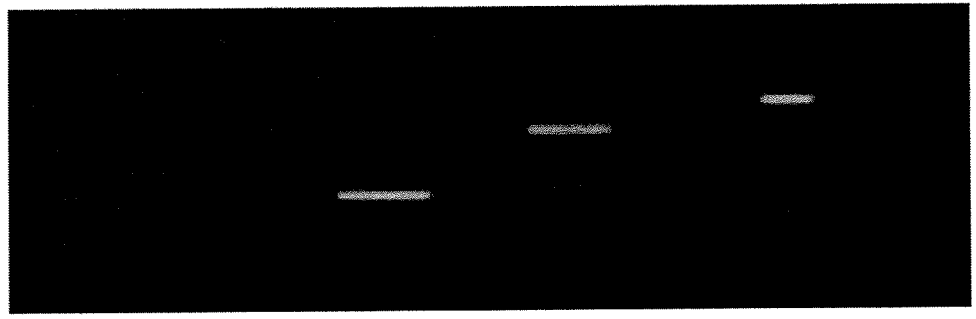
FIGS. 40A-C show images of experimental results from Example 3: selective trapping of live THP-1 cells from a mixture also containing 10 µm polystyrene beads. THP-1 live cells were stained using cell trace calcein red-orange dye (A) Cells and beads are moving from right to left due to pressure driven flow. (B) THP-1 cells are trapped via dielectrophoresis and beads are passing through the trapping zone. Charged electrodes are in channels 1 & 2 (V1=V2=70 Vrms) at 300 kHz and ground electrodes are in channels 3 & 4 (V3=V4=G). (C) Releasing the trapped cells.
Figure 40B:
Figure 40C:
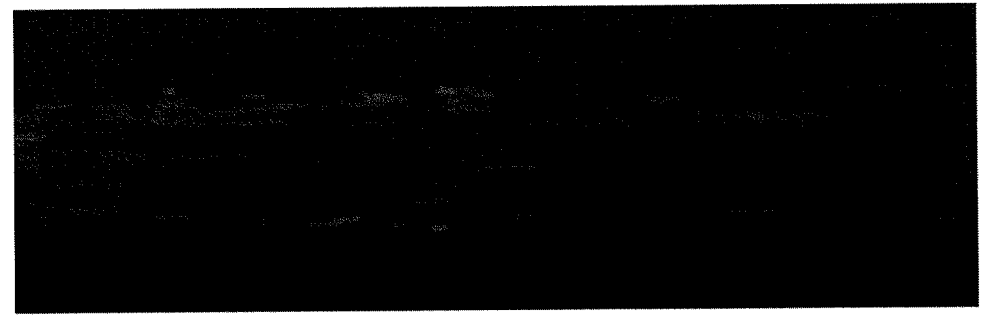
Figure 41A:
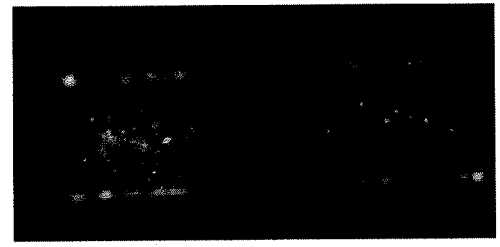
FIGS. 41A-D show images of experimental results from Example 3: trapping 2 µm beads suspended in DI water (V1=V2=190 Vrms at 300 kHz and V3=V4=Ground) (A) t=0 (B) t=30 Seconds (C) t=50 Seconds (D) t=1 min, Release.
Figure 41B:
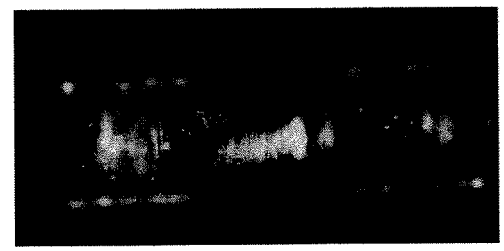
Figure 41C:
Figure 41D:
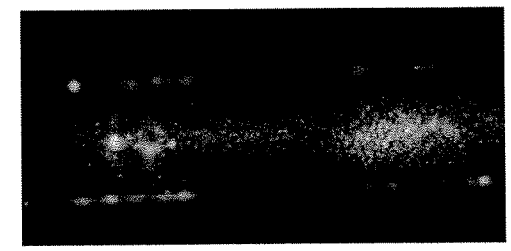

The selectivity of the device to differentiate two different particles with almost the same size was also examined via separation of THP-1 cells from 10 µm beads. The THP-1 cells were observed to be trapped at 70 Vrms and 300 kHz and the 10 µm beads went through the main channel without significant DEP disturbance (FIG. 40). However, in order to increase the trapping efficiency, the voltage and/or frequency of the applied signal should be increased such that the particles passing through the middle of the channel experience strong DEP effect. At these higher voltage/frequencies that both cells and beads close to the channel walls were observed to be trapped, reducing the device's selectivity. This effect may be attributed to the non-uniform gradient of the electric field across the main channel and between the side channels.

Particle concentration through negative DEP was displayed using 2 µm beads suspended in DI water at $V1=V2=190$ $V_{rms}$ at 300 kHz and $V3=V4=$Ground. These experimental results are shown in FIG. 41. As is consistent with a negative DEP response, the beads grouped in regions away from high gradients of the electric fields which, in this case, is in the centerline of the channel (FIGS. 40b and c). The inability to focus the microscope on all of the trapped beads simultaneously indicates that the beads were trapped at multiple heights in the main channel.

Discussion

The use of a straight channel in this design has several advantages over more complicated configurations. The trajectory of a particle, without DEP influence, is easily predicted and the lack of detailed features simplifies production and replication of the devices. This same lack of complicated features in the channel helps to mitigate fouling effects caused by cell trapping. However, it should be noted that the DEP effect may be reduced significantly at the middle of the channel for wider channels. One method of addressing this negative effect is to use insulating structures inside the main channel. These structures distort the electric field and provide a sufficient gradient for DEP manipulation of cells passing through the center of the channel. These types of designs may help increase the throughput and trapping efficiency of cDEP devices.

The device presented in this paper exhibited the concentration of microparticles at specific trapping regions within the device during the application of an electric field. The removal of this electric field allows the trapped cells to flow from the device at an increased concentration and these cells may be diverted to a separate reservoir off chip. This "trap and release" concentration strategy can also be incorporated with on-chip analysis systems by diverting the concentrated group of cells into a side channel as has been illustrated with iDEP [36].

Forthcoming generations of cDEP devices may also utilize a "chip and manifold" configuration relying upon disposable, injection molded "chips" inserted into a reusable manifold containing the necessary fluidic and electrical connections. This arrangement would allow metal electrodes in the manifold to be re-used for thousands of experiments while shifting the manufacturing burden to the replication of inexpensive fluidic chips. This use of polymer chips manufactured through injection molding has been demonstrated previously for iDEP[36].

Conclusion

A microfluidic system was presented that illustrates the great potential for DEP-based concentration of biological particles without negative effects on the sample, extensive sample preparation, or complicated fabrication procedures. Numerical modeling revealed the flexibility of this system's multiple electrode configurations to divert the particles into a desired trajectory and the device showed the ability to concentrate micro-particles through both positive and negative DEP. By relying upon the particle's electrical properties to accommodate enrichment, cDEP should be able to achieve a high degree of specificity without extensive sample preparation.

The potential for batch fabrication illustrated in this work, combined with the high performance of the resulting devices makes cDEP an attractive candidate for pre-concentration processes in areas where both rapid and highly accurate results of analyses are required.

Example 4

Continuous Separation of Beads and Human Red Blood Cells

The single layer device embodiment depicted in FIG. 42 consists of a T-channel 4217 and two electrode channels 4213, 4215. An exploded view of the area in the box in FIG. 42A is shown in FIG. 42B. In the schematic in FIG. 42A, samples are introduced from left to right via pressure driven flow. When an AC electric signal of 100 Vrms at 400 kHz is applied across the fluid electrodes 4213, 4215, 4 micron beads can be isolated from 2 micron beads, concentrated, and released as shown in FIGS. 6 C and D. When an AC signal of 60V at 500 kHz is applied, human red blood cells are separated from a buffer solution as shown in FIG. 42E. In this device described in this example, particles are continuously separated from the bulk solution and diverted into a separate microfluidic channel. Devices similar to this can be used to enhance microfluidic mixing.

REFERENCES

1. Morgan, H. and N. G. Green, AC Electrokinetics: Colloids and Nanoparticles. 2003, Hertfordshire, England: Research Studies Press LTD. 324.
2. Lapizco-Encinas, B. H., et al., Dielectrophoretic concentration and separation of live and dead bacteria in an array of insulators. Anal Chem, 2004. 76(6): p. 1571-9.
3. Armstrong, D., et al., Rapid CE microbial assays for consumer products that contain active bacteria. FEMS Microbiology Letters, 2001. 194(1): p. 33-37.
4. Armstrong, D., et al., Separating microbes in the manner of molecules. 1. Capillary electrokinetic approaches. Analytical Chemistry, 1999. 71(24): p. 5465-5469.
5. Girod, M. and D. W. Armstrong, Monitoring the migration behavior of living microorganisms in capillary electrophoresis using laser-induced fluorescence detection with a charge-coupled device imaging system. Electrophoresis, 2002. 23(13): p. 2048-56.
6. Cabrera, C. R. and P. Yager, Continuous concentration of bacteria in a microfluidic flow cell using electrokinetic techniques. Electrophoresis, 2001. 22(2): p. 355-62.
7. Becker, F. F., et al., The removal of human leukaemia cells from blood using interdigitated microelectrodes. J. Phys. D: Appl. Phys., 1994. 27: p. 2659-2662.
8. Gascoyne, P. R. C., et al., Dielectrophoretic Separation of Cancer Cells from Blood. IEEE Trans. Industry Applications, 1997. 33(3): p. 670-678.
9. Huang, Y., et al., Dielectrophoretic cell separation and gene expression profiling on microelectronic chip arrays. Anal Chem, 2002. 74(14): p. 3362-71.

10. Cheng, J., et al., Isolation of cultured cervical carcinoma cells mixed with peripheral blood cells on a bioelectronic chip. Anal Chem, 1998. 70(11): p. 2321-6.
11. Altomare, L., et al., Levitation and movement of human tumor cells using a printed circuit board device based on software-controlled dielectrophoresis. Biotechnol Bioeng, 2003. 82(4): p. 474-9.
12. Markx, G. H., M. S. Talary, and R. Pethig, Separation of viable and nonviable yeast using dielectrophoresis. Journal of Biotechnology, 1994. 32(1): p. 29-37.
13. Das, C. M., et al., Dielectrophoretic segregation of different human cell types on microscope slides. Anal Chem, 2005. 77(9): p. 2708-19.
14. Gascoyne, P. R., et al., Isolation of rare cells from cell mixtures by dielectrophoresis. Electrophoresis, 2009. 30(8): p. 1388-98.
15. Apostolaki, S., et al., Circulating HER2 mRNA-positive cells in the peripheral blood of patients with stage I and II breast cancer after the administration of adjuvant chemotherapy: evaluation of their clinical relevance. Ann Oncol, 2007. 18(5): p. 851-8.
16. Cristofanilli, M., The "microscopic" revolution in breast carcinoma. Cancer, 2005. 103(5): p. 877-80.
17. Fizazi, K., et al., High detection rate of circulating tumor cells in blood of patients with prostate cancer using telomerase activity. Ann Oncol, 2007. 18(3): p. 518-21.
18. Hayes, D. F., et al., Circulating tumor cells at each follow-up time point during therapy of metastatic breast cancer patients predict progression-free and overall survival, Clin Cancer Res, 2006. 12(14 Pt 1): p. 4218-24.
19. Naoe, M., et al., Detection of circulating urothelial cancer cells in the blood using the CellSearch System. Cancer, 2007. 109(7): p. 1439-45.
20. Osman, I., et al., Detection of circulating cancer cells expressing uroplakins and epidermal growth factor receptor in bladder cancer patients. International Journal of Cancer, 2004. 111(6): p. 934-939.
21. Galan, M., et al., Detection of occult breast cancer cells by amplification of CK19 mRNA by reverse transcriptase-polymerase chain reaction: Role of surgical manipulation. Anticancer Research, 2002. 22(5): p. 2877-2884.
22. Dingemans, A. M. C., et al., Detection of cytokeratin-19 transcripts by reverse transcriptase-polymerase chain reaction in lung cancer cell lines and blood of lung cancer patients. Laboratory Investigation, 1997. 77(3): p. 213-220.
23. Berteau, P., et al., Molecular detection of circulating prostate cells in cancer II: Comparison of prostate epithelial cells isolation procedures. Clinical Chemistry, 1998. 44(8): p. 1750-1753.
24. Berteau, P., et al., Influence of blood storage and sample processing on molecular detection of circulating prostate cells in cancer. Clinical Chemistry, 1998. 44(3): p. 677-679.
25. Koike, E., et al., Endoscopic ultrasonography in patients with thyroid cancer: Its usefulness and limitations for evaluating esophagopharyngeal invasion. Endoscopy, 2002. 34(6): p. 457-460.
26. Schroder, C. P., et al., Detection of micrometastatic breast cancer by means of real time quantitative RT-PCR and immunostaining in perioperative blood samples and sentinel nodes. International Journal of Cancer, 2003. 106(4): p. 611-618.
27. Traweek, S. T., J. Liu, and H. Battifora, KERATIN GENE-EXPRESSION IN NONEPITHELIAL TISSUES—DETECTION WITH POLYMERASE CHAIN-REACTION. American Journal of Pathology, 1993. 142 (4): p. 1111-1118.
28. Pohl, H., The Motion and Precipitation of Suspensoids in Divergent Electric Fields. Applied Physics, 1951. 22: p. 869-871.
29. Pohl, H. A., Some Effects of Nonuniform Fields on Dielectrics. J. Appl. Phys., 1958. 29: p. 1182-1188.
30. Pohl, H., Dielectrophoresis. Cambridge University Press: Cambridge, 1978. 1978.
31. Davalos, R. V. and B. Rubinsky, Electrical impedance tomography of cell viability in tissue with application to cryosurgery. Journal of Biomechanical Engineering, 2004. 126(2): p. 305-309.
32. Jen, C. P. and T. W. Chen, Selective trapping of live and dead mammalian cells using insulator-based dielectrophoresis within open-top microstructures. Biomed Microdevices, 2009. 11(3): p. 597-607.
33. Steffen Hardt, F. S., Microfluidic Technologies for Miniaturized Analysis Systems. Book, ed. S. D. Senturia. 2007: Springer.
34. Hughes, M. P., Strategies for dielectrophoretic separation in laboratory-on-a-chip systems. Electrophoresis, 2002. 23(16): p. 2569-82.
35. Simmons, B. A., et al., The development of polymeric devices as dielectrophoretic separators and concentrators. MRS Bulletin, 2006. 31(2): p. 120-124.
36. Sabounchi, P., et al., Sample concentration and impedance detection on a microfluidic polymer chip. Biomed Microdevices, 2008. 10(5): p. 661-70.
37. Kang, Y., et al., DC-Dielectrophoretic separation of biological cells by size. Biomed Microdevices, 2008. 10(2): p. 243-9.
38. Cummings, E. B. and A. K. Singh, Dielectrophoresis in microchips containing arrays of insulating posts: theoretical and experimental results. Anal Chem, 2003. 75(18): p. 4724-31.
39. Poorya Sabounchi, M. P. K., David E. Huber, Alison E. Harris, Blake A. Simmons, Joule Heating Effects on Insulator-based Dielectrophoresis. MicroTAS Conference, San Diego, 2008.
40. Shafiee, H., et al., Contactless dielectrophoresis: a new technique for cell manipulation. Biomed Microdevices, 2009. 11: p. 997-1006.
41. Borgatti, M., et al., Antibody-antigen interactions in dielectrophoresis buffers for cell manipulation on dielectrophoresis-based Lab-on-a-chip devices. Minerva Biotecnologica, 2007. 19(2): p. 71-74.
42. Del Bene, F., et al., A model-based approach to the in vitro evaluation of anticancer activity. Cancer Chemotherapy and Pharmacology, 2009. 63(5): p. 827-836.
43. Ntouroupi, T. G., et al., Detection of circulating tumour cells in peripheral blood with an automated scanning fluorescence microscope. British Journal of Cancer, 2008. 99(5): p. 789-795.
44. Sarantseva, S. V. and A. L. Schwarzman, Modern genetic approaches to searching for targets for medicinal preparations. Russian Journal of Genetics, 2009. 45(7): p. 761-770.
45. Tatosian, D. A. and M. L. Shuler, A Novel System for Evaluation of Drug Mixtures for Potential Efficacy in Treating Multidrug Resistant Cancers. Biotechnology and Bioengineering, 2009. 103(1): p. 187-198.
46. Leary, J. F., et al. High-throughput cell analysis and sorting technologies for clinical diagnostics and therapeutics. in Conference on Clinical Diagnostic Systems. 2001. San Jose, Calif.: Spie-Int Soc Optical Engineering.

47. Shafiee, H., et al., Selective isolation of live/dead cells using contactless dielectrophoresis (cDEP). Lab on a Chip, 2010: p.
48. Arnold, W. M. K. J. G. m. b. H., Juelich (Germany, F.R.). Inst. fuer Medizin); Zimmermann, U. (1982). "Rotating-field-induced rotation and measurement of the membrane capacitance of single mesophyll cells of Avena sativa" *Plant physiology and biochemistry* v. 37(10): 908-915.
49. Ashkin, A., J. M. Dziedzic and T. Yamane (1987). "Optical trapping and manipulation of single cells using infrared laser beams." *Nature* 330(6150): 769-71
50. Das, C. M., F. Becker, S. Vernon, J. Noshari, C. Joyce and P. R. Gascoyne (2005). "Dielectrophoretic segregation of different human cell types on microscope slides." *Anal Chem* 77(9): 2708-19.
51. Davalos, R. V., G. J. McGraw, T. I. Wallow, A. M. Morales, K. L. Krafcik, Y. Fintschenko, E. B. Cummings and B. A. Simmons (2008). "Performance impact of dynamic surface coatings on polymeric insulator-based dielectrophoretic particle separators." *Anal Bioanal Chem* 390(3): 847-855.
52. Davalos, R. V., I. L. Mir and B. Rubinsky (2005). "Tissue ablation with irreversible electroporation." *Ann Biomed Eng* 33(2): 223-31.
53. Dussaud, A. D. (2000). "Particle segregation in suspensions subject to high-gradient ac electric fields." *J. Appl. Phys.* 88(5463): 5463-5473.
54. Flanagan, L. A., J. Lu, L. Wang, S. A. Marchenko, N. L. Jeon, A. P. Lee and E. S. Monuki (2008). "Unique dielectric properties distinguish stem cells and their differentiated progeny." *Stem Cells* 26(3): 656-65.
55. Fu, A. Y., C. Spence, A. Scherer, F. H. Arnold and S. R. Quake (1999). "A microfabricated fluorescence-activated cell sorter." *Nat Biotechnol* 17(11): 1109-11
56. Gascoyne, P. R. C. and J. V. Vykoukal (2004). "Dielectrophoretic-based sample handling in general purpose programmable diagnostic instruments." *Proceedings of the IEEE* 92(1): 22-41.
57. Giddings, J. C. (1993). "Field-flow fractionation: analysis of macromolecular, colloidal, and particulate materials." *Science* 260(5113): 1456-65.
58. Lapizco-Encinas, B. H., R. V. Davalos, B. A. Simmons, E. B. Cummings and Y. Fintschenko (2005). "An insulator-based (electrodeless) dielectrophoretic concentrator for microbes in water." *J Microbiol Methods* 62(3): 317-26.
59. Lapizco-Encinas, B. H., S. Ozuna-Chacon and M. Rito-Palomares (2008). "Protein manipulation with insulator-based dielectrophoresis and direct current electric fields." *J Chromatogr A* 1206(1): 45-51.
60. Masuda, S., T. Itagaki and M. Kosakada (1988). "Detection of extremely small particles in the nanometer and ionic size range." *IEEE Trans. on Industry Applications* 24: 740-744.
61. Miltenyi, S., W. Muller, W. Weichel and A. Radbruch (1990). "High gradient magnetic cell separation with MACS." *Cytometry* 11(2): 231-8.
62. Wong, P. K. (2004). "Electrokinetics in Micro Devices for Biotechnology Applications." *IEEE/ASME Transactions on Mechatronics* 9(2): 366-376.
63. Yang, J., Y. Huang, X. B. Wang, F. F. Becker and P. R. Gascoyne (1999). "Cell separation on microfabricated electrodes using dielectrophoretic/gravitational field-flow fractionation." *Anal Chem* 71(5): 911-8.
64. Chou, C., J. Tegenfeldt, O. Bakajin, S. Chan, E. Cox, N. Darnton, T. Duke and R. Austin (2002). "Electrodeless dielectrophoresis of single- and double-stranded DNA." *Biophysical Journal* 83(4): 2170-2179.
65. Edd, J. F. and R. V. Davalos (2007). "Mathematical modeling of irreversible electroporation for treatment planning." *Technol Cancer Res Treat* 6(4): 275-86.
66. H. Pohl, Cambridge University Press: Cambridge, 1978. 1978.
67. J. Suchiro, R. Hamada, D. Noutomi, M. Shutou and M. Hara, Journal of Electrostatics, 2003, 57, 157-168.
68. H. Li and R. Bashir, Sensors and Actuators B-Chemical, 2002, 86, 215-221.
69. Y. Huang, R. Holzel, R. Pethig and X. B. Wang, Phys Med Biol, 1992, 37, 1499-1517.
70. A. Docoslis, N. Kalogerakis, L. A. Behie and K. V. Kaler, Biotechnol Bioeng, 1997, 54, 239-250.
71. T. B. Jones, Electromechanics of Particles, Cambridge University Press, USA, 1995.
72. H. Morgan, T. Sun and D. Holmes, Journal of Physics D: Applied Physics, 2007, 40.
73. H. Bruus, Theoretical Microfluidics, Oxford University Press Inc., NY, 2008.
74. L. A. Flanagan, J. Lu, L. Wang, S. A. Marchenko, N. L. Jeon, A. P. Lee and E. S. Monuki, Stem Cells, 2008, 26, 656-665.
75. P. R. C. Gascoyne, J. Noshari, T. J. Anderson and F. F. Becker, Electrophoresis, 2009, 30, 1388-1398.
76. A. Docoslis, N. Kalogerakis, L. A. Behic and K. Kaler, Biotechnology and Bioengineering, 1997, 54, 239-250.
77. H. B. Li and R. Bashir, in Biomems and Bionanotechnology, eds. R. P. Manginell, J. T. Borenstein, L. P. Lee and P. J. Hesketh, 2002, pp. 167-172.
78. C. L. Asbury, A. H. Diercks and G. van den Engh, Electrophoresis, 2002, 23, 2658-2666.
79. Ashkin, A., J. M. Dziedzic and T. Yamane, Optical trapping and manipulation of single cells using infrared laser beams. Nature, 1987. 330(6150): p. 769-71.
80. Shafiee, H., J. L. Caldwell, M. B. Sano and R. V. Davalos, Contactless dielectrophoresis: a new technique for cell manipulation. Biomed Microdevices, 2009. 11: p. 997-1006.
81. Lapizco-Encinas, B. H., B. A. Simmons, E. B. Cummings and Y. Fintschenko, Dielectrophoretic concentration and separation of live and dead bacteria in an array of insulators. Anal Chem, 2004. 76(6): p. 1571-9.
82. Green, N. G. and T. B. Jones, Numerical determination of the effective moments of non-spherical particles. Journal of Physics D-Applied Physics, 2007. 40(1): p. 78-85
83. Urdaneta, M. and E. Smela, Multiple frequency dielectrophoresis. Electrophoresis, 2007. 28(18): p. 3145-55.
84. Irimajiri, A., T. Hanai and A. Inouye, A dielectric theory of "multi-stratified shell" model with its application to a lymphoma cell. J Theor Biol, 1979. 78(2): p. 251-69.
85. Weaver, J. C., Electroporation theory: Concepts and mechanisms, in Methods in Molecular Biology. 1995, Humana Press, Inc.: Totowa, N. J. p. 3-28.
86. Davalos, R., B. Rubinsky and Y. Huang, Electroporation: bio-electrochemical mass transfer at the nano Scale. Microscale Thermophysical Engineering, 2000. 4(3): p. 147-159.
87. Lee, E. S., D. Robinson, J. L. Rognlien, C. K. Harnett, B. A. Simmons, C. R. Bowe Ellis and R. V. Davalos, Microfluidic electroporation of robust 10-microm vesicles for manipulation of picoliter volumes. Bioelectrochemistry, 2006. 69(1): p. 117-25.
88. Shafiee, H., P. A. Garcia and R. V. Davalos, A preliminary study to delineate irreversible electroporation from thermal damage using the arrhenius equation. J Biomech Eng, 2009. 131(7): p. 074509.

What is claimed is:

1. A method for separating particles in solution comprising:
   providing a sample containing particles to be separated;
   providing a dielectrophoresis device comprising:
   a channel for receiving a sample;
   a first electrode channel having a first fluid for receiving a first electrode;
   a first insulating physical barrier between the first electrode channel and the channel for receiving a sample;
   a second electrode channel having a second fluid for receiving a second electrode; and
   a second insulating physical barrier between the second electrode channel and the channel for receiving a sample, wherein application of an alternating current to the electrodes causes their capacitive coupling to the main channel and an electric field is induced across the sample fluid;
   introducing the sample into the channel for receiving the sample in a manner that causes the sample to flow through the channel, wherein the first and second insulating physical barriers completely prevent the first and second fluids from contacting the sample;
   applying an alternating electrical current to the electrodes, whereby the electrical current creates a nonuniform electric field that affects the movement of the particles to be separated differently than it affects the movement of other particles in the sample; and
   isolating the particles to be separated.

2. The method for separating particles in solution of claim 1, wherein the particles are cells.

3. The method for separating particles in a solution of claim 1, wherein the particles are viruses beads, cells, bacteria, embryos, DNA, drug molecules, amino acids, polymers, dimers, monomers, vesicles, organelles or cellular debris.

* * * * *